(12) United States Patent
Jahn et al.

(10) Patent No.: US 7,772,462 B2
(45) Date of Patent: Aug. 10, 2010

(54) RECESSIVE PLANT VIRAL RESISTANCE RESULTS FROM MUTATIONS IN TRANSLATION INITIATION FACTOR EIF4E

(75) Inventors: Margaret M. Jahn, Lansing, NY (US); Byoung-Cheorl Kang, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 953 days.

(21) Appl. No.: 10/538,434

(22) PCT Filed: Dec. 17, 2003

(86) PCT No.: PCT/US03/40184
§ 371 (c)(1),
(2), (4) Date: Jul. 31, 2006

(87) PCT Pub. No.: WO2004/057941
PCT Pub. Date: Jul. 15, 2004

(65) Prior Publication Data
US 2006/0294618 A1 Dec. 28, 2006

Related U.S. Application Data

(60) Provisional application No. 60/434,220, filed on Dec. 17, 2002.

(51) Int. Cl.
*A01H 1/00* (2006.01)
*C12N 15/82* (2006.01)
(52) U.S. Cl. ........................... 800/279; 800/278
(58) Field of Classification Search ........................ None
See application file for complete search history.

(56) References Cited

U.S. PATENT DOCUMENTS

2002/0132346 A1 9/2002 Cibelli
2003/0106101 A1 6/2003 Thompson et al.

FOREIGN PATENT DOCUMENTS

| FR | 2 835 698 A1 | 8/2003 |
| FR | 2 835 849 A1 | 8/2003 |
| WO | WO 01/40490 A2 | 6/2001 |
| WO | WO 03/066900 A2 | 8/2003 |

OTHER PUBLICATIONS

Duprat et al 2002 the Plant Journal 32:927-934.*
Guo et al. 2004, Proc. Natl. Acad. Sci. USA 101: 9205-9210.*
Hill et al 1998, Biochem. Biophys. Res. Comm. 244:573-577.*
Lazar et al. 1988, Mol. Cell. Biol. 8:1247-1252.*
Falcon-Perez JM et al. 1999, J Biol Chem. 274:23584-90.*
Duprat et al., "The *Arabidopsis* Eukaryotic Initiation Factor (iso)4E Is Dispensable for Plant Growth but Required for Susceptibility to Potyviruses," Plant J. 32:927-34 (2002).
Gallie, "Cap-independent Translation Conferred by the 5' Leader of Tobacco Etch Virus is Eukaryotic Initiation Factor 4G Dependent," J. Virol. 75(24):12141-52 (2001).
Lellis et al., "Loss-of-susceptibility Mutants of *Arabidopsis thaliana* Reveal an Essential Role for eIF(iso)4E During Potyvirus Infection," Curr. Biol. 12:1046-51 (2002).
Léonard et al., "Complex Formation Between Potyvirus VPg and Translation Eukaryotic Initiation Factor 4E Correlates with Virus Infectivity," J. Virol. 74(17):7730-7 (2000).
Nicaise et al., "The Eukaryotic Translation Initiation Factor 4E Controls Lettuce Susceptibility to the Potyvirus Lettuce mosaic virus," Plant Physiol. 132:1272-82 (2003).
Ruffel et al., "A Natural Recessive Resistance Gene Against Potato Virus Y in Pepper Corresponds to the Eukaryotic Initiation Factor 4E (eIF4E)," Plant J. 32:1067-75 (2002).
Schaad et al., "Strain-specific Interaction of the Tobacco Etch Virus NIa Protein with the Translation Initiation Factor eIF4E in the Yeast Two-hybrid System," Virol. 273:300-6 (2000).
Wittmann et al., "Interaction of the Viral Protein Genome Linked of Turnip Mosaic Potyvirus with the Translational Eukaryotic Initiation Factor (iso) 4E of *Arabidopsis thaliana* Using the Yeast Two-hybrid System," Virol. 234:84-92 (1997).
Yoshii et al., "The *Arabidopsis* Cucumovirus Multiplication 1 and 2 Loci Encode Translation Initiation Factors 4E and 4G," J. Virol. 78(12):6102-11 (2004).
Yamanaka et al., "TOM1, an *Arabidopsis* Gene Required for Efficient Multiplication of a Tobamovirus, Encodes a Putative Transmembrane Protein," Proc. Nat'l Acad. Sci. USA 97(18):10107-12 (2000).
GenBank Accession No. AAM82190.
GenBank Accession No. AAR23916.
GenBank Accession No. AAR23917.
GenBank Accession No. AAR23918.
GenBank Accession No. AAR23919.
GenBank Accession No. AAR23920.

(Continued)

*Primary Examiner*—Anne Kubelik
*Assistant Examiner*—Li Zheng
(74) *Attorney, Agent, or Firm*—Nixon Peabody LLP

(57) ABSTRACT

The present invention relates to methods of imparting virus resistance to plants. In one aspect, this method involves silencing a gene encoding a translation initiation factor eIF4E in the plant. In another aspect, this method involves overexpressing a heterologous translation initiation factor eIF4E in a plant. The present invention further relates to a genetic construct containing a nucleic acid molecule encoding a heterologous translation initiation factor eIF4E, as well as to an expression system containing the genetic construct and a host cell transformed with the genetic construct. The present invention also relates to transgenic plants, seeds, and plant parts transformed with the genetic construct. The present invention also relates to an isolated nucleic acid molecule encoding a mutant translation initiation factor eIF4E that is effective in imparting virus resistance in plants. The present invention also relates to a mutant translation initiation factor eIF4E and a method for making the mutant.

17 Claims, 14 Drawing Sheets

OTHER PUBLICATIONS

GenBank Accession No. AY122052.
GenBank Accession No. AY485129.
GenBank Accession No. AY485130.
GenBank Accession No. AY485131.

* cited by examiner

A

B

C pBI:eIF4E RN-AS

A pBI:eIF4E 234-AS

B pBI:eIF4E TAB-AS

C

Amplification confirming putative transformants.

NPTII PCR reaction for testing putative transformants.

A

B

RECESSIVE PLANT VIRAL RESISTANCE RESULTS FROM MUTATIONS IN TRANSLATION INITIATION FACTOR EIF4E

This application claims the benefit of U.S. Provisional Patent Application Ser. No. 60/434,220, filed Dec. 17, 2002, which is hereby incorporated by reference in its entirety.

The present invention was made with funding received from the United States Department of Agriculture under USDA NRICGP Plant Genome Award No. 94-37300-0333 and USDA IFAFS Award No. 2001-52100-11334. The U.S. Government may have certain rights in this invention.

FIELD OF THE INVENTION

The present invention relates to the methods of imparting virus resistance to plants by silencing a gene encoding a translation initiation factor eIF4E and/or by overexpressing in a plant a nucleic acid molecule encoding a heterologous translation initiation factor eIF4E.

BACKGROUND OF THE INVENTION

Plant virus diseases can damage leaves, stems, roots, fruits, seed, or flowers, and are responsible for a considerable percentage of economic loss due to reduced crop yield and quality (Agrios, "Chapter 14: Plant Diseases Caused By Viruses," in *Plant Pathology*, 3rd Ed., San Diego, Calif.: Academic Press, p. 655 (1988)).

Control of plant virus diseases took a major step forward when it was shown that the tobacco mosaic virus ("TMV") coat protein ("CP") gene that was expressed in transgenic tobacco conferred resistance to TMV (Powell-Abel et al., "Delay of Disease Development in Transgenic Plants that Express the Tobacco Mosaic Virus Coat Protein Gene," *Science* 232:738-43 (1986)). The concept of pathogen-derived resistance ("PDR"), which states that pathogen genes that are expressed in transgenic plants will confer resistance to infection by the homologous or related pathogens (Sanford et al., "The Concept of Parasite-Derived Resistance—Deriving Resistance Genes from the Parasite's Own Genome," *J. Theor. Biol.*, 113:395-405 (1985)) was introduced at about the same time. Since then, numerous reports have confirmed that PDR is a useful strategy for developing transgenic plants that are resistant to many different viruses (Lomonossoff, G. P., "Pathogen-Derived Resistance to Plant Viruses," *Ann. Rev. Phytopathol.*, 33:323-43 (1995)). However, additional modes of protecting plants against virus disease are needed.

Recessive disease resistance genes are widely deployed in agriculture and are common in nature. However, not much is understood about the identity of naturally occurring recessive disease resistance genes in plants. Plant disease resistance conferred by recessive genetic factors has received limited attention relative to dominant R genes, despite their durability and prevalence in nature. Thus, there is a need to identify, isolate, and clone plant host genes whose gene product is essential for pathogenesis. This knowledge would be useful in that it would enable one to engineer disease resistance the various gene silencing methods available in the art.

Potyviruses comprise approximately 30% of all known plant viruses and as a group are very destructive in agriculture (Ward et al., "Taxonomy of Potyviruses: Current Problems and Some Solutions," *Intervirology* 32:269-296 (1991)). The family Potyviridae is characterized by a monopartite single-stranded positive sense RNA genome with a covalently-bound viral-encoded protein (VPg) attached at the 5' terminus and a 3' poly-A tract (Riechmann et al., "Highlights and Prospects of Potyvirus Molecular Biology," *J. Gen. Virol.* 73:1-16 (1992)). The genome is approximately 10 kb in length and is translated as a polyprotein which is subsequently cleaved into smaller polypeptides by viral-encoded proteases. Based on similarities in genome structure, including conserved order and function among homologous replication proteins, potyviruses have been assigned to the proposed picorna-like superfamily of viruses, which includes many important human and animal pathogens, such as poliovirus and foot-and-mouth disease virus (Goldbach et al., "Genetic Organization, Evolution and Expression of Plant Viral RNA Genomes," In Fraser, ed., *Recoginition and Response in Plant-Virus Interactions*, Heidelberg:Springer-Verlag, pp. 147-162 (1990); and Riechmann et al., "Highlights and Prospects of Potyvirus Molecular Biology," *J. Gen. Virol.* 73:1-16 (1992)).

Potyvirus infection requires the interaction of host factors with viral proteins and RNA for replication and systemic spread (Carrington et al., "Cell-to-Cell and Long-Distance Transport of Viruses in Plants," *Plant Cell* 8:1669-1681 (1996)). Although much is known regarding the functions of the individual potyvirus proteins and RNA structures in viral replication and movement (reviewed in Revers et al., "New Advances in Understanding the Molecular Biology of Plant/Potyvirus Interactions," *Mol. Plant Microbe Interact.* 12:367-376 (1999); Riechmann et al., "Highlights and Prospects of Potyvirus Molecular Biology," *J. Gen. Virol.* 73:1-16 (1992); and Urcuqui-Inchima et al., "Potyvirus Proteins: A Wealth of Functions," *Virus Res.* 74:157-175 (2001)), very little is understood about the identity and functions of host factors that are required for potyviral infection. Towards this end, the identification of naturally occurring host mutations that result in viral resistance and display monogenic recessive inheritance should define an important resource. The "negative model" of plant virus resistance predicts that a recessive resistance gene may represent a deleted or defective host protein that is essential for viral infection but is dispensable for the host (Fraser, "The Genetics of Plant-Virus Interactions: Implications for Plant Breeding," *Euphytica* 63:175-185 (1992)). Recessive resistance is especially prevalent for potyviruses, comprising approximately 40% of all known resistance genes (Provvidenti et al., "Sources of Resistance to Viruses in the Potyviridae," *Arch. Virol.* 5:189-211 (1992)). Many of these genes, including the *Capsicum* resistance gene pvr1, have been used successfully for decades in crop breeding programs as effective and stable sources of resistance (Greenleaf, "Pepper Breeding," In Basset, ed., *Breeding Vegetable Crops*, Westport, Conn.: AVI Pub., pp. 67-134 (1986)).

The potyviral NIa protein, also known as VPg-Pro, is comprised of an N-terminal VPg and C-terminal protease and participates in several replicative and proteolytic functions during potyvirus infection (Revers et al., "New Advances in Understanding the Molecular Biology of Plant/Potyyirus Interactions," *Mol. Plant Microbe Interact.* 12:367-376 (1999)). The central region of VPg has been shown to be crucial in race-specific replication, cell-to-cell and long-distance movement functions in relation to recessive potyvirus resistance genes (Keller et al., "Potyvirus Genome-Linked Protein (VPg) Determines Pea Seed-Borne Mosaic Virus Pathotype-Specific Virulence in *Pisum sativum*," *Mol. Plant Microbe Interact.* 11:124-130 (1998); Masuta et al., "A Single Amino Acid Change in Viral Genome-Associated Protein of Potato Virus Y Correlates with Resistance Breaking in 'Virgin A Mutant' Tobacco," *Phytopathology* 89:118-123 (1999); Nicolas et al., "Variations in the VPg Protein Allow a Potyvirus to Overcome va Gene Resistance in Tobacco," *Virology* 237:452-459 (1997); Rajamaki et al., "Viral Genome-Linked Protein (VPg) Controls Accumulation and Phloem-Loading of a Potyvirus in Inoculated Potato Leaves," *Mol. Plant Microbe Interact.* 15:138-149 (2002); and Schaad et al., "VPg of Tobacco Etch Potyvirus is a Host Genotype-Specific Determinant for Long-Distance Movement," *J. Virol.* 71:8624-8631 (1997)). The importance of NIa in potyvirus replication and movement has also prompted studies to identify host factors that interact with this protein using in vitro interaction assays. One study showed strong interaction in yeast two-hybrid assays between Tobacco etch virus (TEV) NIa and translation initiation factor eIF4E isolated from tomato and tobacco (Schaad et al., "Strain-Specific Interaction of the Tobacco Etch Virus NIa Protein with the Translation Initiation Factor eIF4E in the Yeast Two-Hybrid System," *Virology* 273:300-306 (2000)). Strong interactions have also been observed between *Arabidopsis thaliana* eIF4E or eIF (iso)4E and Turnip mosaic virus (TuMV) VPg-Pro both in yeast two-hybrid and ELISA-based in vitro binding assays (Wittmann et al., "Interaction of the Viral Protein Genome Linked of Turnip Mosaic Potyvirus with the Translational Eukaryotic Initiation Factor (iso) 4E of *Arabidopsis thaliana* Using the Yeast Two-Hybrid System," *Virology* 234:84-92 (1997)). Furthermore, the interaction of *Arabidopsis* eIF(iso) 4E and TuMV VPg-Pro correlated with viral infectivity (Leonard et al., "Complex Formation Between Potyvirus VPg and Translation Eukaryotic Initiation Factor 4E Correlates with Virus Infectivity," *J. Virol.* 74:7730-7737 (2000)).

The present invention is directed to overcoming these deficiencies in the art.

SUMMARY OF THE INVENTION

The present invention relates to a method of imparting virus resistance to plants. This method involves silencing a gene encoding a translation initiation factor eIF4E in the plant under conditions effective to impart virus resistance to the plant.

The present invention also relates to a genetic construct containing a nucleic acid molecule which silences a gene encoding a translation initiation factor eIF4E in a plant. The genetic construct further contains a plant promoter heterologous to the nucleic acid molecule. The geneic construct also contains a terminator. The plant promoter and the terminator are operatively coupled to the nucleic acid molecule. The present invention further relates to an expression system containing the genetic construct and a host cell transformed with the genetic construct.

The present invention also relates to a plant transformed with a genetic construct that contains: (i) a nucleic acid molecule which silences a gene encoding a translation initiation factor eIF4E in a plant; (ii) a plant promoter; and (iii) a terminator. The plant promoter and the terminator are operatively coupled to the nucleic acid molecule. Further, either the nucleic acid molecule, the plant promoter, or the terminator are heterologous to the transformed plant. The present invention further relates to a component part of, a fruit of, and a plant seed produced from the transformed plant.

The present invention also relates to a plant seed transformed with a genetic construct containing: (i) a nucleic acid molecule which silences a gene encoding a translation initiation factor eIF4E in a plant; (ii) a plant promoter; and (iii) a terminator. The plant promoter and the terminator are operatively coupled to the nucleic acid molecule. Further, either the nucleic acid molecule, the plant promoter, or the terminator are heterologous to the transformed plant seed.

The present invention relates to an isolated nucleic acid molecule encoding a mutant translation initiation factor eIF4E that is effective in imparting virus resistance in plants. The nucleic acid molecule encodes a mutant translation initiation factor eIF4E having an amino acid sequence of SEQ ID NO:4 and variants thereof that are at least 95 percent similar to SEQ ID NO:4. Alternatively, the nucleic acid molecule encodes a mutant translation initiation factor eIF4E having an amino acid sequence of SEQ ID NO:6 and variants thereof that are at least 95 percent similar to SEQ ID NO:6. Alternatively, the nucleic acid molecule encodes a mutant translation initiation factor eIF4E having an amino acid sequence of SEQ ID NO:8 and variants thereof that are at least 95 percent similar to SEQ ID NO:8. Alternatively, the nucleic acid molecule encodes a mutant translation initiation factor eIF4E having an amino acid sequence that is at least 85 percent similar to a non-mutant translation initiation factor eIF4E of SEQ ID NO:2 and containing at least one substitution of at least one amino acid residue of SEQ ID NO:2 selected from the group consisting of T51A, P66T, V67E, K71R, L79R, G107P, and D109R. The present invention also relates to an isolated mutant translation initiation factor eIF4E encoded by the isolated nucleic acid molecule. The present invention further relates to a recombinant expression system and a host cell containing the isolated nucleic acid molecule, as well as a transgenic plant and a transgenic plant seed transformed with the isolated nucleic acid molecule.

The present invention also relates to a method of making a mutant translation initiation factor eIF4E. This method involves growing a host cell containing an isolated nucleic acid molecule encoding a mutant translation initiation factor eIF4E of the present invention under conditions whereby the host cell expresses the mutant translation initiation factor eIF4E. The mutant translation initiation factor eIF4E is then isolated.

The present invention also relates to a method of making a transgenic plant having enhanced virus resistance compared to that of a non-transgenic plant. This method involves transforming a non-transgenic plant cell with a nucleic acid molecule encoding a mutant translation initiation factor eIF4E of the present invention under conditions effective to yield a transgenic plant cell having enhanced virus resistance compared to that of a non-transgenic plant. A transgenic plant is regenerated from the transformed plant cell. The present invention further relates to a transgenic plant and plant seed produced by this method.

The present invention also relates to a method of imparting virus resistance to plants by providing a nucleic acid molecule encoding a heterologous translation initiation factor eIF4E. A plant is transformed with the nucleic acid molecule under conditions effective to yield a transgenic plant that overexpresses the heterologous translation initiation factor eIF4E. This method is effective in imparting virus resistance to the transgenic plant. The present invention also relates to transgenic plants produced by this method, as well as component parts, seeds, and fruits of the transgenic plant.

BRIEF DESCRIPTION OF THE DRAWINGS

FIG. 1A: RFLP detected with eIF4E-687 ORF probe cosegregated with susceptible (S) or resistant (R) phenotypes in an interspecific $F_2$ population of 75 individuals screened with PepMoV. FIG. 1B: The SstI CAPS marker P56 cosegregated with response to TEV-HAT and PepMoV-FL in 114 *C. chinense* $F_3$ families scored resistant (R), segregating (H), or uniformly susceptible (S) to both viruses. FIG. 1C: pvr1 and pvr$2^2$ fail to genetically complement. Black bars: screened $F_1$ populations from inter-crossing *C. annuum*

'5502' or '3618' (pvr1/pvr1) with 'Florida VR2' (VR2) or 'Dempsey' (DEMP) (pvr2²/pvr2²) were resistant to TEV-HAT; susceptible check, *C. annuum* 'Jupiter'. Hatched bars: 5502×DEMP F₂ population was resistant to TEV-HAT; susceptible check, *C. annuum* 'Early Cal Wonder' (ECW).

FIGS. 2A-2B show amino acid alignments and crystal structure comparisons of mouse eIF4E and eIF4E-687. FIG. 2A: Amino acid alignment of mouse eIF4E with eIF4E-687 sequences from *Capsicum*. *Capsicum* sequences were aligned with the reference pvr1⁺ sequence *C. annuum* 'NuMex RNaky' (RN) using the Clustal algorithm of DNASTAR. Other pvr1⁺ genotypes: *C. annuum* 'Early Cal Wonder' (ECW) and *C. chinense* 'Habanero' (HAB); pvr1/pvr1 genotypes: *C. chinense* PI 152225 (225), PI 159236 (236), PI 159234 (234) and *C. annuum* '3618', '4074', and '5502'; pvr1²/pvr1² (also referred to as pvr2²/pvr2²) genotypes: *C. annuum* 'Dempsey' (DEMP), 'DelRay Bell' (DRB) and 'Florida VR2' (VR2); pvr1¹/pvr1¹ (also referred to as pvr2¹/pvr2¹) genotype: *C. annuum* 'Yolo Y' (YY). RN amino acids identical to mouse are denoted by vertical bars; substitutions resulting in a similar amino acid are indicated by colons. Amino acids widely conserved across kingdoms (Marcotrigiano et al., "Cocrystal Structure of the Messenger RNA 5' Cap-Binding Protein (eIF4E) Bound to 7-Methyl-GDP," *Cell* 89:951-961 (1997), which is hereby incorporated by reference in its entirety) are underlined. Highly conserved cap-binding residues are colored red. Amino acid substitutions specific to pvr1 are colored green. Amino acid substitutions shared by pvr1¹ and pvr1² are in yellow. The substitution specific to pvr1² is colored blue. Upper and lower rulers denote mouse and pepper amino acid position, respectively. Functional classifications are: s, stacking tryptophan; d, conserved dorsal residue; g, hydrogen bonding to guanine; r, stabilizing Arg-157; p, interaction with phosphate groups of m⁷GDP; m, van der Waals interaction with m⁷GDP; *, site of phosphorylation. *Capsicum* amino acids identical to RN are denoted by a period; substituted residues are listed by symbol. FIG. 2B: Comparison of eIF4E-687 alleles from potyvirus-susceptible and resistant *Capsicum* genotypes using models derived from the crystal structure of mouse eIF4E. Space-filling (upper) and chain (lower) models depict backbones of the proteins in gray with side-chains shown only for colored residues. Highly conserved cap-binding residues are shown in red labeled with their position in the pepper protein. Left panel: homology model of eIF4E-687 from pvr1⁺ genotype *C. annuum* 'NuMex RNaky' (RN); center panel: the homology model for eIF4E-687 from pvr1 genotypes with amino acid substitutions (green) relative to RN labeled by position; right panel, a composite homology model for eIF4E-687 showing substitutions shared by pvr1¹ and pvr1² (yellow) and the unique mutation in pvr1² (blue).

Figure 3:
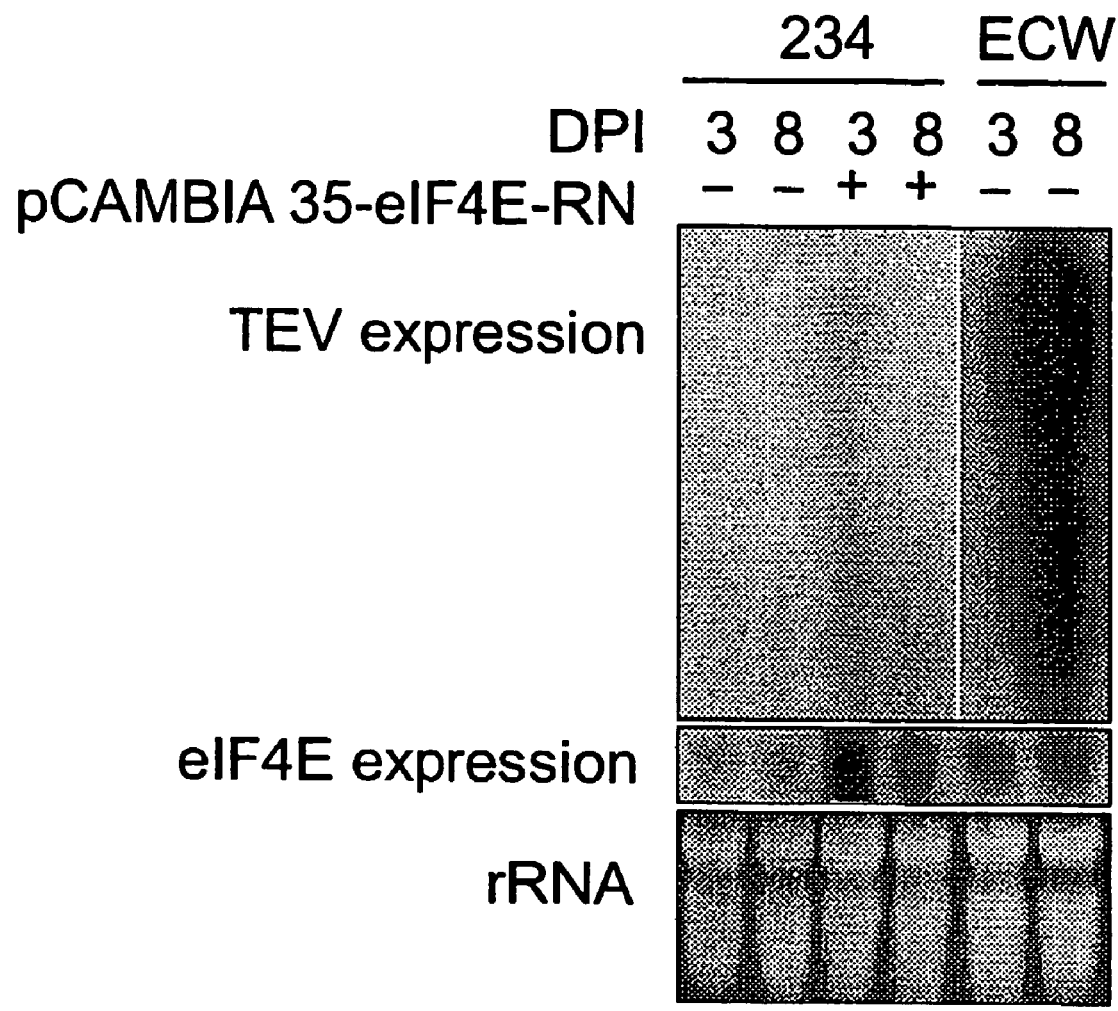

FIG. 3 shows transient expression of eIF4E-687-RN functionally complemented pvr1. *Agrobacterium* strain C58C1 cultures with and without pCAMBIA35S-eIF4E-687-RN or containing pCAMBIA-GFP grown under vir gene-inducing conditions and infiltrated into the intracellular spaces of the TEV-resistant pepper leaves at the 24 true leaf stage. Three days after infiltration, crude extract from TEV-HAT infected tobacco KY14 ground in 0.05 M potassium phosphate was rub-inoculated on the same leaves. Total RNA was isolated from the inoculated leaves 3 and 8 days after inoculation and subjected to RNA blot analysis probed with TEV VPg to detect viral genome amplification and eIF4E-687 overexpression.

Figure 4:
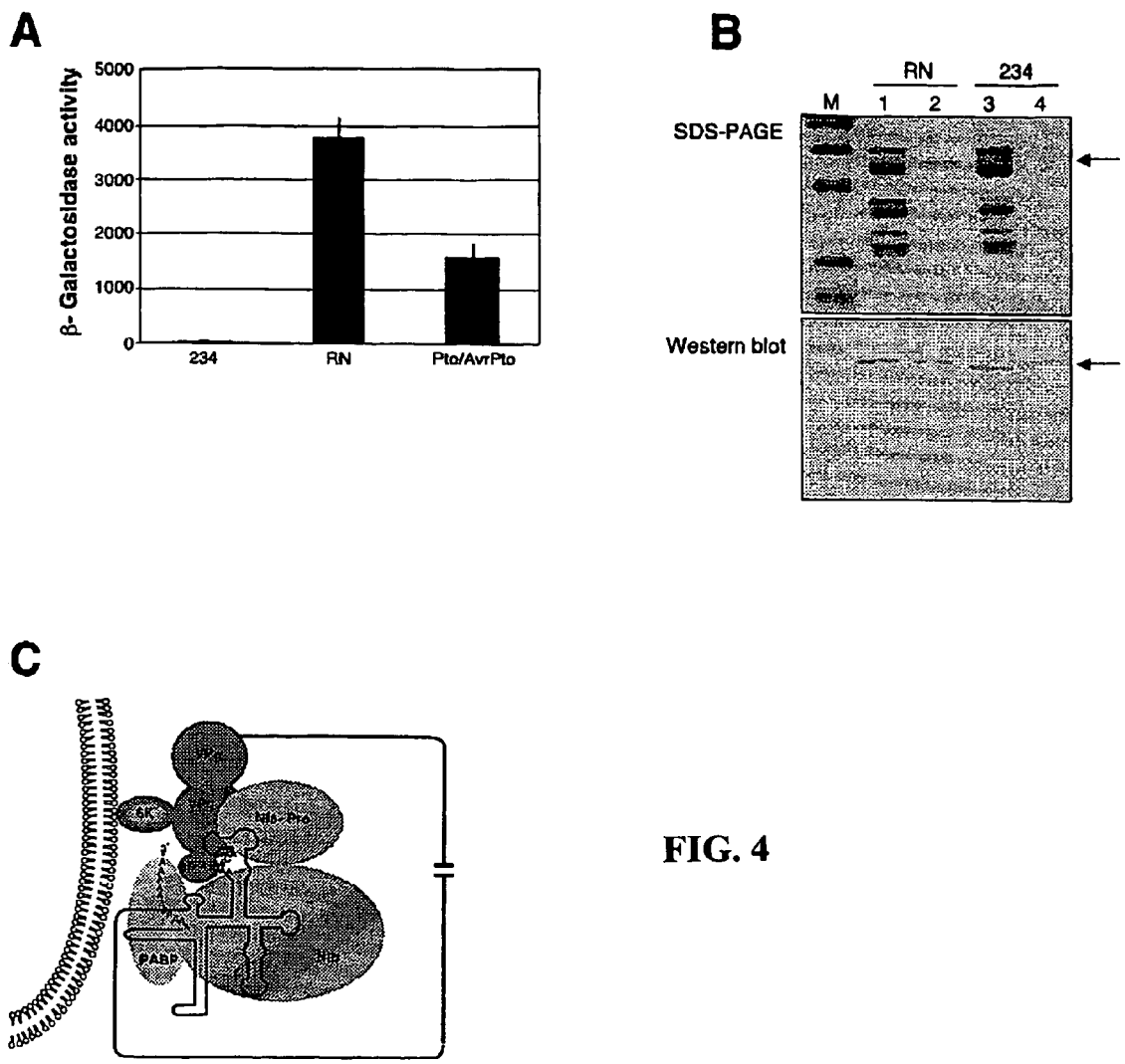

FIGS. 4A-4C show that the eIF4E-687-234 allele failed to interact with TEV-HAT-VPg and mRNA cap analogs in vitro. FIG. 4A: β-galactosidase assay of yeast two-hybrid interaction between TEV-HAT VPg and alleles isolated from RN(S) and 234 (R). Bait plasmid pEG202 was used to express the fusion protein TEV-HAT VPg. The prey plasmid pJG4-5 was used to express pepper eIF4E. pEG202: Pto and pJG4-5: AvrPto were served as a positive control. FIG. 4B: Cap-binding assay of pepper eIF4E-687 sequences expressed in *E. coli* from susceptible RN and resistant 234. Upper panel: Coomassie blue-stained gel of the eIF4E-GST fusion proteins. Lane 1 and 3: eIF4E fusion proteins purified by GST-Sepharose column; lane 2 and 4: eIF4e fusion proteins purified by m⁷-GTP-Sepharose column; lane M: pre-stained size marker. Lower panel: corresponding immunoblot probed with human eIF4E antibody. Arrows indicate eIF4E fusion protein bands. FIG. 4C: A model depicting proposed roles of eIF4E-687-VPg interaction in the cellular resistance mechanism of pvr1 and pvr2². An ER-derived membrane is shown in the upper left corner. Proteins are depicted as follows: 6K (dark gray), VPg (blue), NIa-Pro (green), NIb (brown), poly-A binding protein (PABP) (yellow), eIF4E-687 (red), and eIF4G (light gray). A positive stranded template for negative strand RNA synthesis (approximately 10 kb) is depicted in black with 5' VPg attached (blue). The picornavirus cis-replicating element (cre) motif AAACA and poly-A tail are indicated. The viral 6K protein, prior to cleavage from VPg and NIa-Pro domains of NIa, anchors the replication complex to the ER membrane. NIa-Pro recruits NIb to prime VPg via uridylylation of a tyrosine (Murphy et al., "A Tyrosine Residue in the Small Nuclear Inclusion Protein of Tobacco Vein Mottling Virus Links the VPg to the Viral RNA," *J. Virol.* 65:511-3 (1991), which is hereby incorporated by reference in its entirety) for replication (Schaad et al., "Formation of Plant RNA Virus Replication Complexes on Membranes: Role of an Endoplasmic Reticulum-Targeted Viral Protein.," *Embo J.* 16:4049-59 (1997), which is hereby incorporated by reference in its entirety). In picornaviruses, the VPg-priming template is a cis-acting replicative element (cre), a stem-loop structure containing the conserved motif AAACA (Paul et al., "Identification of an RNA Hairpin in Poliovirus RNA that Serves as the Primary Template in the In vitro Uridylylation of VPg," *J. Virol.* 74:10359-70 (2000), which is hereby incorporated by reference in its entirety). TEV also has 3'cis-required elements for replication including a prominent stem-loop structure containing AAACA (Haldeman-Cahill et al., "Secondary Structures in the Capsid Protein Coding Sequence and 3' Nontranslated Region Involved in Amplification of the Tobacco Etch Virus Genome," *J. Virol.* 72:4072-9 (1998), which is hereby incorporated by reference in its entirety). This same region in TEV contains a conserved sequence motif from a luteovirus 3' translational enhancer that has been shown to bind eIF4E and eIF(iso)4E (Wang et al., "A Viral Sequence in the 3'-Untranslated Region Mimics a 5' Cap in Facilitating Translation of Uncapped mRNA," *Embo J.* 16:4107-16 (1997); and Miller et al., "The RNA World in Plants: Post-Transcriptional Control III," *Plant Cell* 13:1710-7 (2001), which are hereby incorporated by reference in their entirety). It is proposed that in potyvirus infection, eIF4E binds directly to the cre site to recruit VPg to the uridylylation template. NIa-Pro then binds and stabilizes the RNA while recruiting the NIb polymerase to catalyze the uridylylation reaction similar to polio 3CDpro and 3Dpol (Paul et al., "Identification of an RNA Hairpin in Poliovirus RNA that Serves as the Primary Template in the In vitro Uridylylation of VPg," *J. Virol.* 74:10359-70 (2000), which is hereby incorporated by reference in its entirety). A host uridylyl transferase-like protein identified in tomato as an interacting protein with TEV VPg may represent an alternate catalyst to NIb (Schaad et al., "Strain-Specific Interaction of the Tobacco Etch Virus NIa Protein with the Translation Initiation Factor eIF4E in the Yeast Two-Hybrid System," *Virology* 273:300-6 (2000), which is hereby incorporated by reference in its entirety). The interaction of NIb with host PABP (Wang et al., "Interaction Between Zucchini Yellow Mosaic Potyvirus RNA-Dependent RNA Polymerase and Host Poly-(A) Binding Protein," *Virology* 275:433-43 (2000), which is hereby incorporated by reference in its entirety) brings the poly-A tail to the VPg priming site so RNA replication could proceed efficiently. It is possible that eIF4E-687 and PABP may enter the replication complex bound to eIF4G. Mutant eIF4E that binds the cre site but fails to interact with VPg, or bind VPg and fails to bind the cre site, would block the replication process.

Figure 5:
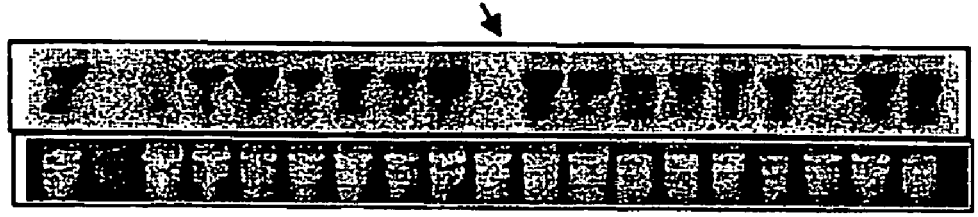
Figure 5:
Figure 5:
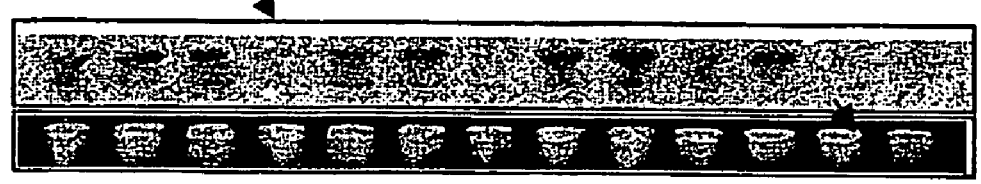
Figure 6:
Figure 7:
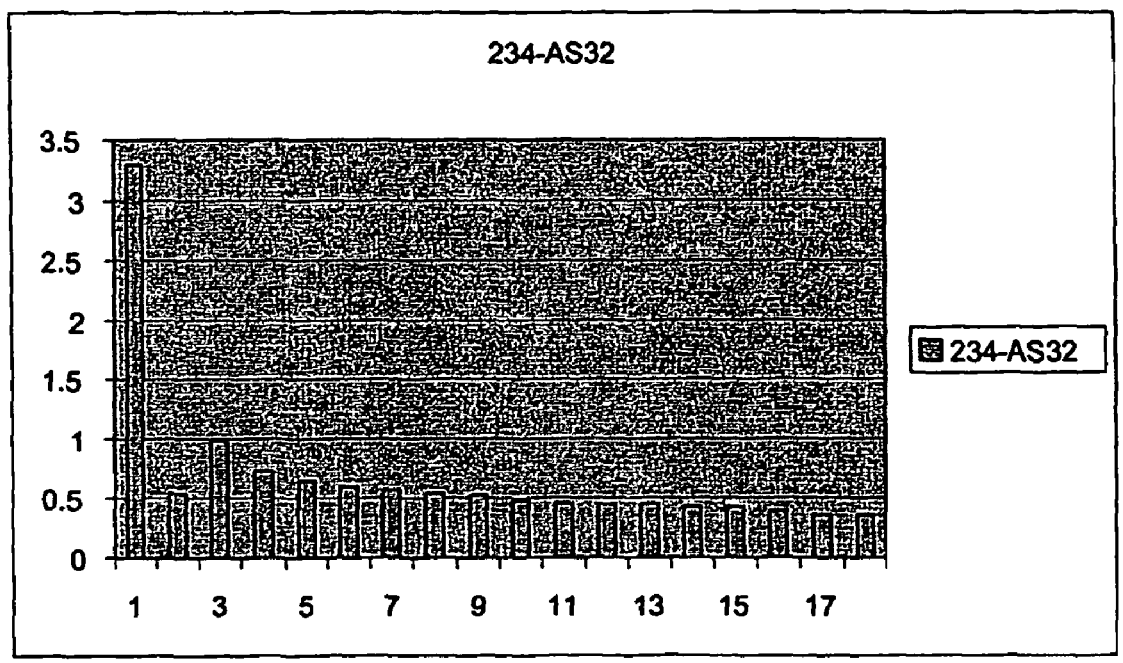

FIGS. 5A-5C show a Northern blot analysis of eIF4E gene expression of transgenic lines (T0) using pBI:eIF4E RN-AS (FIG. 5A), pBI:eIF4E 234-AS (FIG. 5B), and pBI:eIF4E TAB-AS (FIG. 5C). Key: *: untransformed control. ↓: selected transgenic lines.

FIG. 6 shows results from an NPTII PCR reaction for testing putative transformants. Amplification confirmed putative transformants.

FIG. 7 is a graph showing an example of ELISA data from a T1 progeny silenced for eIF4E. The first two bars represent the positive (infected) and negative (uninfected) controls, respectively. The rest of the bars represent individual TEV-inoculated asymptomatic transgenic segregants silenced for eIF4E. The amount of detectable viral antigen in inoculated transgenic plants is comparable to negative control treatments indicating that silencing eIF4E results in resistance to TEV.

FIGS. 8A-8B demonstrate that eIF4E-687 cosegregates with pvr1. FIG. 8A: Polymorphism detected with eIF4E-687 ORF probe cosegregated with susceptible (S) or resistant (R) phenotypes in an interspecific $F_2$ population of 75 individuals screened with PepMoV. Susceptible parent *C. annuum* 'NuMex RNaky' (RN) and resistant parent *C. chinense* PI 159234 (234) are indicated. FIG. 8B: The SspI CAPS marker P56 co-segregated with response to TEV-HAT and PepMoV in 114 *C. chinense* $F_3$ families scored resistant (R), segregating (H), or uniformly susceptible (S) to virus infection in two independent screens. Susceptible parent 'Habanero' (HAB) and resistant parent PI 159234 (234) are indicated. M=marker lane.

FIGS. 9A-9B show the results of a complementation analysis of pvr1 and $pvr2^2$. FIG. 9A: pvr1 and $pvr2^2$ fail to genetically complement for resistance to TEV-HAT. Black bars: Screened $F_1$ populations from inter-crossing *C. annuum* '5502' or '3618' (both pvr1/pvr1) with 'Dempsey' (DEMP) or 'Florida VR2' (VR2) (both $pvr2^2/pvr2^2$) were resistant to TEV-HAT based on indirect ELISA absorbance readings (21 dpi). The susceptible check was *C. annuum* 'Jupiter'. Hatched bars: The (5502×DEMP) $F_2$ population was also resistant to TEV-HAT; susceptible check, *C. annuum* 'Early Cal Wonder' (ECW). FIG. 9B: Functional complementation evident as TEV accumulation in pvr1 plants by transient expression of eIF4E-RN. *Agrobacterium* LBA4404 harboring eIF4E-234 and eIF4E-RN alleles were infiltrated into leaves of 234 plants and 3 days after agro-infiltration, TEV-HAT virus was inoculated on the leaves. Five days after TEV inoculation, inoculated leaves were harvested and subjected to immunoblot analysis with anti-eIF4E and anti-TEV antisera.

FIG. 10 is a two-dimensional drawing showing the structure of the eIF4E-687 locus. White boxes represent coding sequences. Black boxes represent the 28 bp 5' and 156 bp 3' untranslated regions (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety). Translational start (ATG) and stop (TAA) sites are indicated. Locations of sequence-based SspI CAPS marker P56 (FIG. 9B) and MseI CAPS marker E23 used to confirm cosegregation of eIF4E-687 with the resistance phenotype are depicted. The gray box on the left represents a 66 bp upstream sequence with 92% identity with bases 80-146 of the eIF4E-687 open reading frame.

FIGS. 11A-11B are graphs showing disrupted interaction between eIF4E-687 and TEV NIa does not correlate with resistance phenotype. FIG. 11A: β-galactosidase assay of yeast two-hybrid interaction between TEV NIa proteins and eIF4E-687 from RN ($pvr1^+$), HAB ($pvr1^+$), 234 (pvr1), DEMP ($pvr1^2$) and YY ($pvr1^1$). Bait plasmid pEG202 was used to express the fusion protein TEV-HAT NIa (upper panel), and TEV-NW NIa (lower panel), while the prey plasmid pJG4-5 was used to express pepper eIF4E-687. The empty vector pJG4-5 was used as a negative interaction control. Yeast containing known interactors pEG202: TEV-HAT NIa and PJG4-5: TEV-HAT NIb served as a positive interaction control. FIG. 11B: Representative response of pvr genotypes to TEV-HAT (upper panel) or TEV-NW (lower panel) inoculation. Indirect ELISA absorbance values (21 dpi) are indicated for the varieties ECW ($pvr1^+$), RN ($pvr1^+$), HAB ($pvr1^+$), 234 (pvr1), DEMP ($pvr1^2$) and YY ($pvr1^1$). ECW—represents the mock-inoculated negative control.

FIG. 12 shows that only the allele eIF4E-RN binds VPg-HAT and VPg-NW. Pull-down assays were conducted with GST, GST-VPgHAT, and GST-VPgNW immobilized on glutathione-Sepharose 4B beads and $^{35}S$-labeled in vitro-translated eIF4E alleles, 234 (pvr1), DEMP ($pvr1^2$), RN ($pvr1^+$), and YY ($pvr1^1$). The input protein panel represents equivalent amounts of GST, GST-VPgHAT, and GST-VPgNW used in the pull-downs assay and 20% of in vitro-translated eIF4Es. An arrow indicates GST fusion proteins. Pull-down eluates were separated by 12% SDS-PAGE and exposed to a phosphorimager screen.

FIGS. 13A-13B show that Cap-binding ability does not correlate with resistance among the mutant eIF4E-687 alleles. Binding assay of recombinant eIF4E proteins to $m^7$-GTP-sepharose. FIG. 13A: Expression of eIF4E-687 proteins in *E. coli* (DE3) and immunoblot analysis. Upper panel: Coumassie blue-stained 12% SDS-polyacrylamide gel of whole cell lysates of *E. coli* before (U) and after (I) induction by the addition of 100 μM IPTG. Arrows indicate the position of recombinant protein. Lower panel: Immunoblot analysis of recombinant eIF4E-687. The same amount of protein as in the upper panel was resolved by SDS-PAGE, and the expression of the proteins was monitored by immunoblot analysis using rabbit antiserum specific for human eIF4E. M=molecular size marker, U=uninduced I=induced. FIG. 13B: SDS-PAGE analysis of recombinant eIF4E-687 proteins after $m^7$-GTP-Sepharose affinity chromatography. The soluble fraction of bacterial cell lysates was applied to the $m^7$-GTP-Sepharose column and eluted with extraction buffer containing 100 μM $m^7$-GTP. M=molecular size marker; E1-E4: Eluted fractions using $m^7$-GTP.

FIG. 14 shows the results of analyses of virus resistance in transgenic tomato plants containing sense eIF4E genes. Plants were inoculated and analyzed as described in Examples 34-37, infra. The upper panel shows dot blot analyses and the lower panel shows pictures of TEV inoculated transgenic plants. Note that progenies of eIF4E overexpressing transgenic plant, pBI::234-S9, show no symptoms of TEV infection and no accumulation of TEV coat protein.

DETAILED DESCRIPTION OF THE INVENTION

The present invention relates to a method of imparting virus resistance to plants. This method involves silencing a gene encoding a eukaryotic translation initiation factor 4E ("eIF4E") in the plant under conditions effective to impart virus resistance to the plant.

The gene product of the eIF4E gene is part of the eIF4F complex (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety). In this complex, eIF4E provides a 5' cap-binding function during formation of translation initiation complexes in mRNAs of eukaryotes. Silencing a virus disease susceptible plant host's eIF4E gene can be effective in imparting virus resistance to plants. In particular, this can be done, for example, by using recombinant technology.

A suitable gene encoding the translation initiation factor eIF4E ("eIF4E gene") that can be targeted for silencing can include, for example, any plant eIF4E gene naturally occurring in a virus-susceptible plant. In one embodiment, a suitable eIF4E gene can have a nucleotide sequence that is at least 70 percent similar to SEQ ID NO:1 (described, infra). In another embodiment, a suitable eIF4E gene can have a nucleotide sequence that is at least 90 percent similar to SEQ ID NO:1. In another embodiment, a suitable eIF4E gene can have a nucleotide sequence that is at least 95 percent similar to SEQ ID NO:1. In yet another embodiment, the eIF4E gene can have a nucleotide sequence that hybridizes to SEQ ID NO:1 under stringent hybridization conditions involving, for example, hybridization in a hybridization buffer containing, for example, 20 percent formamide in 0.9M saline/0.09M SSC buffer, at a temperature of about 42° C. Other suitable stringent conditions are described below.

For the purposes of defining the level of stringency, reference can conveniently be made to Sambrook et al., *Molecular Cloning: A Laboratory Manual,* 2nd Edition, Cold Spring Harbor, N.Y., Cold Spring Harbor Laboratory Press, at 11.45 (1989) which is hereby incorporated by reference in its entirety. An example of low stringency conditions is 4-6× SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4× SSC/0.25% w/v SDS at >45° C. for 2-3 hours. An example of high stringency conditions includes 0.1-1×SSC/0.1% w/v SDS at 60° C. for 1-3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05× BLOTTO, and washing at 2×SSC, 0.1% SDS at 62° C.

In one embodiment of the present invention's method of imparting virus disease resistance to plants, "silencing" involves providing a transgenic plant or plant seed transformed with a "nucleic acid molecule which silences a gene encoding a translation initiation factor eIF4E." The transgenic plant, or a transgenic plant grown from the transgenic plant seed, is grown under conditions effective to impart virus resistance to the transgenic plant.

As used herein, the term "a heterologous nucleic acid molecule which silences a gene encoding a translation initiation factor eIF4E" refers to a nucleic acid molecule that is not contained in the transgenic plant or plant seed prior to transformation. Fragments of such nucleic acid molecules that retain their functional ability to impart virus resistance to plants can also be used in accordance with the present invention.

A suitable nucleic acid molecule for use in the methods of the present invention can be one that encodes an amino acid sequence of SEQ ID NO:4 and/or variants thereof that are at least 95 percent similar to SEQ ID NO:4. As used herein, SEQ ID NO:4 corresponds to the amino acid sequence encoded by the eIF4E-234 gene (described, infra).

Another suitable nucleic acid molecule for use in the methods of the present invention can be one that encodes an amino acid sequence of SEQ ID NO:6 and/or variants thereof that are at least 95 percent similar to SEQ ID NO:6. As used herein, SEQ ID NO:6 corresponds to the amino acid sequence encoded by the eIF4E-YY gene (described, infra).

Another suitable nucleic acid molecule for use in the methods of the present invention can be one that encodes an amino acid sequence of SEQ ID NO:8 and variants thereof that are at least 95 percent similar to SEQ ID NO:8. As used herein, SEQ ID NO:8 corresponds to the amino acid sequence encoded by the eIF4E-DEMP gene (described, infra).

Another suitable nucleic acid molecule for use in the methods of the present invention can be one that encodes an amino acid sequence that is at least 85 percent similar to a non-mutant translation initiation factor eIF4E of SEQ ID NO:2 and containing at least one substitution of at least one amino acid residue of SEQ ID NO:2 suitable substitutions can included, for example, T51A, P66T, V67E, K71R, L79R, G107P, and/or D109R. As used herein, SEQ ID NO:2 corresponds to the amino acid sequence encoded by the eIF4E-687 gene (described, infra).

In one embodiment of the method of imparting virus resistance to plants, a suitable nucleic acid molecule can include an antisense oligonucleotide complementary to a messenger RNA encoding the translation initiation factor eIF4E. Another suitable nucleic acid molecule can include a sense oligonucleotide homologous to a messenger RNA encoding the translation initiation factor eIF4E. Yet another suitable nucleic acid molecule can include one that mediates RNA interference ("RNAi") of the gene encoding the translation initiation factor eIF4E or that mediates RNAi of a transcript of the gene. These aspects are further described herein, infra.

The present invention also relates to a method of imparting virus resistance to plants by providing a nucleic acid molecule encoding a heterologous translation initiation factor eIF4E. A plant is transformed with the nucleic acid molecule under conditions effective to yield a transgenic plant that overexpresses the heterologous translation initiation factor eIF4E. In one embodiment, the nucleic acid molecule is in sense orientation. In one aspect of this method, the overexpressed heterologous translation initiation factor eIF4E causes positive interference with a plant virus. Suitable mechanisms for such positive interference includes, without limitation, inhibiting viral VPg to bind to eIF4E in the plant, as well as inhibiting mRNA cap-binding by eIF4E. Suitable heterologous translation initiation factor eIF4Es are as described herein. The present invention also relates to transgenic plants produced by this method, as well as component parts, seeds, and fruits of the transgenic plant.

The use of antisense oligonucleotides (e.g., RNA) to downregulate the expression of specific plant genes is well known (van der Krol et al., *Nature* 333:866-869 (1988) and Smith et al., *Nature* 334:724-726 (1988), which are hereby incorporated by reference in its entirety). Antisense nucleic acids are DNA or RNA molecules that are complementary to at least a portion of a specific mRNA molecule (Weintraub, "Antisense RNA and DNA," *Scientific American* 262:40 (1990), which is hereby incorporated by reference in its entirety). Antisense methodology takes advantage of the fact that nucleic acids tend to pair with "complementary" sequences. By complementary, it is meant that polynucleotides are capable of base-pairing according to the standard Watson-Crick rules. For example, in a target cell, the antisense nucleic acids hybridize to a target nucleic acid and interfere with transcription, and/or RNA processing, transport, translation, and/or stability. The overall effect of such interference with the target nucleic acid function is the disruption of protein expression.

Accordingly, both antisense and sense forms of the nucleic acids of the present invention are suitable for use in the DNA constructs of the invention. A single construct may contain both sense and antisense forms of one or more of the nucleic acid molecules of the present invention.

Alternatively, a DNA construct can be configured so that the DNA molecule encodes a mRNA which is not translatable, i.e., does not result in the production of a protein or polypeptide. This is achieved, for example, by introducing into the desired nucleic acid molecule sequence of the present invention one or more premature stop codons, adding one or more bases (except multiples of 3 bases) to displace the reading frame, and removing the translation initiation codon (U.S. Pat. No. 5,583,021 to Dougherty et al., which is hereby incorporated by reference in its entirety). This can involve the use of a primer to which a stop codon, such as TAATGA, is inserted into the sense (or "forward") PCR-primer for amplification of the full nucleic acid, between the 5' end of that primer, which corresponds to the appropriate restriction enzyme site of the vector into which the nucleic acid is to be inserted, and the 3' end of the primer, which corresponds to the 5' sequence of the enzyme-encoding nucleic acid.

Genes can be effective as silencers in the non-translatable antisense forms, as well as in the non-translatable sense form (Baulcombe, D. C., "Mechanisms of Pathogen-Derived Resistance to Viruses in Transgenic Plants," *Plant Cell* 8:1833-44 (1996); Dougherty, W. G., et al., "Transgenes and Gene Suppression: Telling us Something New?," *Current Opinion in Cell Biology* 7:399-05 (1995); and Lomonossoff, G. P., "Pathogen-Derived Resistance to Plant Viruses," *Ann. Rev. Phytopathol.* 33:323-43 (1995), which are hereby incorporated by reference in their entirety). Accordingly, one aspect of the present invention involves DNA constructs which contain one or more of the nucleic acid molecules of the present invention as a DNA which encodes a non-translatable mRNA, that nucleic acid molecule being inserted into the construct in either the sense or antisense orientation.

Numerous reports have been published on critical advances in the understanding of the biochemistry and genetics of both gene silencing and RNA-interference. Similarities between RNA-interference ("RNAi") and post-transcriptional gene silencing are astonishing, and point all to the crucial role played by sequence homology in triggering these two mechanistically related phenomena (Matzke et al., "RNA-Based Silencing Strategies in Plants," *Curr. Opin. Genet. Dev.* 11(2):221-227 (2001), which is hereby incorporated by reference in its entirety). In RNAi, the introduction of double stranded RNA ("dsRNA") into animal or plant cells leads to the destruction of the endogenous, homologous mRNA, phenocopying a null mutant for that specific gene. In both post-transcriptional gene silencing and RNAi, the dsRNA is processed to short interfering molecules of 21-, 22- or 23-nucleotide RNAs ("siRNA") by a putative RNAaseIII-like enzyme (Tuschl T., "RNA Interference and Small Interfering RNAs," *Chembiochem* 2: 239-245 (2001); and Zamore et al., "RNAi: Double Stranded RNA Directs the ATP-Dependent Cleavage of mRNA at 21 to 23 Nucleotide Intervals," *Cell* 101, 25-3, (2000), which are hereby incorporated by reference in their entirety). The endogenously generated siRNAs mediate and direct the specific degradation of the target mRNA. In the case of RNAi the cleavage site in the mRNA molecule targeted for degradation is located near the center of the region covered by the siRNA (Elbashir et al., "RNA Interference is Mediated by 21- and 22-Nucleotide RNAs," *Gene Dev.* 15(2):188-200 (2001), which is hereby incorporated by reference in its entirety). Thus, nucleic acid molecules of the present invention that mediate RNAi can be used in the present invention's method of imparting virus resistance to plants.

Another embodiment of the method of imparting virus resistance to plants involves providing a genetic construct containing the nucleic acid molecule of the present invention. The genetic construct is then used to transform a plant cell. In another embodiment, this method further involves propagating plants from the transformed plant cell. A suitable genetic construct for use in this method can further include a plant promoter and a terminator, where the plant promoter and the terminator are operatively coupled to the nucleic acid molecule. In one embodiment, the genetic construct is in an expression vector. As described in more detail, infra, transformation can be carried out by, without limitation, *Agrobacterium*-mediated transformation, biolistic transformation, and/or electroporation. Further, suitable techniques for the above aspects of the present invention's method of imparting virus resistance to plants is described in more detail, infra.

The present invention also relates to a genetic construct containing a nucleic acid molecule of the present invention. The genetic construct further contains a plant promoter heterologous to the nucleic acid molecule. The geneic construct also contains a terminator. The plant promoter and the terminator are operatively coupled to the nucleic acid molecule. The present invention further relates to an expression system containing the genetic construct and a host cell transformed with the genetic construct. In one embodiment, the nucleic acid molecule is in proper sense orientation. In another particular embodiment, the host cell can be, without limitation, a plant cell or a bacterial cell. Further detail regarding the genetic construct, expression system, and host cells of the present invention are described herein, infra.

The present invention also relates to a plant transformed with a genetic construct that contains: (i) a nucleic acid molecule which silences a gene encoding a translation initiation factor eIF4E in a plant; (ii) a plant promoter, and (iii) a terminator. The plant promoter and the terminator are operatively coupled to the nucleic acid molecule. Further, either the nucleic acid molecule, the plant promoter, or the terminator are heterologous to the transformed plant. The present invention further relates to component parts of, fruits of, and plant seeds produced from the transformed plant.

The present invention also relates to a plant seed transformed with a genetic construct containing: (i) a nucleic acid molecule which silences a gene encoding a translation initiation factor eIF4E in a plant; (ii) a plant promoter; and (iii) a terminator. The plant promoter and the terminator are operatively coupled to the nucleic acid molecule. Further, either the nucleic acid molecule, the plant promoter, or the terminator are heterologous to the transformed plant seed.

The present invention relates to an isolated nucleic acid molecule encoding a mutant translation initiation factor eIF4E that is effective in imparting virus resistance in plants. The present invention also relates to an isolated mutant translation initiation factor eIF4E encoded by the isolated nucleic acid molecule. The present invention further relates to a recombinant expression system and a host cell containing the isolated nucleic molecule, as well as a transgenic plant and a transgenic plant seed transformed with the isolated nucleic acid molecule. This isolated nucleic acid molecule can be used in the present invention's method of imparting virus resistance to plants, as previously described. In one embodiment of the recombinant expression system of the present invention, the isolated nucleic acid molecule is in sense orientation relative to a promoter.

In one embodiment, the nucleic acid molecule of the present invention encodes a mutant translation initiation factor eIF4E having an amino acid sequence of SEQ ID NO:4 and variants thereof that are at least 95 percent similar to SEQ ID NO:4. SEQ ID NO:4 is the amino acid sequence of the eIF4E-234 mutant translation initiation factor eIF4E (from *Capsicum chinense* PI 159234) (NCBI Accession No. AAR23918), as follows:

```
  1 mataemektt tfdeaekvkl naneaddeve egeiveetdd ttsylskeia akhplehswt
 61 fwfdntvaks rqaawgsslr nvytfstved fwgaynnihh psklvvradl hcfkhkiepk
121 wedpvcangg twkmsfskgk sdtswlytll amighqfdhe deicgavvsv rgkgekislw
181 tknaanetaq vsigkqwkqf ldysdsvgfi fhddakrldr naknrytv
```

SEQ ID NO:4 is encoded by the eIF4E-234 nucleotide sequence of SEQ ID NO:3 (from *Capsicum chinense* PI 159234) (NCBI Accession No. AY485129), as follows:

```
  1 atggcaacag ctgaaatgga gaaaacgacg acgtttgatg aagctgagaa ggtgaaattg
 61 aatgctaatg aggcagatga tgaagttgaa gaaggtgaaa ttgttgaaga aactgatgat
121 acgacgtcgt atttgagcaa agaaatagca gcaaagcatc cattagagca ttcatggact
181 ttctggtttg ataatacagt ggcgaaatcg agacaagctg cttggggtag ctcgcttcgc
241 aacgtctaca ctttctccac tgttgaagat ttttggggtg cttacaataa tatccaccac
301 ccaagcaagt tagttgtgag agcagactta cattgtttca agcataaaat tgagccaaag
361 tgggaagatc ctgtatgtgc caatggaggg acatggaaaa tgagttttc aaagggtaaa
421 tctgatacca gctggctata tacgctgctt gcaatgattg gacatcaatt cgatcatgaa
481 gatgaaattt gtggagcagt agttagtgtc agaggtaagg gagaaaaaat atctttgtgg
541 accaagaatg ctgcaaatga aacggctcag gttagcattg gtaagcaatg gaagcagttt
601 ctggattaca gcgacagtgt tggcttcata tttcacgacg atgcaaagag gctcgacaga
661 aatgcaaaga atcgttacac cgtatag
```

In another embodiment, the nucleic acid molecule of the present invention encodes a mutant translation initiation factor eIF4E having an amino acid sequence of SEQ ID NO:6 and variants thereof that are at least 95 percent similar to SEQ ID NO:6. SEQ ID NO:6 is the amino acid sequence of the eIF4E-YY mutant translation initiation factor eIF4E (from *Capsicum annuum* 'Yolo Y') (NCBI Accession No. AAR23919), as follows:

```
  1 mataemektt tfdeaekvkl naneaddeve egeiveetdd ttsylskeia tkhplehswt
 61 fwfdnpeaks kqaawgssrr nvytfstved fwgaynnihh psklvvgadl hcfkhkiepk
121 wedpvcangg twkmsfskgk sdtswlytll amighqfdhe deicgavvsv rgkgekislw
181 tknaanetaq vsigkqwkqf ldysdsvgfi fhddakrldr naknrytv
```

SEQ ID NO:6 is encoded by the eIF4E-YY nucleotide sequence of SEQ ID NO:5 (from *Capsicum annuum* 'Yolo Y') (NCBI Accession No. AY485130), as follows:

```
  1 atggcaacag ctgaaatgga gaaaacgacg acgtttgatg aagctgagaa ggtgaaattg
 61 aatgctaatg aggcagatga tgaagttgaa gaaggtgaaa ttgttgaaga aactgatgat
121 acgacgtcgt atttgagcaa agaaatagca acaaagcatc cattagagca ttcatggact
181 ttctggtttg ataatccaga ggcgaaatcg aaacaagctg cttggggtag ctcgcgtcgc
241 aacgtctaca ctttctccac tgttgaagat ttttgggtg cttacaataa tatccaccac
301 ccaagcaagt tagttgtggg agcagactta cattgtttca agcataaaat tgagccaaag
361 tgggaagatc ctgtatgtgc caatggaggg acatggaaaa tgagtttttc aaagggtaaa
421 tctgatacca gctggctata tacgctgctt gcaatgattg gacatcaatt cgatcatgaa
481 gatgaaattt gtggagcagt agttagtgtc agaggtaagg gagaaaaaat atctttgtgg
541 accaagaatg ctgcaaatga aacggctcag gttagcattg gtaagcaatg gaagcagttt
601 ctggattaca gcgacagtgt tggcttcata tttcacgacg atgcaaagag gctcgacaga
661 aatgcaaaga atcgttacac cgtatag
```

In another embodiment, the nucleic acid molecule of the present invention encodes a mutant translation initiation factor eIF4E having an amino acid sequence of SEQ ID NO:8 and variants thereof that are at least 95 percent similar to SEQ ID NO:8. As referred to herein, SEQ ID NO:8 is the amino acid sequence of the eIF4E-DEMP mutant translation initiation factor eIF4E (from *Capsicum annuum* 'Dempsey') (NCBI Accession No. AAR23920), as follows:

```
  1 mataemektt tfdeaekvkl naneaddeve egeiveetdd ttsylskeia tkhplehswt
 61 fwfdnpeaks kqaawgssrr nvytfstved fwgaynnihh psklvvganl hcfkhkiepk
121 wedpvcangg twkmsfskgk sdtswlytll amighqfdhe deicgavvsv rgkgekislw
181 tknaanetaq vsigkqwkqf ldysdsvgfi fhddakrldr naknrytv
```

SEQ ID NO:8 is encoded by the eIF4E-DEMP nucleotide sequence of SEQ ID NO:7 (from *Capsicum annuum* 'Dempsey') (NCBI Accession No. AY485131), as follows:

```
  1 atggcaacag ctgaaatgga gaaaacgacg acgtttgatg aagctgagaa ggtgaaattg 61 aatgctaatg aggcagatga tgaagttgaa gaaggtgaaa ttgttgaaga aactgatgat 121 acgacgtcgt atttgagcaa agaaatagca acaaagcatc cattagagca ttcatggact 181 ttctggtttg ataatccaga ggcgaaatcg aaacaagctg cttggggtag ctcgcgtcgc 241 aacgtctaca ctttctccac tgttgaagat ttttggggtg cttacaataa tatccaccac 301 ccaagcaagt tagttgtggg agcaaactta cattgtttca agcataaaat tgagccaaag 361 tgggaagatc ctgtatgtgc caatggaggg acatggaaaa tgagtttttc aaagggtaaa 421 tctgatacca gctggctata cgctgcttgc aatgattgga catcaattcg atcatgaa 481 gatgaaattt gtggagcagt agttagtgtc agaggtaagg gagaaaaaat atctttgtgg 541 accaagaatg ctgcaaatga aacggctcag gttagcattg gtaagcaatg gaagcagttt 601 ctggattaca gcgacagtgt tggcttcata tttcacgacg atgcaaagag gctcgacaga 661 aatgccaaga atcgttacac cgtatag
```

In another embodiment, the nucleic acid molecule encodes a mutant translation initiation factor eIF4E having an amino acid sequence that is at least 85 percent similar to a non-mutant translation initiation factor eIF4E of SEQ ID NO:2. In this embodiment, the mutant translation initiation factor eIF4E contains at least one substitution of at least one amino acid residue of SEQ ID NO:2. Suitable substitutions can include, for example, T51A, P66T, V67E, K71R, L79R, G107P, and/or D109R. As referred to herein, SEQ ID NO:2 is the amino acid sequence of the eIF4E-687 translation initiation factor eIF4E (*Capsicum annuum* 'Yolo Wonder') (NCBI Accession No. AAM82190), as follows:

```
  1 mataemektt tfdeaekvkl naneaddeve egeiveetdd ttsylskeia tkhplehswt 61 fwfdnpvaka kqaawgsslr nvytfstved fwgaynnihh psklvvgadl hcfkhkiepk 121 wedpvcangg twkmsfskgk sdtswlytll amighqfdhe deicgavvsv rgkgekislw 181 tknaanetaq vsigkqwkqf ldysdsvgfi fhddakrldr naknrytv
```

SEQ ID NO:2 is encoded by the eIF4E-687 nucleotide sequence of SEQ ID NO:1 (from *Capsicum annuum* 'Yolo Wonder') (NCBI Accession No. AY122052), as follows:

```
  1 aaagtaaaaa aagcacacag caccaacaat ggcaacagct gaaatggaga aaacgacgac 61 gtttgatgaa gctgagaagg tgaaattgaa tgctaatgag gcagatgatg aagttgaaga 121 aggtgaaatt gttgaagaaa ctgatgatac gacgtcgtat ttgagcaaag aaatagcaac 181 aaagcatcca ttagagcatt catggacttt ctggtttgat aatccagtgg cgaaatcgaa 241 acaagctgct gggggtagct cgcttcgcaa cgtctacact ttctccactg ttgaagattt 301 ttggggtgct tacaataata tccaccaccc aagcaagtta gttgtgggag cagacttaca 361 ttgtttcaag cataaaattg agccaaagtg gaagatcct gtatgtgcca atggagggac 421 atggaaaatg agttttcaa agggtaaatc tgataccagc tggctatata cgctgcttgc 481 aatgattgga catcaattcg atcatgaaga tgaaatttgt ggagcagtag ttagtgtcag 541 aggtaaggga gaaaaatat ctttgtggac caagaatgct gcaaatgaaa cggctcaggt 601 tagcattggt aagcaatgga agcagtttct ggattacagc gacagtgttg gcttcatatt 661 tcacgacgat gcaaagaggc tcgacagaaa tgcaaagaat cgttacacag tataattctt 721 gatgcaatgt cggaatataa gaaacacaat tcgtactgaa aagttgtagg cactagttta 781 gtttctcata cgataaagct tctggtttga gtaccttgtg tattggtgtt tgcactttct 841 aatcgcgtaa aattgtccgg ttttggattc aaaaa
```

The isolated nucleic acid molecule of the present invention can be from various plant sources, including, without limitation, from *Capsicum* spp. or *Arabidopsis* spp.

The present invention also relates to a method of making a mutant translation initiation factor eIF4E. This method involves growing a host cell containing an isolated nucleic acid molecule encoding a mutant translation initiation factor eIF4E of the present invention under conditions whereby the host cell expresses the mutant translation initiation factor eIF4E. The mutant translation initiation factor eIF4E is then isolated. Further detail regarding this method is provided herein, infra.

The present invention also relates to a method of making a transgenic plant having enhanced virus resistance compared to that of a non-transgenic plant. This method involves transforming a non-transgenic plant cell with a nucleic acid molecule encoding a mutant translation initiation factor eIF4E of the present invention under conditions effective to yield a transgenic plant cell having enhanced virus resistance compared to that of a non-transgenic plant. A transgenic plant is regenerated from the transformed plant cell. The present invention further relates to a transgenic plant and plant seed produced by this method. Further detail on this aspect of the invention is provided infra.

The present invention also relates to an isolated mutant translation initiation factor eIF4E encoded by the corresponding nucleic acid molecule of the present invention (described, supra). The isolated mutant translation initiation factor eIF4E can be recombinant. The isolated mutant translation initiation factor eIF4E can also be in pure or non-pure form. A purified protein or polypeptide of the mutant translation initiation factor eIF4E of the present invention can be obtained by several methods. The purified protein or polypeptide of the mutant translation initiation factor eIF4E of the present invention is preferably produced in pure form (preferably at least about 80%, more preferably 90% pure) by conventional techniques well known in the art. Typically, the purified protein or polypeptide of the mutant translation initiation factor eIF4E of the present invention is secreted into the growth medium of recombinant host cells. Alternatively, the purified protein or polypeptide of the mutant translation initiation factor eIF4E of the present invention is produced but not secreted into growth medium. In such cases, to isolate the protein or polypeptide of the mutant translation initiation factor eIF4E, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the protein or polypeptide of the mutant translation initiation factor eIF4E of the present invention is subjected to gel filtration in an appropriately sized dextran or polyacrylamide column to separate the proteins. If necessary, the protein fraction (containing the mutant translation initiation factor eIF4E of the present invention) can be further purified by high performance liquid chromatography ("HPLC").

As previously discussed, the present invention also relates to a recombinant expression system that contains the various nucleic acid molecules of the present invention. This can involve incorporating the nucleic acid molecules of the present invention into host cells using conventional recombinant DNA technology. Generally, this involves inserting the nucleic acid molecule into an expression system to which the nucleic acid molecule is heterologous (i.e., not normally present). The heterologous nucleic acid molecule is inserted into the expression system which includes the necessary elements for the transcription and translation of the inserted protein coding sequences. In one embodiment, the expression system of the present invention contains the nucleic acid molecule of the present invention in proper sense orientation relative to a promoter.

The nucleic acid molecules of the present invention can be inserted into any of the many available expression vectors and cell systems using reagents that are well known in the art. Suitable vectors include, but are not limited to, the following viral vectors such as lambda vector system gt11, gt WES.tB, Charon 4, and plasmid vectors such as pBR322, pBR325, pACYC177, pACYC1084, pUC8, pUC9, pUC18, pUC19, pLG339, pR290, pKC37, pKC101, SV 40, pBluescript II SK+/- or KS+/- (see "Stratagene Cloning Systems" Catalog (1993) from Stratagene, La Jolla, Calif., which is hereby incorporated by reference in its entirety), pQE, pIH821, pGEX, pET series (see Studier et al., "Use of T7 RNA Polymerase to Direct Expression of Cloned Genes," *Gene Expression Technology* vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual,* 2nd Edition, Cold Spring Harbor, N.Y., Cold Spring Harbor Laboratory Press (1989); and Ausubel et al., *Current Protocols in Molecular Biology*, John Wiley & Sons, New York, N.Y., (1989) which are hereby incorporated by reference in their entirety.

In preparing a DNA vector for expression, the various DNA sequences can normally be inserted or substituted into a bacterial plasmid. Any convenient plasmid can be employed, which will be characterized by having a bacterial replication system, a marker which allows for selection in a bacterium and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall are characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobac-*

*terium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Certain "control elements" or "regulatory sequences" are also incorporated into the vector-construct. These include non-translated regions of the vector, promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopoline synthase ("NOS") gene promoter, from *Agrobacterium tumefaciens* (U.S. Pat. No. 5,034,322 issued to Rogers et al., which is hereby incorporated by reference in its entirety), the cauliflower mosaic virus ("CaMV") 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter ("ubi"), which is the promoter of a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11: 605-612 (1997), and McNellis et al., "Glucocorticoid-Inducible Expression of a Bacterial Avirulence Gene in Transgenic *Arabidopsis* Induces Hypersensitive Cell Death, *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific promoters include seed, flower, or root specific promoters as are well known in the field (U.S. Pat. No. 5,750,385 issued to Shewmaker et al., which is hereby incorporated by reference in its entirety). In one embodiment of the present invention, a heterologous promoter is linked to the nucleic acid of the construct, where "heterologous promoter" is defined as a promoter to which the nucleic acid of the construct is not linked in nature.

The nucleic acid construct also includes an operable 3' regulatory region, selected from among those which are capable of providing correct transcription termination and polyadenylation of mRNA for expression in the host cell of choice, operably linked to a DNA molecule which encodes for a protein of choice. A number of 3' regulatory regions are known to be operable in plants. Exemplary 3' regulatory regions include, without limitation, the nopaline synthase ("nos") 3' regulatory region (Fraley et al., "Expression of Bacterial Genes in Plant Cells," *Proc. Nat'l Acad. Sci. USA,* 80:4803-4807 (1983), which is hereby incorporated by reference in its entirety) and the cauliflower mosaic virus ("CaMV") 3' regulatory region (Odell et al., "Identification of DNA Sequences Required for Activity of the Cauliflower Mosaic Virus 35S Promoter," *Nature* 313(6005):810-812 (1985), which is hereby incorporated by reference in its entirety). Virtually any 3' regulatory region known to be operable in plants would suffice for proper expression of the coding sequence of the nucleic acid of the present invention.

The vector of choice, suitable promoter, and an appropriate 3' regulatory region can be ligated together to produce the nucleic acid construct which contains the nucleic acid molecule of the present invention, or suitable fragments thereof, using well known molecular cloning techniques as described in Sambrook et al., *Molecular Cloning: A Laboratory Manual,* 2nd Edition, Cold Spring Harbor, N.Y., Cold Spring Harbor Laboratory Press (1989); Ausubel et al., *Current Protocols in Molecular Biology*, John Wiley & Sons, New York, N.Y. (1989), which are hereby incorporated by reference in their entirety.

Once the nucleic acid construct has been prepared, it is ready to be incorporated into a host cell. Basically, this method is carried out by transforming a host cell with the expression system of the present invention under conditions effective to yield transcription of the nucleic acid molecule in the host cell, using standard cloning procedures known in the art, such as described by Sambrook et al., *Molecular Cloning: A Laboratory Manual,* 2nd Edition, Cold Spring Harbor, N.Y., Cold Spring Harbor Laboratory Press, (1989), which is hereby incorporated by reference in its entirety. Suitable host cells include, but are not limited to, bacterial cells, fungal cells, viral cells, yeast cells, mammalian cells, insect cells, algal cells, plant cells, and the like. Methods of transformation may result in transient or stable expression of the DNA under control of the promoter.

As described, supra, another embodiment relates to a method of making a transgenic plant having enhanced virus resistance compared to that of a non-transgenic plant. Generally, this method involves transforming a non-transgenic plant cell with a nucleic acid molecule according to the present invention under conditions effective to yield a transgenic plant cell having enhanced virus resistance compared to that of a non-transgenic plant. The transformed plant cell is then regenerated into a transgenic plant. Thus, as mentioned, supra, in other embodiments, the present invention includes transgenic plants and seeds produced by transformation with the nucleic acid molecule of the present invention.

Further aspects of the method of making the transgenic plant of the present invention are described below.

In one embodiment, the isolated nucleic acid of the present invention is stably inserted into the genome of the recombinant plant cell as a result of the transformation, although transient expression can serve an important purpose, particularly when the plant under investigation is slow-growing. Plant tissue suitable for transformation include leaf tissue, root tissue, meristems, zygotic and somatic embryos, callus, protoplasts, tassels, pollen, embryos, anthers, and the like.

The means of transformation chosen is that most suited to the tissue to be transformed. An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign DNA into plant cells. Another approach to transforming plant cells involves particle bombardment (also known as biolistic transformation) of the host cell, as disclosed in U.S. Pat. Nos. 4,945,050, 5,036,006, and 5,100,792, all issued to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety. Yet another method of introduction is fusion of protoplasts with other entities, either minicells, cells, lysosomes or other fusible lipid-surfaced bodies (Fraley et al., *Proc. Natl. Acad. Sci. USA* 79:1859-63 (1982), which is hereby incorporated by reference in its entirety). The DNA molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures*, Vol. 1, MacMillan Publishing Co., NY (1983); and Vasil (ed.), *Cell Culture and Somatic Cell Genetics of Plants*, Acad. Press, Orlando, Vol. I, 1984, and Vol. III (1986), which are hereby incorporated by reference in their entirety.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley et al., "Expression of Bacterial Genes in Plant Cells," *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea, is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound, are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the transgene by Southern blot hybridization analysis, using a probe specific to the transgenes contained in the given cassette used for transformation (Sambrook et al., *Molecular Cloning: A Laboratory Manual*, Cold Spring Harbor, N.Y., Cold Spring Harbor Laboratory Press (1989), which is hereby incorporated by reference in its entirety).

After the expression cassette is stably incorporated in transgenic plants, it can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds or propagules (e.g., cuttings) are recovered from the transgenic plants. These seeds can then be planted in the soil and cultivated using conventional procedures to produce transgenic plants.

The methods and isolated nucleic acid molecules of the present invention can be used to impart virus resistance to plants against all types of plant viruses. In one embodiment, present invention is effective in imparting virus resistance to plants against viruses of the Potyviridae family. In particular, the methods and isolated nucleic acid molecules can be effective in imparting virus resistance to plants against Potyviridae viruses such as, without limitation, Lettuce Mosaic Virus ("LMV"), Pepper Mottle Virus ("PepMoV"), Potato Virus Y ("PVY"), Tobacco Etch Virus ("TEV"), and Turnip Mosaic Virus ("TuMV").

Examples of suitable plants, plant seeds, and/or plant cells that can be used in making or providing the transgenic plants, transgenic plant cells, and/or transgenic plant seeds of the present invention can include, without limitation, rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery carrot, squash, pumpkin, zucchini, cucumber, apple, pear, melon, strawberry, grape, raspberry, pineapple, soybean, tobacco, tomato, sorghum, sugarcane, banana, mung bean, alfalfa, rye, brussel sprout, beet, parsnip citrus, *Arabidopsis, Saintpaulia*, petunia, pelargonium, poinsettia, chrysanthemum, carnation, and/or zinnia.

EXAMPLES

Example 1

Recombinant Technology Used in Analyzing Recessive Plant Viral Resistance Due to Mutations in Translation Initiation Factor eIF4E DNA and RNA blotting techniques were done by standard procedures. Mapping was done according to (Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998), which is hereby incorporated by reference in its entirety).

Example 2

Primer Sequences and PCR Cycling Procedures Used in Analyzing Recessive Plant Viral Resistance Due to Mutations in Translation Initiation Factor eIF4E eIF4E-687 full-length ORF primers based on tomato eIF4E sequence (Genbank # AF259801) were as follows:

```
                                            (SEQ ID NO:9)
    Forward 5'-atggcaacagctgaaatgg-3'

(SEQ ID NO:10)
    Reverse 5'-tatacggtgtaacgattcttggca-3'
```

Pepper-specific sequence at the 5' and 3' ends were confirmed by RACE and PCR-Walking (Clontech, Palo Alto, Calif.).
PCR cycling conditions were as follows:
95° C. 3 min
(95° C. 30 sec, 55° C. 30 sec, 72° C. 5 mins)×1
(95° C. 30 sec, 55° C. 30 sec, 72° C. 90 sec)×29
72° C. 10 mins
Primers used to amplify the internal 321 bp genomic sequence spanning an intron containing the MseI CAPS differential cleavage site were based on conserved sequence motifs from Genbank eIF4E accessions, as follows:

```
                                           (SEQ ID NO:11)
    Forward 5'-aatatccatcacccaag-3'

(SEQ ID NO:12)
    Reverse 5'-gctccacatatttcatc-3'
```

PCR cycling conditions were as follows:
95° C. 3 min
(95° C. 30 sec, 50° C. 30 sec, 72° C. 5 min)×1
(95° C. 30 sec, 50° C. 30 sec, 72° C. 90 sec)×29
72° C. 10 min
Primers used to amplify the promoter region containing the SstI CAPS differential cleavage site were based on sequence obtained by PCR-Walking (Clontech, Palo Alto, Calif.). The reverse primer lies 56 bases within the eIF4E-687 open reading frame. The following are the primers used:

```
                                           (SEQ ID NO:13)
    Forward 5'-ttacacgcgccgatacacttg-3'

(SEQ ID NO:14)
    Reverse 5'-catcatctgccttcattagcattcaat-3'
```

PCR cycling conditions were as follows:
95° C. 3 min
(95° C. 30 sec, 60° C. 30 sec, 72° C. 5 min)×1
(95° C. 30 sec, 60° C. 30 sec, 72° C. 90 sec)×29
72° C. 10 min
Primers used to amplify eIF(iso)4E for mapping in pepper, as follows:

```
                                           (SEQ ID NO:15)
    Forward 5'-aacaatggccaccgaagc-3'

(SEQ ID NO:16)
    Reverse 5'-atttcacacagtatatcggctct-3'
```

PCR cycling conditions were as follows:
95° C. 3 min
(95° C. 30 sec, 55° C. 30 sec, 72° C. 5 min)×1
(95° C. 30 sec, 55° C. 30 sec, 72° C. 90 sec)×29
72° C. 10 min Example 3

Inoculation of Seedlings for Use in Virus Screening Procedures Used in Analyzing Recessive Plant Viral Resistance Due to Mutations in Translation Initiation Factor eIF4E The first two leaves of seedlings at the 4-6 leaf stage were rub-inoculated (using carborundum) with plant extract from TEV-HAT or PepMoV infected tobacco plants ground in ice-cold 0.05 M potassium phosphate buffer, pH 8. Systemic infection was assayed at 21 days post inoculation by visual symptoms and confirmed by indirect ELISA (Voller et al., "The Detection of Viruses by Enzyme-Linked Immunosorbent Assay (ELISA)," *Journal of General Virology* 33:165-167 (1976), which is hereby incorporated by reference in its entirety).

Example 4

Virus Screening Procedures Used in Analyzing Recessive Plant Viral Resistance Due to Mutations in Translation Initiation Factor eIF4E

*Agrobacterium*-mediated transient expression, Yeast two-hybrid analysis, and Cap-binding assays were used. *Agrobacterium*-mediated transient expression assays followed the method in (Van den Ackerveken et al., "Recognition of the Bacterial Avirulence Protein AvrBs3 Occurs Inside the Host Plant Cell," *Cell* 87:1307-16 (1996), which is hereby incorporated by reference in its entirety). Yeast two-hybrid procedures followed the method in (Golemis et al., "The Yeast Two-Hybrid System: Criteria for Detecting Physiologically Significant Protein-Protein Interactions," *Curr. Issues Mol.*

Biol. 1:31-45 (1999), which is hereby incorporated by reference in its entirety). Cap-binding assays followed the procedures in (Vasilescu et al., "Mutants of Eukaryotic Initiation Factor eIF-4E with Altered mRNA Cap Binding Specificity Reprogram mRNA Selection by Ribosomes in *Saccharomyces cerevisiae*," *J. Biol. Chem.* 271:7030-7 (1996), which is hereby incorporated by reference in its entirety).

Example 5

Figure 2:
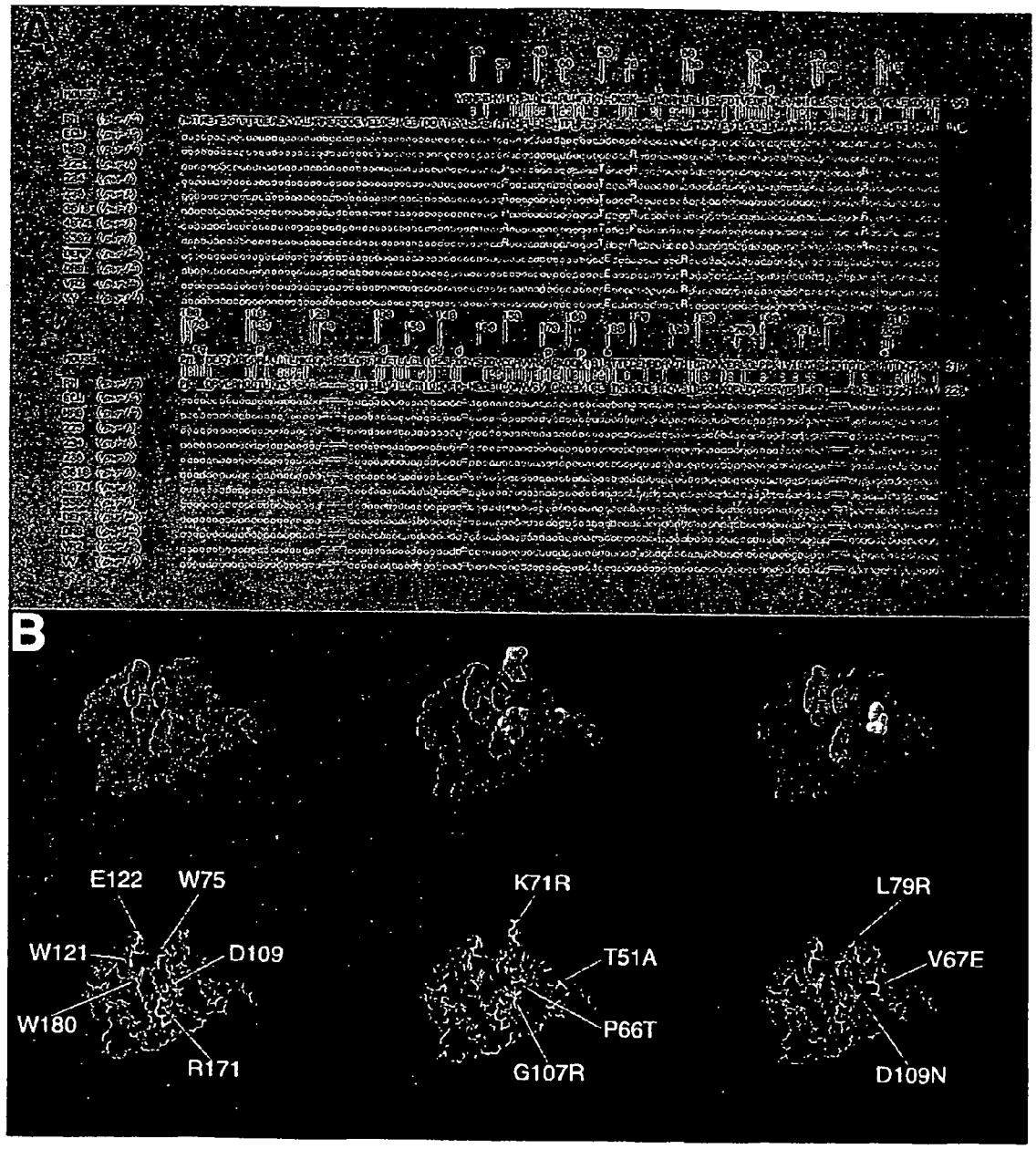

Amino Acid Substitutions Relating to the Analysis of Recessive Plant Viral Resistance Due to Mutations in Translation Initiation Factor eIF4E Amino acid alignments of eIF4E-687 (FIG. 2A) reveal identical sequences for three *C. chinense* accessions known to carry pvr1 and three pvr1/pvr1 *C. annuum* bell pepper breeding lines derived from a resistant *C. chinense* parent. Promoter sequences for the breeding lines also carry distinct sequence identical to the *C. chinense* accessions, further indicating an introgression event. There are four mutations relative to the consensus *C. annuum* susceptible sequence of RNaky and ECW. Three of the mutations change the amino acid group, while the K71R mutation is conservative (positively charged polar group) and is shared by the TEV and PepMoV susceptible *C. chinense* cultivar Habanero and may be a species-specific difference. T51R represents a shift from polar to nonpolar, P66T represents a shift from nonpolar to polar, and G107R represents a shift from nonpolar to positively charged polar amino acids. The combined effects of these amino acid substitutions are a conformational shift in the string of amino residues that flank the cap-binding slot of the protein (FIG. 2B). This can clearly be seen with the position of the K71R mutation. Though none of the amino acid positions mutated in the pvr1 mutant are strictly conserved for cap-binding, the G107R mutation could interrupt the salt bond stabilization of arginine 171 by aspartic acid 109, due to the introduction of another positively charged side-chain. There could also be steric hindrance based on the conformation of the G107R mutation in reference to how the cap needs to be stabilized by arginine 171. The T51A mutation in the "tail" of the protein (FIG. 2) may be involved in cap-binding also as mutations in human in histidine residues at corresponding position 48 abolished cap binding (Morino et al., "Analysis of the mRNA Cap-Binding Ability of Human Eukaryotic Initiation Factor-4E by Use of Recombinant Wild-Type and Mutant Forms," *Eur. J. Biochem.* 239:597-601 (1996), which is hereby incorporated by reference in its entirety).

The pvr2$^1$ and pvr2$^2$ sequences share two (V67E and L79R) out of their three mutations relative to *C. annuum* susceptible cultivars. The V67E mutation represents a shift from nonpolar to negatively charged polar and the L79R represents a shift from nonpolar to positively charged polar amino acids. Though the mutated residues are not directly involved in cap-binding, once again a conformation shift is seen along the string of amino acid residues flanking the cap-binding slot. Finally, the pvr2$^2$ mutant has a specific D109R mutation that directly affects a highly conserved residue required for cap-binding. The D109R mutation represents a shift from negatively charged polar to uncharged polar residues. This would interrupt the salt bond D109 ordinarily makes with negatively charged R171 to stabilize its position for cap-binding function.

Looking at the overall combination of point mutations, the pvr1 G107R mutation and pvr2$^2$ D109R mutations within the cap-binding slot may have similar effects on cap-binding, and result in their commonly held resistance to TEV-HAT and PVY-1. Conformational differences resulting from the two unique mutations in each in the region flanking the cap-binding slot allele (P66T and K71R in pvr1 and V67E and L79R in pvr2$^2$) may have similar consequences for resistance to PVY-0. Finally, the combined effects in pvr1 of the T51A mutation in addition to the other three mutations may serve to extend the resistance spectrum to PepMoV and PVY-1, 2 resistance. Mechanistically, pvr1 and pvr2-2 appear to share a common mechanism with regard to resistance to TEV-HAT (replication), and it is unknown whether all three alleles also share a common mechanism for resistance to PVY-0 (cell-to-cell movement).

Example 6

Data Demonstrating that the Silencing of eIF4E Results in Resistance to Plant Viruses This experiment demonstrates that when a copy of the eukaryotic translation initiation factor, eIF4E, is expressed in a susceptible plant such that the plant's own copy of the gene is silenced, that plant is then less susceptible or not susceptible to viral infection. This experiment shows the effect when the gene is expressed transiently, but the same effect could be created using other stable silencing methods such as RNAi.

For transient expression assays, one homolog of the gene eIF4E from *Capsicum annuum* RNaky (susceptible to tobacco etch virus) (Potyviridae) was cloned into pPVX201 provided by D. Baulcombe. The 687-bp coding region gene was amplified using the primers 5'-ATCGATGGCAACAGCTGAAATGG-3' (SEQ ID NO:17) (introduced ClaI site is underlined) and 5'-CTATACG-GTCTAACGATTCT-3' (SEQ ID NO:18). Amplified fragments were cloned into pGEM$^T$ (Promega, Madison, Wis.) and confirmed by sequencing. Products were digested with ClaI and SalI and subcloned into corresponding vector sites. The resulting pPVX201 derivatives were designated pPVX201::eIF4E-RN. A derivative of pPVX201 carrying no insert was used as a control. To increase inoculum prior to experiments, each leaf of 4-6 week old *N. benthamiana* seedlings was mechanically inoculated with ≧50 ug of plasmid in a 15% bentonite suspension in 43 mM sodium phosphate buffer (pH 7.0). Systemically infected *N. benthamiana* plants inoculated with pPVX::eIF4E-RN or pPVX201 developed chlorosis and systemic mosaic 14 days post-inoculation (dpi). To prepare inoculum for *Capsicum* seedlings, non-necrotic symptomatic *N. benthamiana* leaves 10-14 dpi were homogenized in 50 mM phosphate buffer (pH 7.0).

Six to eight week old seedlings of four pepper genotypes previously determined to be susceptible to PVX, *C. chinense* PI159234 (resistant to TEV) and *C. annuum* ECW were mechanically inoculated with one of the two constructs above, one containing eIF4E, one not. Infection was confirmed by positive indirect enzyme-linked immunosorbent assay (ELISA) and hybridization analysis. Three weeks after PVX inoculation which introduced the gene used to silence eIF4E, crude extract from the test virus, TEV-HAT from infected tobacco KY14 ground in 0.05 M potassium phosphate, was rub-inoculated on upper leaves which didn't show any symptom.

Both genotype, PI159234 and ECW, infected with pPVX201 showed typical PVX symptoms (mottling, chlorosis, distortion and spreading necrosis on inoculated leaves) that moved systemically throughout the plant. When inoculated with pPVX::eIF4E-RN, the vector carrying the silencing construct, *C. chinense* PI159234 plants developed HR like necrotic response 10 days after inoculation and symptoms did not spread systemically. Occasionally (1 out of 10 plants in a typical experiment) an individual plant showed systemic infection but symptoms were usually milder than wild type PVX symptom. In contrast, C. annuum ECW inoculated with the same virus didn't show any necrotic response on inoculated leaves and showed mottling, chlorosis, and rarely necrosis, and the symptom spread systemically but very slowly.

Figure 1:
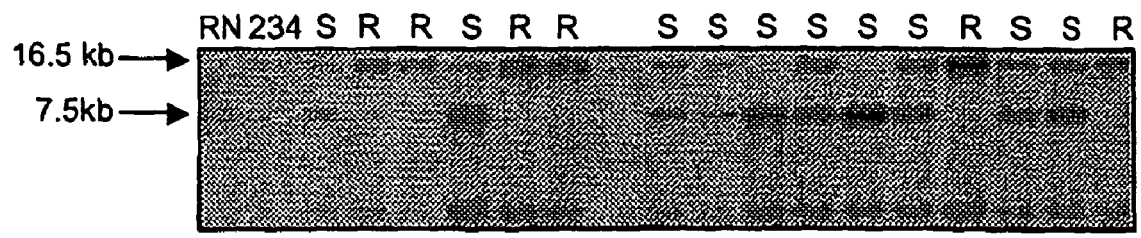
FIGS. 1A-1C demonstrate that eIF4E-687 colocalizes with pvr1.
Figure 1:
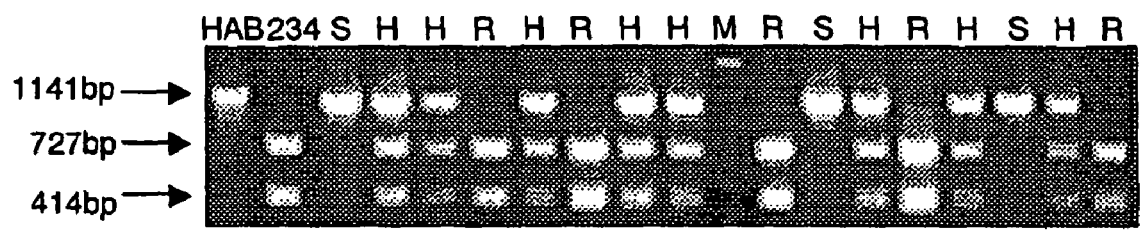
Figure 1:
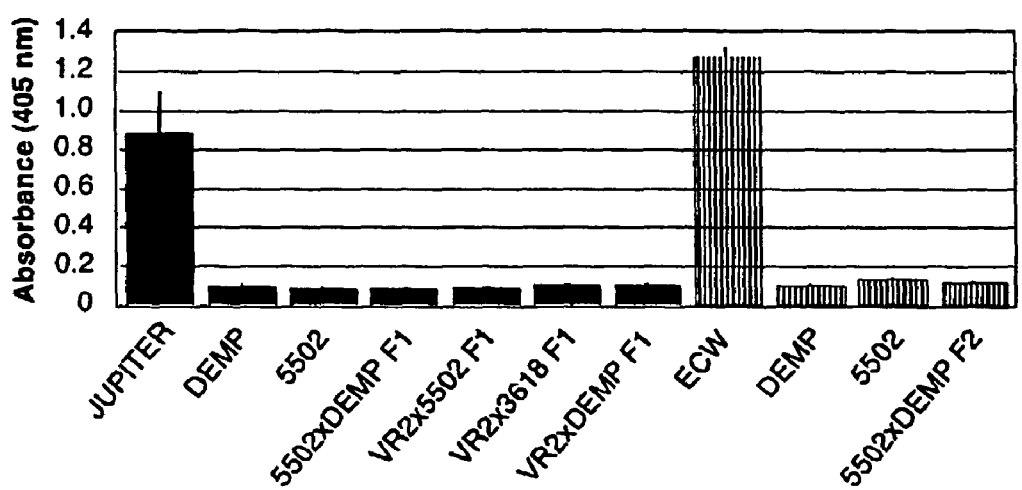

It is assumed that the reduced symptoms of the plants inoculated by the PVX expression eIF4E-RN were affected by the gene silencing of eIF4E. Therefore, tests were performed to determine whether the pPVXeIF4E-RN infected C. annuum ECW plants, a pepper variety known to be extremely susceptible to the TEV, can support TEV virus replication after inoculation PVX expressing eIF4E-RN.

To test this, the TEV-susceptible genotype previously inoculated with either pPVX201 (lacking the gene) or pPVXeIF4E-RN was challenged. Two weeks after TEV inoculation, upper leaves of the infected plants were collected and tested for virus accumulation by ELISA. ELISA analysis showed significant difference in TEV accumulation between the plants infected with pPVX201 and pPVXeIF4E-RN, 1.5+/−1.0 and 0.6+/−0.27 respectively.

Plants inoculated with the construct lacking eIF4E were infected while plants inoculated with the silencing construct were not. These data establish that viral symptoms apparent at the whole plant level and virus replication/accumulation in plant tissue can be reduced or eliminated by expressing a construct that silences eIF4E in plants.

Example 7

Data Demonstrating that the Transgenic Silencing of the Plant Gene eIF4E Results in Stable Heritable Resistance to Plant Viruses It was demonstrated that when a copy of the eukaryotic translation initiation factor, eIF4E, is expressed in a susceptible plant such that the plant's own copy of the gene is silenced, that plant is then less susceptible or not susceptible to viral infection. This experiment demonstrated the concept that stable silencing of a plant gene can result in resistance to a plant pathogen. This is believed to be the first demonstration of this concept. Preliminary evidence suggests that silencing eIF4E will result in resistance to at least 3 viruses and perhaps more, and also that silencing a related gene eIF(iso)4E should also result in virus resistance. Silencing other host translation factors, eIF4G, eIF4F and their isoforms will likely also have an effect.

Constructs that express the eukaryotic translation factor, eIF4E, in an anti-sense orientation were transformed into a tomato susceptible to the plant potyvirus, tomato etch virus. Control treatments included untransformed tomatoes and tomatoes of the same genotype transformed with an empty vector. The resulting transformants, the T0 generation, were analyzed for presence of the respective transgene and degree of eIF4E silencing reflected by reduced levels of eIF4E mRNA. T0 plants were selected that showed strong silencing of this gene and were self-pollinated to generate R1 progenies. These progenies should be segregating for the transgene and therefore for resistance to the virus, if the silencing results in plant-level virus resistance.

These progenies were inoculated with the virus TEV and symptoms were allowed to develop. The titer of the virus in tomato tissue was then analyzed in each plant using the assay, enzyme-linked immunosorbent assay (ELISA), which quantifies presence of the viral coat protein, using an antibody that specifically recognizes this protein. In T1 generation progenies produced by T0 plants showing the strongest silencing (see FIG. 1) segregating for presence of the transgene resulted in plants showing no symptoms of the disease, in contrast to positive controls (untransformed, transformed with empty vector or irrelevant gene) and plants that did not carry the transgene (FIG. 2). When these plants were analyzed quantitatively using ELISA, symptomless plants that carried the transgene showed low ELISA values, equivalent to negative controls, while symptomatic plants showed high ELISA values, equivalent to positive controls (Table 1). This experiment proves that by silencing a host gene transgenically, stable heritable plant disease resistance can be engineered.

It is believed that this is the first demonstration of this principal in plants. This knowledge should allow one to engineer a broad spectrum resistant response to a wide array of pathogens. These progenies are being tested further for additional viruses and the progenies of resistant plants will also be tested to confirm resistance in the T2 generation.

Example 8

Recessive Plant Viral Resistance Results from Mutations in Translation Initiation Factor eIF4E Three widely used recessive *Capsicum* alleles, pvr1, $pvr2^1$ and $pvr2^2$ confer resistance to three Potyvirus species, potato virus Y (PVY), pepper mottle virus (PepMoV) and tobacco etch virus (TEV). The allele pvr1 confers resistance to PVY, PepMoV and most TEV isolates; $pvr2^1$ confers resistance to PVY-0 and is allelic for this resistance with $pvr2^2$, which also controls additional PVY and TEV isolates. Both pvr1 and $pvr2^2$ share a common resistance mechanism (blocked replication) to at least one TEV isolate, TEV-HAT (Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998); and Deom et al., "Resistance to Tobacco Etch Virus in *Capsicum annuum*: Inhibition of Virus RNA Accumulation," *Mol. Plant Microbe Interact.* 10:917-921 (1997), which are hereby incorporated by reference in their entirety); pvr2' blocks cell-to-cell movement of PVY-0 (Arroyo et al., "Impaired Cell-to-Cell Movement of Potato Virus Y in Pepper Plants Carrying the Y-A (pr2-1) Resistance Gene," *Mol. Plant Microbe Interact.* 9:314-318 (1996), which is hereby incorporated by reference in its entirety). Although the viral avirulence determinants in this system remain unknown, the central region of the viral VPg protein has been identified as an avirulence determinant in nearly every recessive potyvirus resistance system studied to date (Rajamaki et al., "Viral Genome-Linked Protein (VPg) Controls Accumulation and Phloem-Loading of a Potyvirus in Inoculated Potato Leaves," *Mol. Plant Microbe Interact.* 15:138-49 (2002), which is hereby incorporated by reference in its entirety). The host translation factors eIF4E and eIF(iso)4E have shown strong in vitro interaction with VPg that in *Arabidopsis* have been correlated with viral infectivity (Leonard et al., "Complex Formation Between Potyvirus VPg and Translation Eukaryotic Initiation Factor 4E Correlates with Virus Infectivity," *J. Virol.* 74:7730-7 (2000); and Schaad et al., "Strain-Specific Interaction of the Tobacco Etch Virus NIa Protein with the Translation Initiation Factor eIF4E in the Yeast Two-Hybrid System," *Virology* 273:300-6 (2000), which are hereby incorporated by reference in their entirety); therefore, these genes were considered candidates for the pvr loci.

A hybridization probe specific to the 687 bp eIF4E sequence (eIF4E-687) (see Examples 1-5, supra) identified an RFLP that mapped precisely to pvr1 (Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998), which is hereby incorporated by reference in its entirety) (FIG. 1A). Sequence-based CAPS markers confirmed this result (FIG. 1B) (see Examples 1-5, supra). Pepper eIF(iso)4E (see Examples 1-5, supra) was unlinked to pvr1, localizing instead to a chromosomal interval containing the recessive resistance gene, pvr6, reported to act in tandem with $pvr2^2$ to confer resistance to chili veinal mottle potyvirus (Caranta et al., "A Complementation of Two Genes Originating from Susceptible *Capsicum annuum* Lines Confers a New and Complete Resistance to Pepper Veinal Mottle Virus," *Phytopathology* 86:739-743 (1996), which is hereby incorporated by reference in its entirety). Two other eIF4E homologs did not map near known resistance genes and lacked characteristic polymorphism between resistant and susceptible genotypes. eIF4E cap-binding motifs were highly conserved among all eIF4E isoforms and homologs, implying functional redundancy within the pepper genome.

Originally described as alleles of the same locus, pvr1 and pvr2 have since been attributed to distinct loci without clear justification. When genetic complementation for resistance to TEV-HAT was assessed, pvr1 and $pvr2^2$ failed to complement (FIG. 1C) (see Examples 1-5, supra), defining eIF4E-687 as a candidate for all three genes.

Amino acid alignments were used to compare eIF4E-687 alleles from a wide array of germplasm representing pvr1, $pvr2^1$ and $pvr2^2$ (FIG. 2A). Each allele showed characteristic amino acid substitutions consistent with known breeding pedigrees. Based on these sequences, it appears pvr1 and pvr2 are the result of independent mutations that originated in *C. chinense* and *C. annuum*, respectively. Predicted structural models show conformational shifts that could disrupt cap-binding in all three alleles and amino acid substitutions at ($pvr2^2$) or near (pvr1) a highly conserved stabilizing residue involved in cap-binding (Marcotrigiano et al., "Cocrystal Structure of the Messenger RNA 5' Cap-Binding Protein (eIF4E) Bound to 7-Methyl-GDP," *Cell* 89:951-61 (1997), which is hereby incorporated by reference in its entirety) (FIG. 2B) (see Examples 1-5, supra).

Transient expression of a susceptible eIF4E-687 allele in resistant pvr1 plant leaves via *Agrobacterium* infiltration functionally complemented the resistant phenotype (FIG. 3) (see Examples 1-5, supra). Taken together, functional complementation, co-segregation, genetic complementation analyses and sequence data confirm that pvr1, and by extension, pvr2 are mutant alleles of eIF4E-687.

Based on the reported correlation of eIF4E/VPg interaction and viral infectivity, eIF4E-687 alleles from resistant and susceptible hosts were cloned and analyzed in the yeast two-hybrid system for interaction with TEV-HAT VPg (FIG. 4A) (see Examples 1-5, supra). The fusion protein from the susceptible host showed strong interaction with TEV-HAT VPg, while the pvr1 fusion protein failed to interact. This result suggests that potyvirus resistance conferred by pvr1 may be a consequence of defect(s) that interfere with the interaction between host eIF4E and viral VPg.

In order to determine whether the pvr1/eIF4E-687 allele was functional in its cellular role of cap-binding, the same alleles were expressed in *E. coli* and resulting proteins were assayed for binding-activity on $m^7$-GTP cap-analog columns (FIG. 4B) (see Examples 1-5, supra). eIF4E from the susceptible host showed strong cap-binding activity, while the pvr1 product failed to bind the column. Plants homozygous for pvr1 are phenotypically normal in every respect, therefore the cap-binding activity of eIF4E-687 appears to be non-essential for host survival. Taken together, VPg and cap-binding results indicate that a functional eIF4E-687 is essential for pathogenesis of viral genotypes controlled by these genes but dispensable for the host.

An explanation regarding the molecular basis of resistance in this system must account for different resistance mechanisms (replication vs. cell-to-cell movement) attributed to this locus, and for the observation that putative structural differences in eIF4E-687 correlate with differences in strain-specificity (see Examples 1-5, supra). These differences would be coupled with virus strain-specific structural differences in the VPg molecule to produce an interaction phenotype that determines resistance or susceptibility. The VPg/eIF4E interaction has been proposed to confer a translational advantage to the virus (Lellis et al., "Loss-of-Susceptibility Mutants of *Arabidopsis thaliana* Reveal an Essential Role for eIF(iso)4E During Potyvirus Infection," *Curr. Biol.* 12:1046-51 (2002), which is hereby incorporated by reference in its entirety), however there is evidence that both eIF4E and VPg are dispensable for cap-independent translation in both potyvirus and in polio, a member of Picornaviridae which share many features of genome structure and function with the Potyviridae (Gallie, "Cap-Independent Translation Conferred by the 5' Leader of Tobacco Etch Virus is Eukaryotic Initiation Factor 4G Dependent," *J. Virol.* 75:12141-52 (2001); Sachs et al., "Starting at the Beginning, Middle, and End: Translation Initiation in Eukaryotes," *Cell* 89:831-8 (1997); Nomoto et al., "The 5'-Terminal Structures of Poliovirion RNA and Poliovirus mRNA Differ Only in the Genome-Linked Protein VPg," *Proc. Natl. Acad. Sci. USA* 74:5345-9 (1977); Keller et al., "Potyvirus Genome-Linked Protein (VPg) Determines Pea Seed-Borne Mosaic Virus Pathotype-Specific Virulence in *Pisum sativum*," *Mol. Plant Microbe Interact.* 11: 124-30 (1998); and Riechmann et al., "Highlights and Prospects of Potyvirus Molecular Biology," *J. Gen. Virol.* 73:1-16 (1992), which are hereby incorporated by reference in their entirety). In many RNA virus/host systems, cellular translational machinery is recruited into the viral replicase complex, bringing 5' and 3' regulatory elements together (Lai, "Cellular Factors in the Transcription and Replication of Viral RNA Genomes: A Parallel to DNA-Dependent RNA Transcription," *Virology* 244:1-12 (1998), which is hereby incorporated by reference in its entirety); in poliovirus, translation and replication are coupled processes (Novak et al., "Coupling Between Genome Translation and Replication in an RNA Virus," *Genes Dev.* 8:1726-37 (1994), which is hereby incorporated by reference in its entirety).

Based on these findings, a model that focuses on RNA replication to explain how eIF4E mutants that fail to interact with VPg result in the extreme cellular resistance observed in pvr1 and $pvr2^2$ genotypes is favored (FIG. 4C). This model predicts that mutations that disrupt eIF4E-687 binding with either VPg or the putative cre element would block replication at a very early stage and produce a phenotype consistent with pvr1 and $pvr2^2$. This hypothesis is based on data drawn both from polio and potyvirus systems, which show sequence and structural similarity among their replication proteins (Riechmann et al., "Highlights and Prospects of Potyvirus Molecular Biology," *J. Gen. Virol.* 73:1-16 (1992), which is hereby incorporated by reference in its entirety).

In contrast to the extreme block described above, isolated protoplasts from plants homozygous for $pvr2^1$ accumulate virus to susceptible levels, suggesting that this allele should not have the functional defect above, however, eIF4E-VPg binding properties may be altered in such a way to affect VPg availability and/or function (Arroyo et al., "Impaired Cell-to-Cell Movement of Potato Virus Y in Pepper Plants Carrying the Y-A (pr2-1) Resistance Gene," *Mol. Plant Microbe Interact.* 9:314-318 (1996), which is hereby incorporated by reference in its entirety). VPg and the 5' terminus of the viral genome are critical for virion assembly (Wu et al., "Evidence that Assembly of a Potyvirus Begins Near the 5' Terminus of the Viral RNA," *J. Gen. Virol.* 79:1525-9 (1998), which is hereby incorporated by reference in its entirety) and association with the coat protein is essential for potyvirus movement (Revers et al., "New Advances in Understanding the Molecular Biology of Plant/Potyvirus Interactions," *Mol. Plant Microbe Interact.* 12:367-376 (1999), which is hereby incorporated by reference in its entirety).

The recent identification of eIF(iso)4E as the gene responsible for TEV and TuMV replication-defective mutants in *Arabidopsis* (Lellis et al., "Loss-of-Susceptibility Mutants of *Arabidopsis thaliana* Reveal an Essential Role for eIF(iso)4E During Potyvirus Infection," *Curr. Biol.* 12:1046-51 (2002), which is hereby incorporated by reference in its entirety) is complementary evidence that cap-binding proteins provide indispensable function for potyvirus infection. It is now clear that both eIF4E and eIF(iso)4E are strong candidates for a number of naturally occurring recessive potyvirus resistance genes. Based on mapping data in tomato and pepper, pot-1 and pvr5 are likely to be eIF4E-687 homologs (Parella et al., "Recessive Resistance Genes Against Potyviruses are Localized in Colinear Genomic Regions of the Tomato (*Lysopersicon* spp.) and Pepper (*Capsicum* spp.) Genomes," *Theor. Appl. Genet.* 105:855-861 (2002), which is hereby incorporated by reference in its entirety), while pvr6 is likely to be eIF(iso)4E.

In other recessive potyvirus/host systems, candidate gene analysis will reveal the universality of this type of mutant (Keller et al., "Potyvirus Genome-Linked Protein (VPg) Determines Pea Seed-Borne Mosaic Virus Pathotype-Specific Virulence in *Pisum sativum*," *Mol. Plant Microbe Interact.* 11:124-30 (1998); Nicolas et al., "Variations in the VPg Protein Allow a Potyvirus to Overcome va Gene Resistance in Tobacco," *Virology* 237:452-9 (1997); and Drijfhout et al., *Netherlands Journal of Plant Pathology* 84:13-26 (1978), which are hereby incorporated by reference in their entirety). Another possible candidate gene for recessive resistance is PABP (Wang et al., "Interaction Between Zucchini Yellow Mosaic Potyvirus RNA-Dependent RNA Polymerase and Host Poly-(A) Binding Protein," *Virology* 275:433-43 (2000), which is hereby incorporated by reference in its entirety), if there is sufficient redundancy in the host genome to avoid lethality. The apparently dispensable eIF4E homolog, eIF4E-687, may then define an opportunity to engineer extreme cellular-level resistance by targeted silencing in transgenic plants (Azevedo et al., "The RAR1 Interactor SGT1, an Essential Component of R Gene-Triggered Disease Resistance," *Science* 295:2073-6 (2002), which is hereby incorporated by reference in its entirety). As more is learned that links functional shifts in resistance mechanism and specificity to defined changes in interacting host and pathogen molecules, the pvr system should offer a unique opportunity to extend the understanding of the role host gene products play in viral pathogenesis, and the molecular determinants of host-pathogen specificity. Further, this study establishes eIF4E and eIF(iso)4E as viable candidates for a plethora of naturally occurring virus resistance genes for which molecular markers may be very useful in agriculture and may open the prospect for superior transgenic strategies to engineer highly durable resistance to control an extremely broad set of plant viruses.

Example 9

Plant Material

Micro-tom (Ball Seeds) were used. T0 generation transgenic plants were used for Northern blotting. T1 generation progenies of the transgenic plants were used for further analysis.

Example 10

Plasmid Construction

To make antisense and sense constructs of eIF4E, full length eIF4E cDNA sequences were amplified tomato and pepper cDNA using primers eIF4E-SacI/eIF4E-SmaI or eIF4E-SmaI/eIF4E-SacI and cloned into corresponding sites of pBI121 vector. Different pepper genotypes (234, RN, TAB0 representing 3 spp. of *Capsicum* were used as a source for the eIF4E allele.

To make a RNAi construct the tomato eIF4E cDNA sequence was PCR amplified using primers containing attB1 and attB2 sequence and the PCR product was cloned into pHELLSGATE2 vector by BP recombination reaction as described in manufacturer's instruction.

Example 11

Plant Transformation

*Agrobacterium tumefaciens* LBA4404 was used for plant transformation. The transformation procedure was as described previously (Micro-tom transformation procedure).

Example 12

RNA Isolation and Northern Blot Analysis

Total RNA was isolated from 6 week old pepper seedling leaves using TRIZOL (Gibco BRL Life Technologies, Rockville, Md.) according to the manufacturer's instruction. About 10 μg of the total RNA was separated on a 1.2% formaldehyde denaturing gel and transferred to nylon membranes. The blots were hybridized with random-primed $^{32}P$ labeled DNA probes as previously described (Livingstone et al., "Genome Mapping in *Capsicum* and the Evolution of Genome Structure in the Solanaceae," *Genetics* 152:1183-1202 (1999), which is hereby incorporated by reference in its entirety).

Example 13

Genomic DNA Isolation and NPTII PCR

Tomato genomic DNA was isolate according to standard methods and the presence of the NPTII gene was confirmed using the polymerase chain reaction with NPTII-specific primers.

Example 14

Virus Inoculation and ELISA

The first two leaves of greenhouse grown seedlings at the 4-6 leaf stage were inoculated using carborundum with plant sap from TEV-HAT-infected tobacco plants ground in icecold 0.05 M potassium phosphate buffer, pH 8. Systemic infection was assayed at 15 days post-inoculation (dpi) by visual symptoms and confirmed by indirect ELISA. Table 1 summarizes the transformation experiments resulting in resistance.

TABLE 1

Summary of transformation experiments resulting in resistance

| Plasmid Constructs | Total No. of Transformants | No. of Transformansts (T0) showing low eIF4E expression | No of lines showed TEV resistance |
|---|---|---|---|
| pBI121:eIF4E-AS234 | 37 | 9 | 2 (234-AS27, 32) |
| pBI121:eIF4E-ASRN | 38 | 3 | 1 (RN-AS20) |
| pBI121:eIF4E-ASTAB | 31 | 6 | 2 (TAB-AS5, 24) |
| pBI121:eIF4E-234(S) | 13 | 3 | N/A |
| pBI121:eIF4E-RN(S) | 14 | 3 | 1 (RN-S13) |
| pBI121:eIF4E-TAB(S) | 8 | 1 | N/A |
| pHELLSGATE2:TAB | 20 | N/A | N/A |
| Total | 161 | 25 | |

TABLE 2

Summary of transformation experiments. 234, RN, TAB represent different sources of the eIF4E gene. AS = antisense, S = sense. NPTII result confirms transformation. Northern blotting reflects degree of expression of the eIF4E mRNA. H signifies a high level of expression was detected; M = moderate level of eIF4E mRNA expression and L = low/undetectable expression.

| Transgenic line | NPT2 PCR | Northern Blotting | TEV resistance |
|---|---|---|---|
| 234-AS1 | positive | H | |
| 234-AS2 | positive | H | |
| 234-AS3 | positive | M | |
| 234-AS4 | positive | H | |
| 234-AS6 | positive | M | |
| 234-AS8 | positive | H | |
| 234-AS9 | positive | H | |
| 234-AS10 | positive | H | |
| 234-AS11 | positive | M | |
| 234-AS12 | positive | H | |
| 234-AS13 | positive | L | resistant segregates |
| 234-AS14 | positive | H | |
| 234-AS15 | positive | H | |
| 234-AS16 | positive | L | resistant segregates |
| 234-AS17 | positive | H | |
| 234-AS18 | positive | M | |
| 234-AS19 | positive | L | |
| 234-AS20 | positive | H | |
| 234-AS22 | positive | H | |
| 234-AS23 | positive | H | |
| 234-AS24 | positive | M | |
| 234-AS25 | positive | H | |
| 234-AS26 | positive | M | |
| 234-AS27 | positive | L | resistant segregates |
| 234-AS28 | positive | H | |
| 234-AS29 | positive | H | |
| 234-AS30 | positive | L | |
| 234-AS31 | positive | H | |
| 234-AS32 | positive | L | resistant segregates |
| 234-AS33 | positive | L | |
| 234-AS34 | positive | H | |
| 234-AS35 | positive | H | |
| 234-AS36 | positive | L | |
| 234-AS37 | positive | L | |
| 234-AS38 | positive | L | |
| 234-AS40 | positive | H | |
| 234-AS42 | positive | H | |
| RN-AS1 | positive | H | |
| RN-AS2 | positive | H | |
| RN-AS3 | positive | H | |
| RN-AS4 | positive | H | |
| RN-AS5 | positive | H | |
| RN-AS8 | positive | H | |
| RN-AS9 | positive | H | |
| RN-AS10 | positive | H | |
| RN-AS11 | positive | H | |
| RN-AS13 | positive | L | resistant segregates |
| RN-AS14 | positive | H | |
| RN-AS15 | positive | H | |
| RN-AS16 | positive | H | |
| RN-AS17 | positive | H | |
| RN-AS18 | positive | H | |
| RN-AS19 | positive | H | |
| RN-AS20 | positive | L | resistant segregates |
| RN-AS21 | positive | H | |
| RN-AS22 | positive | H | |
| RN-AS23 | positive | H | |
| RN-AS24 | positive | H | |
| RN-AS25 | positive | H | |
| RN-AS26 | positive | H | |
| RN-AS27 | positive | M | |
| RN-AS28 | positive | H | |
| RN-AS29 | positive | H | |
| RN-AS30 | positive | H | |
| RN-AS31 | positive | M | |
| RN-AS32 | positive | H | |
| RN-AS33 | positive | H | |
| RN-AS34 | positive | H | |
| RN-AS35 | positive | H | |
| RN-AS36 | positive | M | |
| RN-AS37 | positive | H | |
| RN-AS38 | positive | L | |
| RN-AS39 | positive | H | |
| RN-AS40 | positive | H | |
| RN-AS41 | positive | H | |
| TAB-AS1 | positive | H | |
| TAB-AS2 | positive | H | |
| TAB-AS4 | positive | H | |
| TAB-AS5 | positive | L | resistant segregates |
| TAB-AS7 | positive | H | |
| TAB-AS8 | positive | H | |
| TAB-AS10 | positive | L | resistant segregates |
| TAB-AS11 | positive | H | |
| TAB-AS12 | positive | H | |
| TAB-AS14 | positive | M | |
| TAB-AS15 | positive | H | |
| TAB-AS16 | positive | M | |
| TAB-AS17 | positive | M | |
| TAB-AS19 | positive | M | |
| TAB-AS20 | positive | H | |
| TAB-AS21 | positive | H | |
| TAB-AS22 | positive | L | |
| TAB-AS23 | positive | H | |
| TAB-AS24 | positive | L | resistant segregates |
| TAB-AS25 | positive | H | |
| TAB-AS26 | positive | M | |

TABLE 2-continued

Summary of transformation experiments. 234, RN, TAB represent different sources of the eIF4E gene. AS = antisense, S = sense. NPTII result confirms transformation. Northern blotting reflects degree of expression of the eIF4E mRNA. H signifies a high level of expression was detected; M = moderate level of eIF4E mRNA expression and L = low/undetectable expression.

| Transgenic line | NPT2 PCR | Northern Blotting | TEV resistance |
|---|---|---|---|
| TAB-AS27 | positive | L | |
| TAB-AS28 | positive | H | |
| TAB-AS29 | positive | H | |
| TAB-AS30 | positive | H | |
| TAB-AS31 | positive | H | |
| TAB-AS32 | positive | L | resistant segregates |
| TAB-AS33 | positive | H | |
| TAB-AS34 | positive | H | |
| TAB-AS35 | positive | M | |
| TAB-AS36 | positive | H | |
| 234-S1 | positive | L | |
| 234-S2 | positive | H | |
| 234-S3 | positive | M | |
| 234-S4 | positive | L | |
| 234-S5 | positive | M | |
| 234-S6 | positive | H | |
| 234-S7 | positive | L | |
| 234-S8 | positive | M | |
| 234-S9 | positive | H | |
| 234-S10 | positive | H | |
| 234-S11 | positive | M | |
| 234-S12 | positive | H | |
| 234-S13 | positive | H | |
| RN-S1 | positive | H | |
| RN-S2 | positive | H | |
| RN-S3 | positive | L | |
| RN-S4 | positive | H | |
| RN-S5 | positive | L | |
| RN-S7 | positive | M | |
| RN-S8 | positive | H | |
| RN-S9 | positive | M | |
| RN-S10 | positive | M | |
| RN-S11 | positive | H | |
| RN-S12 | positive | M | |
| RN-S13 | positive | H | resistant segregates |
| RN-S18 | positive | L | |
| RN-S19 | positive | H | |
| TAB-S1 | positive | H | |
| TAB-S2 | positive | H | |
| TAB-S4 | positive | H | |
| TAB-S7 | positive | M | |
| TAB-S8 | positive | H | |
| TAB-S9 | positive | H | |
| TAB-S10 | positive | H | |
| TAB-S11 | positive | L | |

Example 15

Mutations in Translation Initiation Factor Eif4e that Confer Resistance to Potyvirus Infection in *Capsicum* Abolish Interaction with Tobacco Etch Virus Vpg in a Non-Specific Manner The objectives of the study were to identify and characterize the host factor responsible for pvr1-mediated resistance in pepper, and to establish the relationship of pvr1 to pvr$2^2$ with respect to their common resistance to TEV-HAT. Based on the prevalent role of NIa in determining potyvirus replication and movement functions with respect to recessive resistance genes and the well-documented interaction of NIa with host cap-binding factors, eIF4E and eIF(iso)4E were examined as candidate genes for pvr1.

In plants, the mRNA cap-binding protein eIF(iso)4E and the scaffolding protein eIF(iso)4G interact to form the core of the eIF(iso)4F complex, which supports translation initiation predominantly from mRNAs with unstructured 5' leaders (Gallie et al., "eIF4G Functionally Differs from eIFiso4G in Promoting Internal Initiation, Cap-Independent Translation, and Translation of Structured mRNAs," *J. Biol. Chem.* 276:36951-36960 (2001)). In contrast, eIF4F, comprised of the mRNA cap-binding protein eIF4E and scaffolding protein eIF4G, supports translation initiation of mRNAs with more complex 5' structures and may promote translation under cellular conditions that inhibit cap-dependent translation such as viral infection. In *Arabidopsis*, eIF4E and eIF(iso)4E share 52% identity at the amino acid level and show different patterns of expression (Rodriguez et al., "The *Arabidopsis thaliana* cDNAs Coding for eIF4E and eIF(iso)4E are Not Functionally Equivalent for Yeast Complementation and are Differentially Expressed During Plant Development," *Plant J.* 13:465-473 (1998)), although both are strongly expressed in young tissues that support high levels of potyviral replication.

The recessive pvr1 gene from *Capsicum* chinense confers broad-spectrum resistance to all known strains of Potato virus Y (PVY), Pepper mottle virus (PepMoV), and most known TEV strains (Kyle et al., "Proposed Revision of Nomenclature for Potyvirus Resistance Genes in *Capsicum," Euphytica* 97:183-188 (1997)). Broad-spectrum resistance to several PVY and TEV strains, but not PepMoV, is also conferred by the recessive *Capsicum annuum* gene pvr$2^2$. These genes have a common mechanism of resistance (blocked replication) to the highly-aphid transmissible (HAT) strain of TEV (Deom et al., "Resistance to Tobacco Etch Virus in *Capsicum annuum*: Inhibition of Virus RNA Accumulation," *Mol. Plant Microbe Interact.* 10:917-921 (1997); and Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998)). In addition to a shared mechanism of resistance to at least one viral isolate, these broad-spectrum resistance genes share a common position on comparative genetic maps, raising the question of their genetic relationship to one another. Another allele at the pvr2 locus, pvr$2^1$, provides narrow-spectrum resistance to only pathotype 0 of PVY, apparently by blocking cell-to-cell movement (Arroyo et al., "Impaired Cell-to-Cell Movement of Potato Virus Y in Pepper Plants Carrying the Y-A (pr2-1) Resistance Gene," *Mol. Plant Microbe Interact.* 9:314-318 (1996)).

Several recent reports have confirmed that both eIF(iso)4E and eIF4E play a critical role in potyviral infection. Map-based cloning in *Arabidopsis* revealed that induced nonsense mutations in eIF(iso)4E resulted in broad-spectrum potyvirus resistance to TEV and TuMV (Lellis et al., "Loss-of-Susceptibility Mutants of *Arabidopsis thaliana* Reveal an Essential Role for eIF(iso)4E During Potyvirus Infection," *Curr. Biol.* 12:1046-1051 (2002), which is hereby incorporated by reference in its entirety). A transposon-disrupted eIF(iso)4E mutant identified through reverse genetics has since been shown to confer broad-spectrum resistance to TuMV and Lettuce mosaic virus (LMV) (Duprat et al., "The *Arabidopsis* Eukaryotic Initiation Factor (iso)4E is Dispensable for Plant Growth but Required for Susceptibility to Potyviruses," *Plant J.* 32:927-934 (2002), which is hereby incorporated by reference in its entirety). Further evidence from *Capsicum* and lettuce demonstrates that naturally occurring mutations in eIF4E are responsible for strain-specific PVY resistance conferred by pvr$2^1$ and pvr$2^2$ in pepper (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety) and for resistance to LMV conferred by mol (Nicaise et al., "The Eukaryotic Translation Initiation Factor 4E Controls Lettuce Susceptiblity to the Potyvirus Lettuce Mosaic Virus," *Plant Phys.* 132:1272-1282 (2003), which is hereby incorporated by reference in its entirety).

Translation initiation factors eIF4E and eIF(iso)4E have been shown to interact with the multifunctional potyvirus protein NIa and to be important host factors for potyviral infection. It has been shown that mutations in the eIF4E homolog eIF4E-687 result in broad-spectrum potyvirus resistance conferred by pvr1 in *Capsicum*, a gene widely deployed in agriculture. Two other resistance genes with narrower resistance spectra, pvr2$^1$ and pvr2$^2$, were determined to be alleles at the pvr1 locus and were re-designated pvr1$^1$ and pvr1$^2$. Mutations in pvr1, pvr1$^1$ and pvr1$^2$ grouped to similar regions of the gene and were predicted by protein homology models to cause conformational shifts in the encoded proteins. Because the interaction between eIF(iso)4E and NIa is considered critical for potyvirus infection, yeast two-hybrid and GST pull-down assays were performed with alleles of eIF4E-687 and NIa or VPg, respectively, from two different strains of Tobacco etch virus (TEV) that differentially infected *Capsicum* lines carrying these genes. The eIF4E homolog eIF4E-687 isolated from pvr1, pvr1 and pvr1$^2$ genotypes failed to bind NIa/VPg from either strain of TEV, however, this failure to interact did not consistently correlate with infectivity. These data suggest that interruption of the interaction between NIa/VPg and eIF4E-687 may be necessary but is not sufficient for potyvirus resistance in vivo. Among the three resistance alleles, only the pvr1 gene product also failed to bind m$^7$-GTP cap-analog columns, suggesting that disrupted cap-binding is not required for potyvirus resistance.

The results of this study both complement and extend these findings by demonstrating that mutations in pepper eIF4E (eIF4E-687) are also responsible for broad-spectrum potyvirus resistance conferred by the pvr1 allele in *Capsicum*, and the pvr2 alleles are actually variants at the pvr1 locus. The results show that pvr1 carries a unique set of amino acid substitutions relative to pvr2$^1$ and pvr2$^2$. Described is an additional amino acid substitution in the pvr2$^2$ allele, not previously reported, confirmed by sequencing eIF4E-687 from three pvr2$^2$/pvr2$^2$ pepper cultivars. When recombinant pvr1$^+$, pvr2, pvr2$^1$, and pvr1$^2$ eIF4E proteins were assayed for their ability to bind m$^7$-GTP cap analog columns, only pvr1 failed to bind indicating that disruption of this function may not be necessary for resistance and that knockout mutations at this locus may be viable. To test the hypothesis proposed in earlier studies that amino acid substitutions in the pvr2$^1$ and pvr2$^2$ alleles disrupted interaction with TEV-HAT NIa resulting in resistance, a systematic study was conducted of eIF4E-687/NIa interactions in vitro. In every case, the mutations in the pvr1, pvr2$^1$ and pvr2$^2$ alleles resulted in disrupted eIF4E-687 binding of NIa from either TEV strain; however, the lack of interaction was not correlated with resistance phenotypes. These findings require revision of gene nomenclature at this locus and indicate that potyvirus resistance cannot be predicted solely on the basis of NIa/VPg binding or cap-binding with eIF4E-687 proteins. It is likely that the determinants of specificity in this system will reside elsewhere.

Example 16

Plants, Viruses and Populations for Genetic Studies

Seeds of *C. annuum* 'NuMex RNaky' (RN), 'Early Cal Wonder' (ECW), 'Florida VR2' (VR2), 'Yolo Y' (YY), 'Del Ray Bell' (DRB), and breeding lines '3618', '5502', and '4074' were obtained from Asgrow Seed Co., San Juan Bautista, Calif. *C. annuum* 'Dempsey' (DEMP) was provided by M. Deom, University of Georgia and *C. annuum* 'Jupiter' was provided by Syngenta Seeds, Naples, Fla.; *C. chinense* PI 152225, PI 159234 (234), and PI 159236 were obtained from the USDA Southern Regional Plant Introduction Station, Experiment, GA; *C. chinense* 'Habanero' (Hab) was obtained from Tomato Growers Supply Co., Fort Myers, Fla. TEV-HAT and TEV-NW (non-wilting) cultures were obtained from T. Pirone, University of Kentucky, Lexington, Ky. PepMoV-FL (Florida) was obtained from T. Zitter, Cornell University, Ithaca, N.Y. All potyvirus strains were maintained on TMV-resistant *Nicotiana tabacum* 'Kentucky 14' and were transferred every 4-8 weeks.

For genetic complementation experiments, the set of resistant parents (DEMP, VR2, 3628, 5502) were intercrossed in all combinations and crossed with the susceptible parents Jupiter and ECW. Parents and F$_1$ progenies were inoculated with TEV-HAT and assayed for symptoms and presence of viral antigen by indirect ELISA.

DNA samples from F$_2$ individuals of an interspecific mapping population (AC population) used in a previous study to map the pvr1 locus were used to assess genetic markers for the pvr1 locus (Livingstone et al., "Genome Mapping in *Capsicum* and the Evolution of Genome Structure in the Solanaceae," *Genetics* 152:1183-1202 (1999), which is hereby incorporated by reference in its entirety). A second population of 114 F$_3$ families was generated for this study from an intraspecific cross between *C. chinense* 'Habanero' and *C. chinense* PI 159234 (CC population). This population was scored for resistance to TEV-HAT and PepMoV in two separate screens. DNA samples were extracted as described previously for genotypic analysis (Livingstone et al., "Genome Mapping in *Capsicum* and the Evolution of Genome Structure in the Solanaceae," *Genetics* 152:1183-1202 (1999); and Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998), which are hereby incorporated by reference in their entirety).

Example 17

Virus Screening Procedure

The first two leaves of greenhouse grown seedlings at the 4-6 leaf stage were inoculated using carborundum with plant sap from TEV-HAT-infected or PepMoV-infected tobacco plants ground in ice-cold 0.05 M potassium phosphate buffer, pH 8. Systemic infection was assayed at 21 days post-inoculation (dpi) by visual symptoms and confirmed by indirect ELISA (Voller et al., "The Detection of Viruses by Enzyme-Linked Immuno-Sorbent Assay," *J. Gen. Virol.* 33:165-167 (1976), which is hereby incorporated by reference in its entirety).

Example 18

RNA Isolation, RNA Blots and RT-PCR

Total RNA was isolated from young pepper leaves using Trizol reagant (Invitrogen, Carlsbad, Calif.) following the manufacturer's instructions. RNA blots were done according to standard methods (Sambrook et al., "Molecular Cloning: A Laboratory Manual," Third Edition, Cold Spring Harbor, N.Y.: Cold Spring Harbor Laboratory Press (2001), which is hereby incorporated by reference in its entirety). First strand cDNA was synthesized in 25 µl containing 2 µg total RNA and 500 ng oligo dT using M-MLV reverse transcriptase (Promega, Madison, Wis.) according to the manufacturer's instructions. For RT-PCR, 2 µl of cDNA was added to a reaction volume of 25 µl containing 10 mM KCl, 10 mM $(NH_4)_2SO_4$, 20 mM Tris-HCl, 2 mM $MgSO_4$, 0.100 Triton X-100, 0.2 mM each dNTP, 0.4 µM each forward and reverse primer, and 1 unit Taq polymerase (New England Biolabs, Beverly, Mass.). PCR cycling conditions were 95° C. 3 m, (95° C. 30 s, 55° C. 30 s, 72° C. 5 m)×1, (95° C. 30 s, 55° C. 30 s, 72° C. 90 s)×29, 72° C. 10 mm. Full-length eIF4E-687 ORF primers (forward 5'-ATGGCAACAGCTGAAATGG-3' (SEQ ID NO:9); reverse 5'-TATACGGTGTAACGATTCT-TGGCA-3' (SEQ ID NO:10) were based on tomato eIF4E sequence (Genbank accession AF259801). Full-length eIF (iso)4E ORF primers (forward 5'-AACAATGGCCAC-CGAAGC-3' (SEQ ID NO:15); reverse 5'-ATTTCACAG-TATATCGGCTCT-3' (SEQ ID NO:16)) were based on published tomato sequence (TIGR accession TC103222). Full-length eIF4E-537 ORF primers (forward 5'-TTAG-GCAAACCAATCACAATG-3' (SEQ ID NO:19); reverse 5'-CCTGTTGTAACGATAGAACTA-3' (SEQ ID NO:20)) were based on published tomato sequence (TIGR accession TC96888). PCR products were run on 1.5% agarose. Gel slices were purified using the Qiaquick gel purification kit (Qiagen, Valencia, Calif.) and cloned using the pGEM-T Easy kit (Promega, Madison, Wis.).

Example 19 cDNA Sequence Alignment and Protein Modeling

At least two positive clones were sequenced from both ends for each PCR product and analyzed using Seqman software (DNASTAR Inc., Madison, Wis.). Amino acid sequence alignments were produced using the Clustal algorithm within Megalign software (DNASTAR). For protein homology models, pepper sequence was submitted to the SwissProt database via the application DeepView. The model was generated using the murine crystal structure for eIF4L (sequence 1EJ1.B).

Example 20

Genome-Walking and Alignment of Genomic Sequence

For genome-walking 5' to eIF4E-687, nested internal primers 79R 5'-CACCTTCTTCAACTTCATCATCTGCCT-3' (SEQ ID NO:21) and 56R 5'-CATCATCTGCCTTCATTAG-CATTCAAT-3' (SEQ ID NO:14) were designed for use with the nested primers included in the Universal Genome-Walking Kit (Clontech, Palo Alto, Calif.). Subsequent PCR reactions followed manufacturer's instructions. Genome-walking was also used to span the 3.6 kb intron I of eIF4E-687. Nested primer sequences were 9F 5'-AGCTGAAATG-GAGAAAACGACGA-3' (SEQ ID NO:22) and 39F 5'-TTTGATGAAGCTGAGAAGGTGAAATTG-3' (SEQ ID NO:23) for the first walk and MW1F 5'-CGGCTTGAAAGT-TCAGTTAGTCAAC-3' (SEQ ID NO:24) and MW2F 5'-GC-CAACTAACTTAGCTACTAAGATTTTCAG-3' (SEQ ID NO:25) for the second walk. The remainder of intron I was spanned using primers I1F 5'-GCCATTCGACTAATCCT-CAGCAAC-3' (SEQ ID NO:26) and 321WR 5'-CCTCCAT-TGGCACATACAGGATCT-3' (SEQ ID NO:27). Intron II was spanned with the E23 marker using primers E23F 5'-AATATCCATCACCCAAG-3' (SEQ ID NO:11) and E23R 5'-GCTCCACATATTTCATC-3' (SEQ ID NO:12). Intron III was spanned using primer 12F 5'-CACTCTAGTAATAT-TATTTTCTGT-3' (SEQ ID NO:28) and primer 625R 5'-TGAAATATGAAGCCAACACTG-3' (SEQ ID NO:29). For genome-walking through intron IV and the 3' end of the gene, nested internal primers 580F 5'-GGTAAGCAATG-GAAGCAGTTCTG-3' (SEQ ID NO:30) and 595F 5'-CAGTTTCTGGATTACAGCGACAGT-3' (SEQ ID NO:31) were utilized. Bands were gel-purified from agarose using the Qiaquick gel extraction kit, cloned into pGEM-T Easy, and sequenced. A contig was created that spanned the eIF4E locus using overlapping PCR clones with Seqman software (DNASTAR).

Example 21

DNA Blots

DNA blotting and hybridization were done as reported previously (Livingstone et al., "Genome Mapping in *Capsicum* and the Evolution of Genome Structure in the Solanaceae," *Genetics* 152:1183-1202 (1999), which is hereby incorporated by reference in its entirety). Probes were amplified via PCR from cloned DNA fragments, purified from agarose using the Qiaquick gel extraction kit and labeled with $^{32}P$ using the Prime-It Random Primer Labeling Kit (Promega) according to manufacturer's instructions. Labeled probe was purified through a Sephadex G50 column, incubated with blots overnight at 65° C., then washed once with 2×SSC, once with 1×SSC and twice with 0.5×SSC. All washes included 0.1% SDS. Filters were placed on Kodak XAR-5 film. Genetic maps were assembled using Map-Maker/EXP v3.0b (Livingstone et al., "Genome Mapping in *Capsicum* and the Evolution of Genome Structure in the Solanaceae," *Genetics* 152:1183-1202 (1999), which is hereby incorporated by reference in its entirety).

Example 22

CAPS Markers

The upstream primer used to amplify the promoter region containing the SspI CAPS differential cleavage site was based on sequence obtained by genome-walking. The reverse primer lies 56 bases within the eIF4E-687 open reading frame. The reaction volume of 50 µl contained 50 ng genomic DNA, 10 mM KCl, 10 mM $(NH_4)_2SO_4$, 20 mM Tris-HCl, 2 mM $MgSO_4$, 0.1% Triton X-100, 0.2 mM each dNTP, 0.4 µM each forward primer 5'-TTACACGCGCCGATACACTTG-3' (SEQ ID NO:13) and reverse primer 5'-CATCATCTGCCT-FCATTAGCATTCAAT-3' (SEQ ID NO:14), and 2 units Taq polymerase (New England Biolabs). Cycling conditions were 95° C. 3 m, (95° C. 30 s, 60° C. 30 s, 72° C. 5 m)×1 cycle, (95° C. 30 s, 60° C. 30 s, 72° C. 90 s)×29 cycles, 72° C. 10 m. A 20 µl aliquot of PCR product was digested with 2.5 units of SspI (New England Biolabs) in a 30 µl reaction volume.

Example 23

Agro-Infiltration Transient Assay for Functional Complementation

For transient expression of eIF4E via agroinfiltration, eIF4E-234 and eIF4E-RN were cloned into the pBI121 plasmid. *Agrobacterium tumefaciens* LBA4404 was transformed by electroporation with the constructs above and the empty vector and grown overnight at 28° C. in LB medium containing 50 µg/ml kanamaycin and 50 µg/ml streptomycin. The overnight cultures were washed, resuspended in induction medium and induced overnight. Cells were collected by centrifugation and resuspended in 10 mM MES and 10 mM MgCl$_2$ containing 150 µM acetosyringone to an OD$_{600}$ of 0.2, then infiltrated using a 1 ml syringe into the first true leaves of susceptible (*C. chinense* Habanero) or resistant (*C. chinense* 234) pepper plants. Infiltrated leaves were then inoculated with TEV-HAT 3 days after infiltration. Uninoculated and mock-inoculated controls were also included. Five days after TEV inoculation, leaves were collected and TEV accumulation was test by immuno-blotting using a anti-TEV coat protein antisera. eIF4E expression was also assayed by the same method using human anti-eIF4E antibody (New England Biolabs).

Example 24

Yeast Two-Hybrid Analysis

Yeast two-hybrid analysis was performed according to published methods (Golemis et al., "Interaction Trap/Two-Hybrid System to Identify Interacting Proteins," In Ausubel et al., eds., *Current Protocols in Molecular Biology*, New York: Wiley, pp. 20.1.1-20.1.28 (1996), which is hereby incorporated by reference in its entirety). Yeast strains and plasmid vectors were provided by G. Martin (Boyce Thompson Institute, Ithaca, N.Y.). A bait plasmid pEG202 was used for the fusion of NIa to the DNA binding domain of LexA. The DNA sequences encoding NIa from TEV-HAT and NIa from TEV-NW were amplified by PCR from full-length clones provided by J. Murphy (Auburn University, Auburn, Ala.) using forward primer 5'-GCC GAATTCATGGGGAAGAAGAATCAGA-3' (SEQ ID NO:32) (EcoRI site underlined) and reverse primer 5'-CC CTCGAGCTATTGCGTGTACACCAATTC-3' (SEQ ID NO:33) (XhoI site underlined). A prey plasmid pJG4-5 was used to express *Capsicum* eIF4E-687 alleles. The eIF4E-687 sequences from different pepper genotypes known to be homozygous for each resistance allele were amplified using forward primer 5'-GAATTCATGGCAACAGCTGAA-3' (SEQ ID NO:34) (EcoRI site underlined) and 5'-CTCGAGCTATACGGTGTAACG-3' (SEQ ID NO:35) (XholI site underlined). The amplified fragments were digested with EcoRI and XhoI and cloned into corresponding restriction sites of pEG202 and pJG4-5, respectively. NIb of TEV-HAT was amplified by PCR using forward primer 5'-CC GAATTCATGGGAGAGAAGAGGAAATG-3' (SEQ ID NO:36) (EcoRI site underlined) and reverse primer 5'-CC CTCGAGCTACTGAAAATAAAGATTCTC-3' (SEQ ID NO:37) (XhoI site underlined) and cloned into pEG202 as a positive control for interaction with NIa in the β-galactosidase assay. All constructs were confirmed by sequencing. Bait recombinant plasmids were transformed into yeast strain EGY48 containing the lacZ reporter plasmid pSH18-34 using the lithium acetate method. Yeast cells containing pSH18-34 and bait plasmids were subsequently transformed with the prey plasmid pJG45:NIa. For two-hybrid assays, transformants were grown in complete minimal medium lacking histidine, tryptophan, and uracil, supplemented with 2% galactose/1% raffinose and X-gal. The degree of interaction was determined by the β-galactosidase liquid assay (Victoria, "Yeast Vectors and Assays for Expression of Cloned Genes, In Ausubel et al., eds., *Current Protocols in Molecular Biology*, New York: Wiley, pp. 13.6.1-13.6.4 (1996), which is hereby incorporated by reference in its entirety) and protein expression was assayed by immunoblots probed with anti-eIF4E to assure equivalent expression and stability in all treatments.

Example 25

GST In Vitro Pull-Down Assay

Each of the three resistant alleles, eIF4E-234 (pvr1), eIF4E-YY pvr2$^1$), eIF4E-DEMP (pvr2$^2$), and the susceptible allele, eIF4E-RN (pvr1$^+$), were cloned into the pET16b vector and translated in vitro using TnT coupled reticulocyte lysate (Promega). GST, GST-VPgHAT, and GST-VPgNW proteins were bound to 10 µl GST-Sepharose beads and resuspended in 195 µl IPAB-gelatin buffer (20 mM HEPES pH7.8, 150 mM KCl, 0.1% gelatin, 0.1% Triton X-100, 0.1% NP-40, 5 mM MgCl$_2$, 2 mM DTT). TnT translation products (5 µl) were added to prepared GST fusion Sepharose, mixed by end-over rotation at 4° C. for overnight, and washed 3× with 1×PBS buffer containing 2 mM DTT. The Sepharose beads were resuspended in 20 µl SDS-PAGE loading buffer and incubated for 2 min at 100° C. Released proteins were separated by SDS-PAGE. Following electrophoresis, gels were fixed, dried, and exposed to a phosphorimaging screen.

Example 26

Cap-Binding Assays

The coding region of pepper eIF4E-687 was amplified by PCR with forward primer 5'-C CATATGGCAACAGCTGA-3' (SEQ ID NO:38) (NdeI site underlined) and reverse primer 5'-CC CTCGAGCTATACGGTGTAACGA-3' (SEQ ID NO:39) (XhoI site underlined). The amplified fragments were then digested by NdeI and XhoI and cloned into pET16b (Novagen, Madison, Wis.) in frame with the 6× histidine tag. The constructs were confirmed by sequencing before transformation into *E. coli* BL21 (DE3)pLysS (Novagen). Expression of the recombinant proteins and purification of the proteins by m$^7$GTP-Sepharose 4.B (Amersham Bioscience, Piscataway, N.J.) were carried out as described previously with minor modification (Hagedorn et al., "Expression of Functional eIF4E Human: Purification, Detailed Characterization, and Its Use in Isolating eIF4E Binding Proteins," *Protein Expr. Purif.* 9:53-60 (1997), which is hereby incorporated by reference in its entirety). Expression of recombinant proteins was induced at 20° C. for 20 h by addition of 20 µM IPTG. The bacterial cells from 500 ml culture were resuspended in 5 ml of extraction buffer (20 mM Tris-HCl, pH 7.5 (4° C.), 100 mM KCl, 1 mM EDTA, 1 mM DTT, 1 mM PMSF) and sonicated. After cell lysis, Triton X-100 was added to a final concentration of 0.1% and stirred for 15 m at 4° C. The samples were centrifuged 20 m at 22,000×g; the supernatant was recovered for the cap-binding assay and applied to a 0.5 ml affinity column saturated with extraction buffer. The column was washed extensively with extraction buffer and eIF4E-687 protein was eluted using extraction buffer containing 100 uM m$^7$GTP. SDS-PAGE and immunoblot analysis were carried out as described previously (Murphy et al., "Isolation and Viral Infection of *Capsicum* Leaf Protoplasts," *Plant Cell Rep.* 13:397-400 (1994), which is hereby incorporated by reference in its entirety), using human anti-eIF4E antibody (New England Biolabs) for detection of recombinant eIF4E-687.

Example 27

Cosegregation of eIF4E-687 with pvr1

Figure 8:
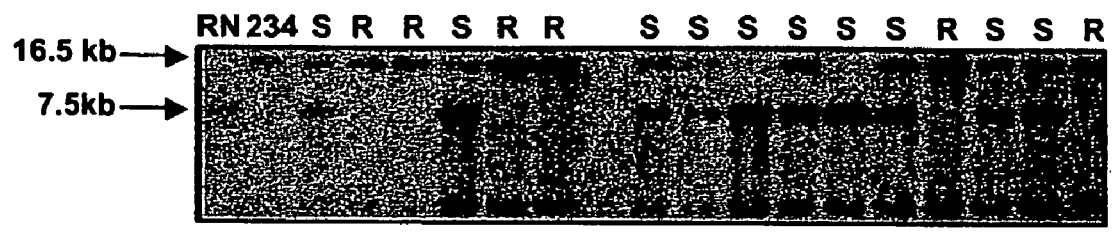
Figure 8:
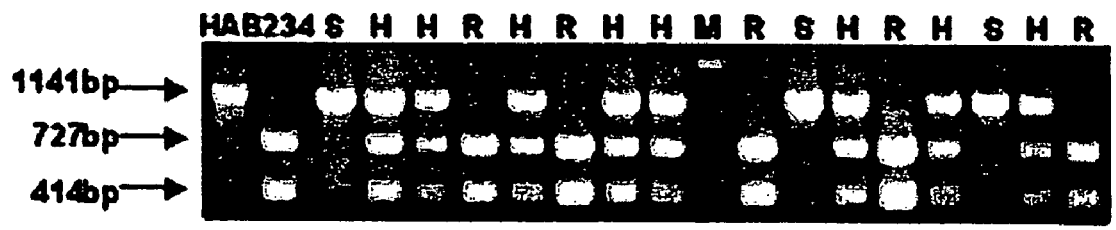

Primers based on a 696 bp tomato eIF4E coding sequence (Genbank accession AF259801) were used to amplify a 687 bp pepper eIF4E fragment (eIF4E-687) with 87% nucleotide sequence identity to tomato and 62% nucleotide sequence identity to *Arabidopsis* eIF4E (EMBL accession Y10548). A hybridization probe generated from eIF4E-687 identified a polymorphism that mapped precisely to pvr1 in the interspecific AC mapping population (FIG. 8A) (Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998), which is hereby incorporated by reference in its entirety). The SspI CAPS marker based in the 5' upstream region of the gene confirmed this result in the intra-specific CC population (FIG. 8B).

Primers based on a 603 bp tomato eIF(iso)4E sequence (TIGR accession TC103222) amplified a 609 bp pepper eIF(iso)4E with 89% nucleotide sequence identity to tomato and 63% nucleotide sequence identity to *Arabidopsis* eIF(iso)4E (EMBL accession Y10547). DNA blot hybridization of pepper eIF(iso)4E in the AC population showed that it was unlinked to pvr1, localizing instead to a chromosomal interval containing the recessive resistance gene pvr6, reported to confer resistance to the potyvirus Pepper veinal mottle virus (PVMV) when combined with pvr2$^2$ (Caranta et al., "A Complementation of Two Genes Originating from Susceptible *Capsicum annuum* Lines Confers a New and Complete Resistance to Pepper Veinal Mottle Virus," *Phytopathology* 86:739-743 (1996), which is hereby incorporated by reference in its entirety).

Primers based on the ORF of a 537 bp tomato eIF4E homolog (TIGR accession TC96888) amplified a 537 bp pepper fragment with 96% nucleotide sequence identity to tomato and 71% nucleotide sequence identity to *Arabidopsis* eIF4E. This eIF4E homolog (eIF4E-537) did not map near known resistance genes and lacked any characteristic polymorphisms between resistant and susceptible genotypes. Tryptophan and other cap-binding residues (Marcotrigiano et al., "Cocrystal Structure of the Messenger RNA 5' Cap-Binding Protein (eIF4E) Bound to 7-Methyl-GDP," *Cell* 89:951-961 (1997), which is hereby incorporated by reference in its entirety) were highly conserved among all eIF4E isoforms and homologs, consistent with functional redundancy for cap-binding within the pepper genome.

Example 28

Genetic Complementation Analysis of pvr1 and pvr2$^2$ Demonstrates Allelism

Figure 9:
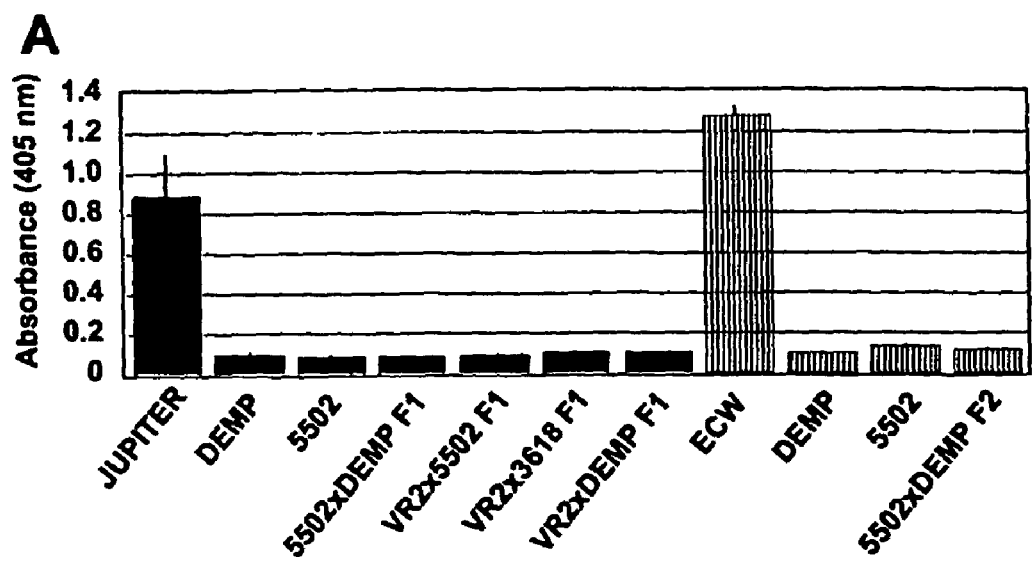
Figure 9:
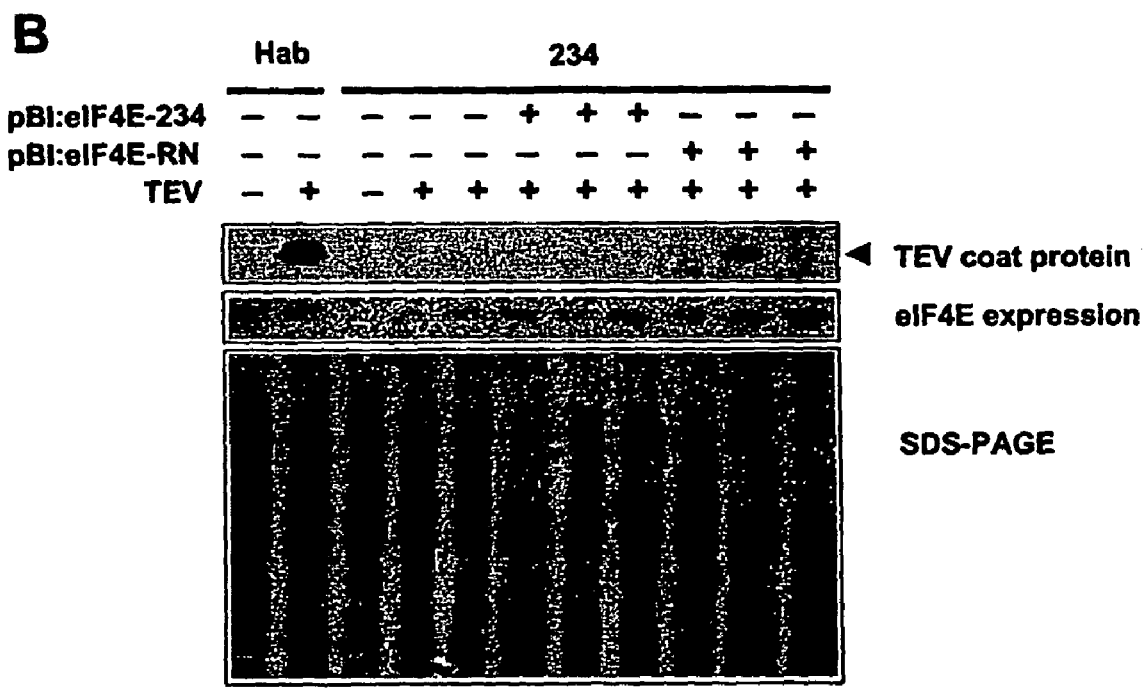

Allelism between pvr2$^1$ and pvr2$^2$ was established in early studies using PVY pathotype 0 (Cook, "A Mutation for Resistance to Potato Virus Y in Pepper," *Phytopathology* 51:550-552 (1961), which is hereby incorporated by reference in its entirety). The formal genetic relationship of pvr1 and pvr2$^2$ was never addressed. Originally described as alleles of the et locus for resistance to TEV (Deom et al., "Resistance to Tobacco Etch Virus in *Capsicum annuum*: Inhibition of Virus RNA Accumulation," *Mol. Plant Microbe Interact.* 10:917-921 (1997); and Herold et al., "Poliovirus RNA Replication Requires Genome Circularization Through a Protein-Protein Bridge," *Mol. Cell* 7:581-591 (2001), which are hereby incorporated by reference in their entirety), they were subsequently assigned to distinct loci (Sachs et al., "Starting at the Beginning, Middle, and End: Translation Initiation in Eukaryotes," *Cell* 89:831-838 (1997), which is hereby incorporated by reference in its entirety). Comparative mapping data places both genes near a common RFLP marker TG135, which in tomato is closely linked to pot-1, a recessive resistance gene in tomato for TEV and PVY resistance (Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998); Parella et al., "Recessive Resistance Genes Against Potyviruses are Localized in Colinear Genomic Regions of the Tomato (*Lysopersicon* spp.) and Pepper (*Capsicum* spp.) Genomes," *Theor. Appl. Genet.* 105:855-861 (2002), which are hereby incorporated by reference in their entirety). Both pvr1 and pvr2$^2$ confer resistance to TEV-HAT infection at the cellular level (Deom et al., "Resistance to Tobacco Etch Virus in *Capsicum annuum*: Inhibition of Virus RNA Accumulation," *Mol. Plant Microbe Interact.* 10:917-921 (1997); Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998), which are hereby incorporated by reference in their entirety), therefore this strain can be used to evaluate genetic complementation based on the resistance phenotypes of F$_1$ progeny derived from the two resistant sources. When genetic complementation for resistance to TEV-HAT was assessed, pvr1 and pvr2$^2$ failed to complement (FIG. 9A). Because the pvr1 allele was described first (Greenleaf, "Inheritance of Resistance to Tobacco Etch Virus in *Capsicum frutescens* and in *Capsicum annuum*," *Phytopathology* 46:371-375 (1956), which is hereby incorporated by reference in its entirety), the designation pvr1 should take priority for the eIF4E-687 locus. Based upon genetic complementation results and rules for potyviral resistance gene nomenclature in *Capsicum*, the pvr2$^1$ allele should be redesignated pvr1$^1$, while the pvr2$^2$ allele should be redesignated pvr1$^2$.

Example 29

Functional Complementation of a Resistant Genotype with eIF4E

Functional complementation for susceptibility was established via transient expression of resistant (eIF4E-234, pvr1) and susceptible (eIF4E-RN, pvr1$^+$) alleles via agroinfiltration into susceptible (Hab) and resistant (234) seedlings, together with appropriate controls for infiltration. Infiltrated and control seedlings were challenged with TEV-HAT and assayed by immunoblot for expression of eIF4E and TEV CP. Mock-inoculated and uninoculated controls were also included. TEV CP antigen was only detected in the positive control, the susceptible genotype inoculated with TEV, and in 234 plants infiltrated with the construct expressing the susceptible allele (FIG. 9B).

Example 30

Figure 10:
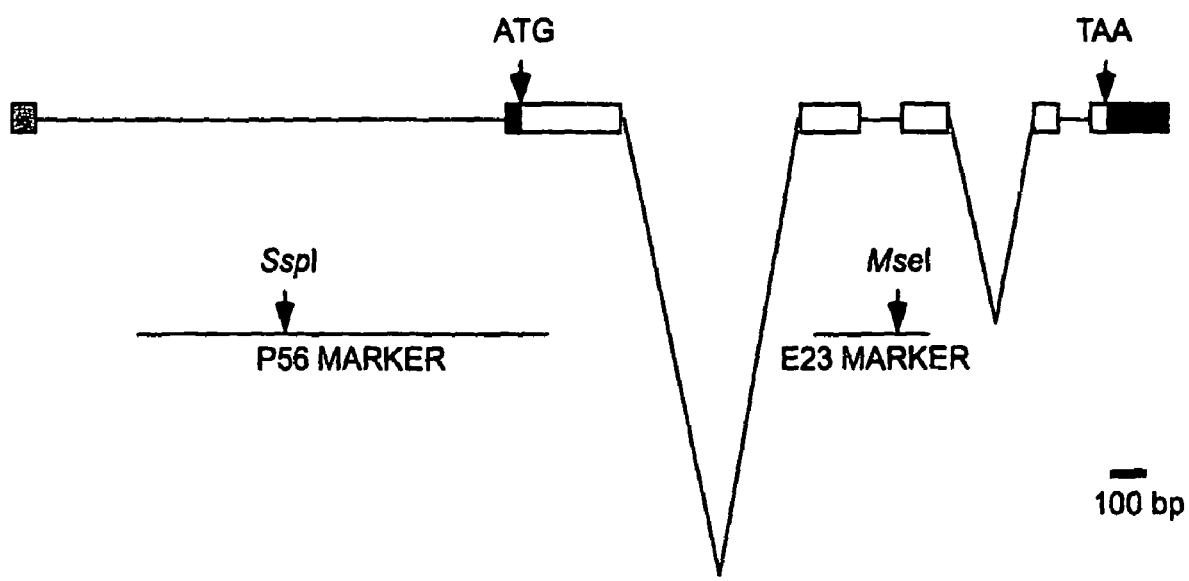
Figure 11:
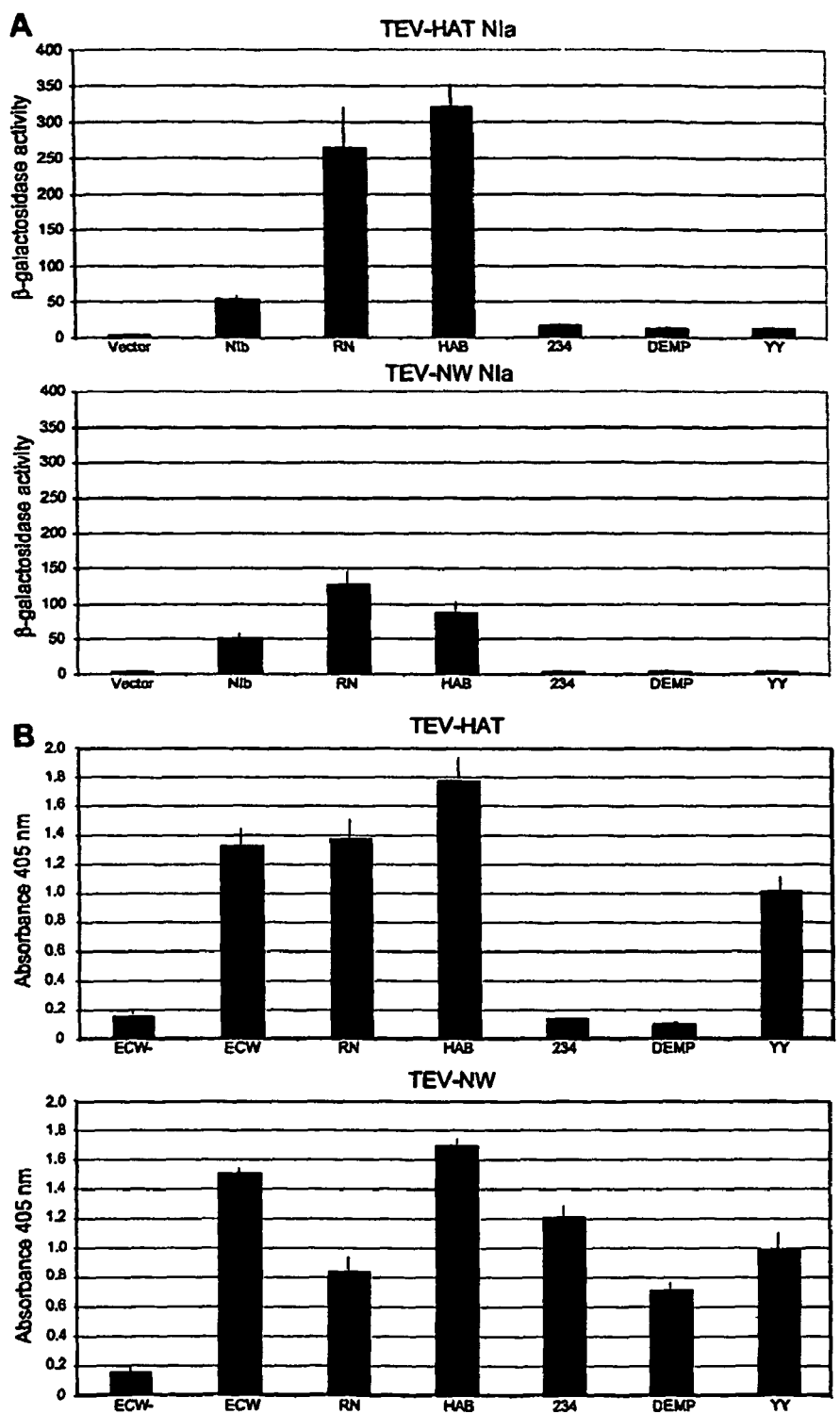

The Genetic Structure of the *Capsicum* eIF4E-687 Locus is Similar to *Arabidopsis* eIF4E Genomic sequence was obtained by genome-walking and genomic PCR to confirm the full-length gene sequence of eIF4E-687 and to describe the molecular structure of the locus (FIG. 10). A 66 bp region with 92% nucleotide sequence identity to bases 80-146 of the eIF4E-687 ORF was found approximately 1.3 kb upstream of the gene. Primers based 1.1 kb upstream of the gene and in exon 1 were used to generate the SspI P56 CAPS marker shown in FIG. 8B. The length of the first exon beginning from the ATG start codon was 278 bp. The first intron was quite large, measuring 3.6 kb. The PCR marker E23, generated using primers anchored in exons 2 (166 bp) and 3 (126 bp), spanned the 110 bp second intron and generated a MseI polymorphism that also cosegregated with pvr1 resistance. Intron III was 1.1 kb, while exon 4 was 66 bp. A final intron (intron IV) was 82 bp. Exon 5 up to the stop codon TAA was a total of 51 bp. Sequence corresponding to 5' untranslated region (28 bp) and 3' untranslated region (156 bp) was consistent with that previously reported (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety). Previous work has shown that at least one intron occurs in the eIF4E-687 locus because genomic PCR yielded a 1.8 kb amplicon, compared to a 493 bp cDNA product (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety). Based on alignment of the primer sequences with genomic sequence of the locus, our data confirm that this amplicon would span three introns and have a total length of 1836 bp. The four intron sites were completely conserved based on homology of pepper eIF4E-687 with *Arabidopsis* eIF4E. Exon length is also conserved between the two genes with the exception of exon 1, which is 20 bp longer in *Arabidopsis*.

Example 31

Resistance Alleles have Distinct Amino Acid Substitutions

Amino acid alignments were used to compare eIF4E-687 alleles amplified from *Capsicum* germplasm known to be homozygous for pvr1$^+$, pvr1, pvr1$^1$ or pvr1$^2$. Three *C. chinense* PIs (152225, 159234, and 159236) previously shown to be allelic for pvr1 (Murphy et al., "Genetic Mapping of the pvr1 Locus in *Capsicum* spp. and Evidence that Distinct Potyvirus Resistance Loci Control Responses that Differ at the Whole Plant and Cellular Levels," *Mol. Plant Microbe Interact.* 11:943-951 (1998), which is hereby incorporated by reference in its entirety) and three *C. annuum* bell pepper breeding lines known to carry pvr1 (3618, 4074, 5502) all carried identical sequence at the eIF4E-687 locus (FIG. 2A), consistent with their known pedigrees of inter-specific introgression of resistance from *C. chinense* to *C. annuum*. The pvr1 allele carries four amino acid substitutions relative to susceptible *C. annuum* pvr1$^+$ genotypes (FIG. 2A).

Bell pepper varieties 'Dempsey', 'Florida VR2', and 'Del Ray Bell' are known to be homozygous for pvr1$^2$. Their identical sequence at the eIF4E-687 locus is also consistent with a commonly introgressed resistance gene. This allele had three point mutations that differed from susceptible *C. annuum* genotypes, all within the same region as the pvr1 point mutations but at different residues. This suggests the hypothesis that the pvr1 and pvr1$^2$ alleles originated independently in *C. chinense* and *C. annuum*, respectively. The amino acid substitution L79R was not previously reported in the 'Florida VR2' eIF4E-687 sequence (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety), however, our results confirm this mutation is present in three independent germplasm sources. The eIF4E-687 sequence from 'YoloY' (pvr1$^1$) shares both of its amino acid substitutions with pvr1$^2$. While the reported pedigrees do not identify a common ancestor for these two alleles (Cook, "A Mutation for Resistance to Potato Virus Y in Pepper.," *Phytopathology* 51:550-552 (1961), which is hereby incorporated by reference in its entirety), their similar sequence is consistent with their shared resistance to PVY-0.

Three of the four point mutations in the pvr1 allele and all of the mutations in pvr1$^1$ and pvr1$^2$ cause non-conservative amino acid substitutions in the respective predicted proteins. Protein homology models based on mouse eIF4E predict conformational differences in the proteins as a result of the combination of mutations (FIG. 2B). It is also evident that in the three alleles, residues affected by these mutations localize to similar parts of the protein. Substitutions in pvr1, pvr1$^1$ and pvr1$^2$ are generally not located at highly-conserved residues involved in cap-binding or eIF4G binding, except in the case of the pvr1$^2$ D109R mutation. In contrast to earlier interpretation (Rodriguez et al., "The *Arabidopsis thaliana* cDNAs Coding for eIF4E and eIF(iso)4E are Not Functionally Equivalent for Yeast Complementation and are Differentially Expressed During Plant Development," *Plant J.* 13:465-473 (1998), which is hereby incorporated by reference in its entirety), this mutation does affect a highly conserved residue involved in stabilization of cap-binding (Marcotrigiano et al., "Cocrystal Structure of the Messenger RNA 5' Cap-Binding Protein (eIF4E) Bound to 7-Methyl-GDP," *Cell* 89:951-961 (1997), which is hereby incorporated by reference in its entirety). The pvr1 allele has a G107R mutation two residues away from this position.

Example 32

NIa/VPG Interaction with eIF4E-687 is not Correlated with TEV Resistance Phenotype The prevailing model indicates that interaction of eIF4E and NIa is required for potyviral infectivity (Leonard et al., "Complex Formation Between Potyvirus VPg and Translation Eukaryotic Initiation Factor 4E Correlates with Virus Infectivity," *J. Virol.* 74:7730-7737 (2000); Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002); Schaad et al., "Strain-Specific Interaction of the Tobacco Etch Virus NIa Protein with the Translation Initiation Factor eIF4E in the Yeast Two-Hybrid System," *Virology* 273:300-306 (2000), which are hereby incorporated by reference in their entirety) and predicts that conformational changes in eIF4E-687 gene products encoded by the potyvirus resistance alleles should abolish or impair NIa binding. In order to clarify how the mutations described above affect protein function and to examine whether the correlation between NIa binding and infectivity can be extended, interaction of NIa with eIF4E-687 proteins using the yeast two-hybrid assay and interaction of VPg with eIF4E-687 proteins using the GST pull-down assay were examined. In the yeast two-hybrid system, five different eIF4E-687 alleles were analyzed for interaction with NIa from two different TEV strains, TEV-HAT and TEV-NW (FIG. 11A). Characteristic infectivity of TEV-HAT and TEV-NW on homozygous $pvr1^+$, pvr1, $pvr1^1$ and $pvr1^2$ genotypes was confirmed by indirect ELISA. Results are depicted in FIG. 11B.

Activity values from vector-only negative interaction controls and NIb positive interaction controls were consistent with those reported in previous studies using TEV NIa (Schaad et al., "Strain-Specific Interaction of the Tobacco Etch Virus NIa Protein with the Translation Initiation Factor eIF4E in the Yeast Two-Hybrid System," *Virology* 273:300-306 (2000), which are hereby incorporated by reference in their entirety). The $pvr1^+$ alleles from TEV-susceptible genotypes RN and HAB interacted in vitro with NIa cloned from both viral isolates (FIG. 11A); RN and HAB developed severe infection when inoculated with either TEV-HAT or TEV-NW (FIG. 11B). In contrast, fusion proteins from resistance alleles cloned from *Capsicum* genotypes 234 (pvr1), DEMP ($pvr1^2$), and YY ($pvr1^1$) failed to interact with NIa from either virus although they were expressed at levels similar to susceptible alleles. Both 234 and DEMP failed to support viral infection of TEV-HAT (FIG. 11B). In four cases, however, where eIF4E-687/NIa interaction was interrupted, systemic viral infection was observed. YY ($pvr1^1$) is susceptible to both TEV-HAT and TEV-NW (FIG. 11B), even though eIF4E-687 isolated from YY failed to interact with NIa from either virus (FIG. 11A). Similarly, 234 (pvr1) and DEMP ($pvr1^2$) both support infection of TEV-NW even though there is no interaction in vitro between their respective eIF4E-687 alleles and TEV-NW NIa.

These data were confirmed and extended by a second assay of in vitro interaction shown in FIG. 12. Results confirmed that interaction was only observed between eIF4E-RN and TEV-HAT and TEV-NW VPg. No interaction was observed between the resistant alleles and either TEV-HAT or TEV-NW (FIG. 12).

These data uniformly supported the prediction that the translational products of pvr1, $pvr1^1$ and $pvr1^2$ alleles would show altered function with respect to NIa/VPg binding. Interruption of the interaction, however, was not uniformly correlated with failure to infect in vivo. Strong NIa/VPg/eIF4E-687 interaction in highly susceptible $pvr1^+$ hosts may promote potyviral infectivity, but to the extent that in vivo conditions can be extrapolated from in vitro assays, disruption of this interaction does not necessarily abolish infection.

Example 33

Cap-Binding Activity of eIF4E-687 is not Correlated with TEV Resistance Phenotype In order to determine whether eIF4E-687 proteins were functional with respect to their cellular role of cap-binding, $pvr1^+$, pvr1, $pvr1^1$ and $pvr1^2$ alleles were expressed in *E. coli* and resulting proteins were assayed for binding-activity on $m^7$-GTP cap-analog columns. All of the eIF4E-687 proteins were stably expressed in *E. coli* (FIG. 13A). The $pvr1^+$ eIF4E-687 allele from the susceptible host RN showed strong cap-binding activity, as did recombinant DEMP ($pvr1^2$) and YY ($pvr1^1$) eIF4E-687 proteins (FIG. 13) indicating that the D109R mutation specific to $pvr1^2$ did not abolish cap-binding. In contrast, the 234 (pvr1) product failed to bind the column. It is unclear whether this failure to bind was a result of the G107R mutation, or due to other disruptions in the protein. Plants homozygous for pvr1 are phenotypically normal in every respect, suggesting that the cap-binding activity of eIF4E-687 may not be essential for host viability. Furthermore, the observation that point mutations in two resistance alleles failed to disrupt cap-binding while disruption was observed in the third case is consistent with the hypothesis that cap-binding or its disruption may not be essential for the resistant response. It remains unclear whether this attribute of the pvr1 allele will in some way account for or contribute to its relatively broad spectrum of resistance.

These studies confirm that eIF4E-687 is the host factor responsible for recessive potyvirus resistance attributed to pvr1 and alleles formerly known as $pvr2^1$ and $pvr2^2$. A genetic complementation test confirmed that all three alleles occur at the same locus, requiring revision of the locus designation. Hybridization and sequence-based markers for the eIF4E-687 gene co-segregated completely with the pvr1 resistance phenotype in two independent populations. Furthermore, the wild type allele showed functional complementation when transiently expressed via agroinfiltration in a resistant genotype restoring susceptibility to TEV-HAT. Each resistant allele carried signature point mutations localized to similar regions of the gene. These data, together with a recent study that demonstrated that transient expression of wild-type eIF4E-687 in $pvr1^1$ and $pvr1^2$ genotypes restored susceptibility to PVY (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety), clearly indicate that mutations in this gene can result in broad spectrum potyvirus resistance. It is now clear from studies in *Arabidopsis*, lettuce and *Capsicum* and that cap-binding proteins play an important, if undefined, role in potyvirus infection.

VPg has been proposed to act as a viral determinant of infectivity in these resistance systems based on the identity of these resistance genes (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002); Nicaise et al., "The Eukaryotic Translation Initiation Factor 4E Controls Lettuce Susceptiblity to the Potyvirus Lettuce Mosaic Virus," *Plant Phys.* 132: 1272-1282 (2003), which are hereby incorporated by reference in their entirety). Avirulence determinants have not yet been established for race-specific resistance conferred by the *Capsicum* eIF4E-687 mutants. There are, however, amino acid differences within the VPg region of TEV strains virulent (TEV-NW) and avirulent (TEV-HAT) on pvr1 and $pvr1^2$ and differences within the VPg region of PVY strains virulent and avirulent on $pvr1^2$ (Ruffel et al., "A Natural Recessive Resistance Gene Against Potato Virus Y in Pepper Corresponds to the Eukaryotic Initiation Factor 4E (eIF4E)," *Plant J.* 32:1067-1075 (2002), which is hereby incorporated by reference in its entirety). Additional studies focusing on infectivity of chimeric infectious clones constructed between TEV-NW and TEV-HAT in *Capsicum* are currently underway to address this question.

Based upon results from a previous study which noted that a mutation in TuMV NIa (D77N) that abolished *Arabidopsis* eIF(iso)4E interaction also abolished infection in another host plant, *Brassica perividis* (Leonard et al., "Complex Formation Between Potyvirus VPg and Translation Eukaryotic Initiation Factor 4E Correlates with Virus Infectivity," *J.*

*Virol.* 74:7730-7737 (2000), which is hereby incorporated by reference in its entirety), it was proposed that the outcome of the interaction of eIF4E-687 and NIa would determine viral infectivity. It was not apparent from that study, however, whether this mutation in a highly conserved NIa residue acted only to interrupt interaction with eIF(iso)4E or caused some other instability in the NIa protein. Furthermore, the correlation was not tested directly by inoculating *Arabidopsis* with the mutant virus. In addition to the demonstrated interaction between TuMV NIa and translation factors eIF(iso)4E and eIF4E from the host species *Arabidopsis*, interaction was also observed in that study between TuMV NIa and eIF4E from wheat, a nonhost for the virus. This result is inconsistent with hypotheses that posit that the interaction between eIF4E and NIa is causal for infectivity, although it is possible that the correlation holds true only for eIF(iso)4E and not eIF4E.

Observations show that there is strong interaction of pvr1$^+$ eIF4E-687 proteins from *C. annuum* and *C. chinense* with NIa from TEV-HAT and TEV-NW, both of which cause severe infection. Absence of interaction was observed between the avirulent TEV-HAT NIa and resistant pvr1 and pvr1$^2$ eIF4E-687 alleles. However, also observed was a lack of interaction in four NIa/eIF4E assays that represent cases where the outcome of infection is susceptibility (TEV-HAT NIa/pvr1$^1$; TEV-NW NIa/pvr1; TEV-NW NIa/pvr1$^1$; TEV-NW NIa/pvr1$^2$). This result is clearly inconsistent with the hypothesis that this interaction predicts or determines the ability of a viral isolate to infect.

Results from other studies are consistent with the conclusion that eIF4E/NIa interaction is important but its outcome does not necessarily determine resistance. NIa from TEV-HAT is the avirulence determinant for recessive resistance to systemic movement in tobacco cultivar V20 (Schaad et al., "VPg of Tobacco Etch Potyvirus is a Host Genotype-Specific Determinant for Long-Distance Movement," *J. Virol.* 71:8624-8631 (1997), which is hereby incorporated by reference in its entirety). In an effort to identify host factors interacting with TEV-HAT NIa, a yeast two-hybrid screen identified tomato eIF4E from TEV susceptible variety VF36 as a strong interactor (Schaad et al., "Strain-Specific Interaction of the Tobacco Etch Virus NIa Protein with the Translation Initiation Factor eIF4E in the Yeast Two-Hybrid System," *Virology* 273:300-306 (2000), which is hereby incorporated by reference in its entirety). However, this eIF4E protein failed to interact with TEV-Oxnard NIa, even though VF36 is also susceptible to that virus. When eIF4E sequence was analyzed between the resistant tobacco cultivar V20 and two susceptible tobacco varieties, there was no difference, indicating that the gene was not involved in V20 resistance. Thus, NIa in this system is an avirulence determinant for a resistance mechanism that apparently does not involve eIF4E. Yeast two-hybrid assays confirmed that the tobacco eIF4E protein interacted with NIa from TEV-HAT, even though V20 blocked systemic movement of the virus; however in the same assay, eIF4E failed to interact with NIa from TEV-Oxnard, even though TEV-Oxnard can infect all three varieties. Experiments using chimeric NIa proteins carrying the minimal avirulence determinant suggested that the interaction determinants were genetically distinct from the avirulence determinant. Overexpression of eIF4E within the TEV genome in the same study appeared to have a stimulatory effect on replication, although there is no evidence that this stimulation involved interaction between VPg-Pro and eIF4E.

One important observation from the present study is that in one of the three alleles, the ability to bind capped mRNA is interrupted. This clearly demonstrates that impaired cap-binding ability is not essential for potyvirus resistance, however the relevance of this observation, if any, to the distinctive phenotypic features of this allele, e.g., increased resistance spectrum, remains to be determined. Premature stop codons and insertions into *Arabidopsis* eIF(iso)4E almost certainly interrupt both VPg and cap-binding and led to broad-spectrum potyvirus resistance in *Arabidopsis* (Duprat et al., "The *Arabidopsis* Eukaryotic Initiation Factor (iso)4E is Dispensable for Plant Growth but Required for Susceptibility to Potyviruses," *Plant J.* 32:927-934 (2002); Lellis et al., "Loss-of-Susceptibility Mutants of *Arabidopsis thaliana* Reveal an Essential Role for eIF(iso)4E During Potyvirus Infection," *Curr. Biol.* 12:1046-1051 (2002), which are hereby incorporated by reference in their entirety). A second implication of this result is that impaired cap-binding of eIF4E-687 has no apparent phenotypic consequences in pvr1 plants, consistent with functional redundancy in *Capsicum*. Specifically, it is possible that eIF4E-537, eIF(iso)4E, or other molecules may function in place of mutant eIF4E-687 in pvr1 genotypes. Likewise, no phenotypic defects were found in potyvirus resistant *Arabidopsis* eIF(iso)4E mutants, suggesting that redundancy for this function may be universal in plants. Although it is possible that *Capsicum* eIF4E-687 has cellular functions other than cap-binding that are as yet unknown, results imply that eIF4E-687 is a homolog whose function may be dispensable for the host, but essential for the virus. This homolog, therefore, defines a target for transgenic gene-silencing techniques to generate viable crop plants with stable engineered resistance to potyviruses.

Figure 12:
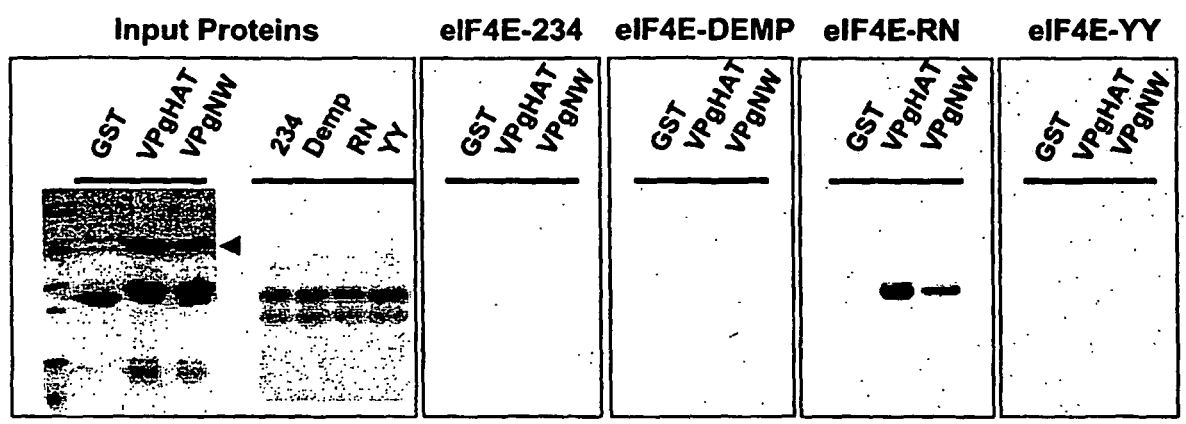
Figure 13:
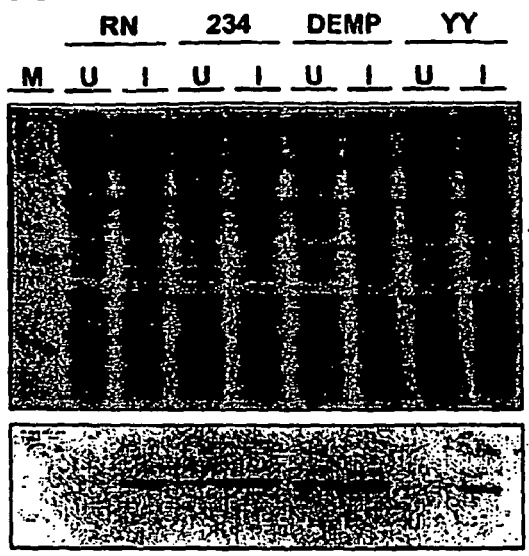
Figure 13:
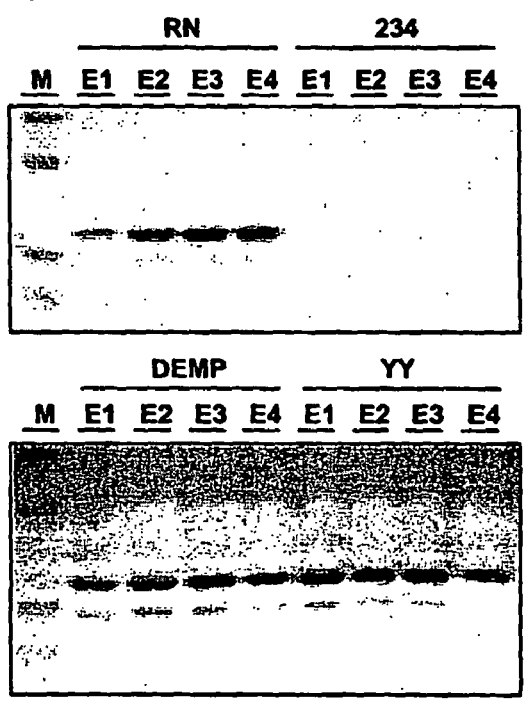

The pattern of amino acid substitutions observed among pvr1, pvr1$^1$ and pvr1$^2$ alleles depicted in FIG. 12 suggest testable hypotheses regarding the molecular basis for strain-specificity, the first such system to be defined. The pvr1 G107R mutation and pvr1$^2$ D109R mutations within the cap-binding slot may have similar effects on host-potyvirus interaction and result in resistance to TEV-HAT and PVY-1 common to both alleles. Conformational differences resulting from the two unique mutations, each in the region flanking the cap-binding slot allele (P66T and K71R in pvr1, V67E and L79R in both pvr1$^1$ and pvr1$^2$) may have similar consequences for resistance to PVY-0. Finally, the combined effect in pvr1 of the T51A mutation together with the other three mutations may serve to extend the resistance spectrum to include PepMoV and PVY-1, 2. It is unclear why the pvr1$^2$ K71R mutation was not previously reported, but confirmation from three independent cultivars that carry this allele, including 'Dempsey', the focus of pvr1$^2$ mechanistic studies (Deom et al., "Resistance to Tobacco Etch Virus in *Capsicum annuum*: Inhibition of Virus RNA Accumulation," *Mol. Plant Microbe Interact.* 10:917-921 (1997), which is hereby incorporated by reference in its entirety), supports this finding.

Models regarding the molecular basis of resistance at the pvr1 locus must account for two different resistance mechanisms (replication vs. cell-to-cell movement) attributed to this locus, and for the observation that putative structural differences in eIF4E-687 correlate with differences in strain-specificity. The simplest model would suggest that these differences would be coupled with virus strain-specific structural differences in the VPg molecule, the eIF4E binding domain of NIa, to produce an interaction phenotype that determines resistance or susceptibility. This model appears to hold in the case of pvr1$^+$ genotypes and in the case of pvr1 and pvr1$^2$ resistance to TEV-HAT. However, in four cases the lack of eIF4E-687 interaction with VPg did not correlate with resistance to the virus. Under these circumstances, other factors must compensate to promote systemic infection. Within plant cells, interaction of eIF4E-687 and VPg would likely be influenced by conformational changes brought on by interaction with other host and viral proteins and RNA. Therefore, there may be alternate ways to stabilize association of eIF4E-687 with VPg or to substitute for the function the interaction provides. In the case of pvr1 and pvr2² infection with TEV-NW and pvr1¹ infection with TEV-HAT, symptom development typically begins a few days later and proceeds at a slightly slower rate than that seen in pvr1⁺ genotypes. This might indicate a modified mode of infection by the virus when faced with eIF4E-687 proteins that fail to interact with VPg.

Interaction of VPg with eIF4E has been proposed to confer a translational advantage to the virus (Lellis et al., "Loss-of-Susceptibility Mutants of *Arabidopsis thaliana* Reveal an Essential Role for eIF(iso)4E During Potyvirus Infection," *Curr. Biol.* 12:1046-1051 (2002), which is hereby incorporated by reference in its entirety), however there is evidence from both potyvirus and poliovirus that both eIF4E and VPg are dispensable for cap-independent translation (Gallie, "Cap-Independent Translation Conferred by the 5' Leader of Tobacco Etch Virus is Eukaryotic Initiation Factor 4G Dependent," *J. Virol.* 75:12141-12152 (2001); Nomoto et al., "The 5'-Terminal Structures of Poliovirion RNA and Poliovirus mRNA Differ Only in the Genome-Linked Protein VPg," *Proc. Natl. Acad. Sci. USA* 74:5345-5349 (1977); Sachs et al., "Starting at the Beginning, Middle, and End: Translation Initiation in Eukaryotes," *Cell* 89:831-838 (1997), which are hereby incorporated by reference in their entirety). In many RNA virus-host systems, interaction between cellular translation machinery, viral proteins and RNA appears to be important in bringing 5' and 3' regulatory elements together for RNA replication (Herold et al., "Poliovirus RNA Replication Requires Genome Circularization Through a Protein-Protein Bridge," *Mol. Cell* 7:581-591 (2001); Lai, "Cellular Factors in the Transcription and Replication of Viral RNA Genomes: A Parallel to DNA-Dependent RNA Transcription," *Virology* 244:1-12 (1998), which are hereby incorporated by reference in their entirety). Interaction of these regulatory regions are proposed to favor viral replication for a number of reasons, including efficient recruiting of the RNA polymerase to the replication start site, ensuring that only intact viral templates are replicated, and coordinating RNA replication with translation (Herold et al., "Poliovirus RNA Replication Requires Genome Circularization Through a Protein-Protein Bridge," *Mol. Cell* 7:581-591 (2001), which is hereby incorporated by reference in its entirety). TEV is known to have RNA secondary structures at the 3' end of its genome that are required in cis for RNA replication (Haldeman-Cahill et al., "Secondary Structures in the Capsid Protein Coding Sequence and 3' Nontranslated Region Involved in Amplification of the Tobacco Etch Virus Genome," *J. Virol.* 72:4072-4079 (1998); and Mahajan et al., "Roles of the Sequence Encoding Tobacco Etch Virus Capsid Protein in Genome Amplification: Requirements for the Translation Process and a Cis-Active Element," *J. Virol.* 70:4370-4379 (1996), which are hereby incorporated by reference in their entirety). With VPg attached to the 5' end of the potyviral genome, interaction with eIF4E-687 could create a bridge to the 3' poly-A tail through interaction with eIF4G and poly-A binding protein, thus allowing regulation of RNA synthesis. Mutations in eIF4E-687 that interrupt this association could explain how pvr1 and pvr1² genotypes block replication of TEV-HAT.

Isolated protoplasts from plants homozygous for pvr1¹ accumulate PVY-0 to susceptible levels (Arroyo et al., "Impaired Cell-to-Cell Movement of Potato Virus Y in Pepper Plants Carrying the Y-A (pr2-1) Resistance Gene," *Mol. Plant Microbe Interact.* 9:314-318 (1996), which is hereby incorporated by reference in its entirety), suggesting that this allele does not share the same functional defect as described above for pvr1 and pvr1². The interaction between NIa from PVY pathotypes and this eIF4E allelic series has not been examined in vitro, but binding properties in the pvr1¹ mutant may be altered in such a way to affect VPg availability and/or function. One possibility is that eIF4E-687 may be recruited by VPg to the origin of virion assembly, shown to be near the 5' terminus of the viral genome (Wu et al., "Evidence That Assembly of a Potyvirus Begins Near the 5' Terminus of the Viral RNA," *J. Gen. Virol.* 79:1525-1529 (1998), which is hereby incorporated by reference in its entirety), and somehow affect the assembly process. Association of the viral genome with coat protein is essential for potyvirus movement (Revers et al., "New Advances in Understanding the Molecular Biology of Plant/Potyvirus Interactions," *Mol. Plant Microbe Interact.* 12:367-376 (1999), which is hereby incorporated by reference in its entirety) and disruption of this association could potentially result in blocked cell-to-cell movement.

Even though the precise mechanisms through which cap-binding factors promote potyvirus infection have yet to be resolved, it is now clear that both eIF4E and eIF(iso)4E are strong candidates for a number of naturally occurring recessive potyvirus resistance genes. Based on mapping data in tomato and pepper, respectively, pot-1 and pvr5 are likely to be eIF4E-687 homologs (Parella et al., "Recessive Resistance Genes Against Potyviruses are Localized in Colinear Genomic Regions of the Tomato (*Lysopersicon* spp.) and Pepper (*Capsicum* spp.) Genomes," *Theor. Appl. Genet.* 105: 855-861 (2002), which is hereby incorporated by reference in its entirety). Results presented here indicate that pvr6, which is reported to confer resistance to PVMV when combined with pvr1² (Caranta et al., "A Complementation of Two Genes Originating from Susceptible *Capsicum annuum* Lines Confers a New and Complete Resistance to Pepper Veinal Mottle Virus," *Phytopathology* 86:739-743 (1996), which is hereby incorporated by reference in its entirety), is likely to be eIF(iso)4E. The combined effects of mutations in two cap-binding isomers may also explain the epistatic effect of the recessive bc-u gene on recessive bean common mosaic virus (BCMV) resistance genes bc-1, bc-2 and bc-3 (Drijfhout, "Genetic Interaction Between *Phaseolus Vulgaris* and Bean Common Mosaic Virus with Implications for Strain Identification and Breeding for Resistance," *Agricultural Research Reports* 872 (1978), which is hereby incorporated by reference in its entirety). In other recessive potyvirus-host systems, candidate gene analysis will reveal the universality of eIF4E and eIF(iso)4E mutants (Keller et al., "Potyvirus Genome-Linked Protein (VPg) Determines Pea Seed-Borne Mosaic Virus Pathotype-Specific Virulence in *Pisum sativum*," *Mol. Plant Microbe Interact.* 11: 124-130 (1998); Nicolas et al., "Variations in the VPg Protein Allow a Potyvirus to Overcome va Gene Resistance in Tobacco," *Virology* 237:452-459 (1997), which are hereby incorporated by reference in their entirety).

The apparently dispensable eIF4E homolog, eIF4E-687, may define an opportunity to engineer extreme cellular-level resistance by targeted silencing in transgenic plants (Azevedo et al., "The RAR1 Interactor SGT1, an Essential Component of R Gene-Triggered Disease Resistance," *Science* 295:2073-2076 (2002), which is hereby incorporated by reference in its entirety). As more is learned that links functional shifts in resistance mechanism and specificity to defined changes in interacting host and pathogen molecules, the pvr1 system offers a unique opportunity to extend our understanding of the role host gene products play in viral pathogenesis, and the molecular determinants of host-pathogen specificity. Further, this study confirms eIF4E and eIF(iso)4E as viable candidates for a plethora of naturally occurring virus resistance genes for which molecular markers may be very useful in agriculture and may open the prospect for superior transgenic strategies to engineer highly durable resistance to control an extremely broad set of plant viruses.

Example 34

Transgenic Tomato Plants Containing Heterologous Sense eIF4E Genes: Plasmid Constructs The plasmids for tomato transformation were derived from pBI121. The full length ORFs of eIF4E genes were PCR amplified from cDNA of pepper eIF4E ('PI159234' and 'RNaky'), and tomato eIF4E (Rio Grande). GUS gene of pBI121 was replaced by the PCR amplified pepper and tomato eIF4E genes. The resulting plasmids constructs were designated pBI::eIF4E-234S, pBI::eIF4E-RNS, and pBI::eIF4E-LeS. In addition to the constructs, pBI121 with and without GUS gene were also used as negative controls.

Example 35

Transgenic Tomato Plants Containing Heterologous Sense eIF4E Genes: Tomato Transformation Microtom tissues were transformed and regenerated into whole plants as described earlier. About 46 transgenic plants were obtained from the constructs and eIF4E gene expression was tested by Northern blot analysis.

Example 36

Transgenic Tomato Plants Containing Heterologous Sense eIF4E Genes: Virus Resistance Test Seventeen transgenic plants showing either high or low eIF4E gene expression were tested for TEV virus resistance (see Table 3).

TABLE 3

Resistance to TEV Infection of Tomato Transgenic Plants Containing Sense eIF4E Genes of Pepper and Tomato

| Constructs | Tested line | eIF4E expression | Plant phenotype |
|---|---|---|---|
| pBI::eIF4E-234 | 234-S2 | H | Resistance segregates |
| | 234-S6 | H | Resistance segregates |
| | 234-S7 | L | All susceptible |
| | 234-S9 | H | Resistance segregates |
| | 234-S10 | H | Resistance segregates |
| | 234-S13 | H | Resistance segregates |
| pBI::eIF4E-RN | RN-S1 | H | All susceptible |
| | RN-S2 | H | All susceptible |
| | RN-S3 | L | All susceptible |

TABLE 3-continued

Resistance to TEV Infection of Tomato Transgenic Plants Containing Sense eIF4E Genes of Pepper and Tomato

| Constructs | Tested line | eIF4E expression | Plant phenotype |
|---|---|---|---|
| | RN-S4 | H | All susceptible |
| | RN-S8 | H | All susceptible |
| | RN-S11 | H | All susceptible |
| pBI::eIF4E-TAB | Le-S2 | H | All susceptible |
| | Le-S4 | H | All susceptible |
| | Le-S8 | H | All susceptible |
| | Le-S9 | H | All susceptible |

Tomato plants, at 4-6 leaf stage, were inoculated with sap extract from TEV infected tobacco leaves (5 ml of 50 mM sodium phosphate buffer per g of tissue) and scored for symptoms 14 days after inoculation. TEV coat protein accumulation in inoculated plants was tested by a dot blotting analysis after 21 days after inoculation. Dot blotting analysis was carried out as follows: A leaf disc (microtube cap size) was collected from each plant and ground in 50 volume of extraction buffer (1×TBS containing 50 mM diethyldithiocarbamate). The sample was centrifuged at 10,000 g for 2 min and diluted 100 times. About 40 µl of diluted extract was spotted on nitrocellulose membrane. The membrane was blocked with 5% BSA in 1×TBS and hybridized with TEV coat protein antibody and signal was developed using ECL detecting system according to manufacturer's instruction.

Example 37

Figure 14:
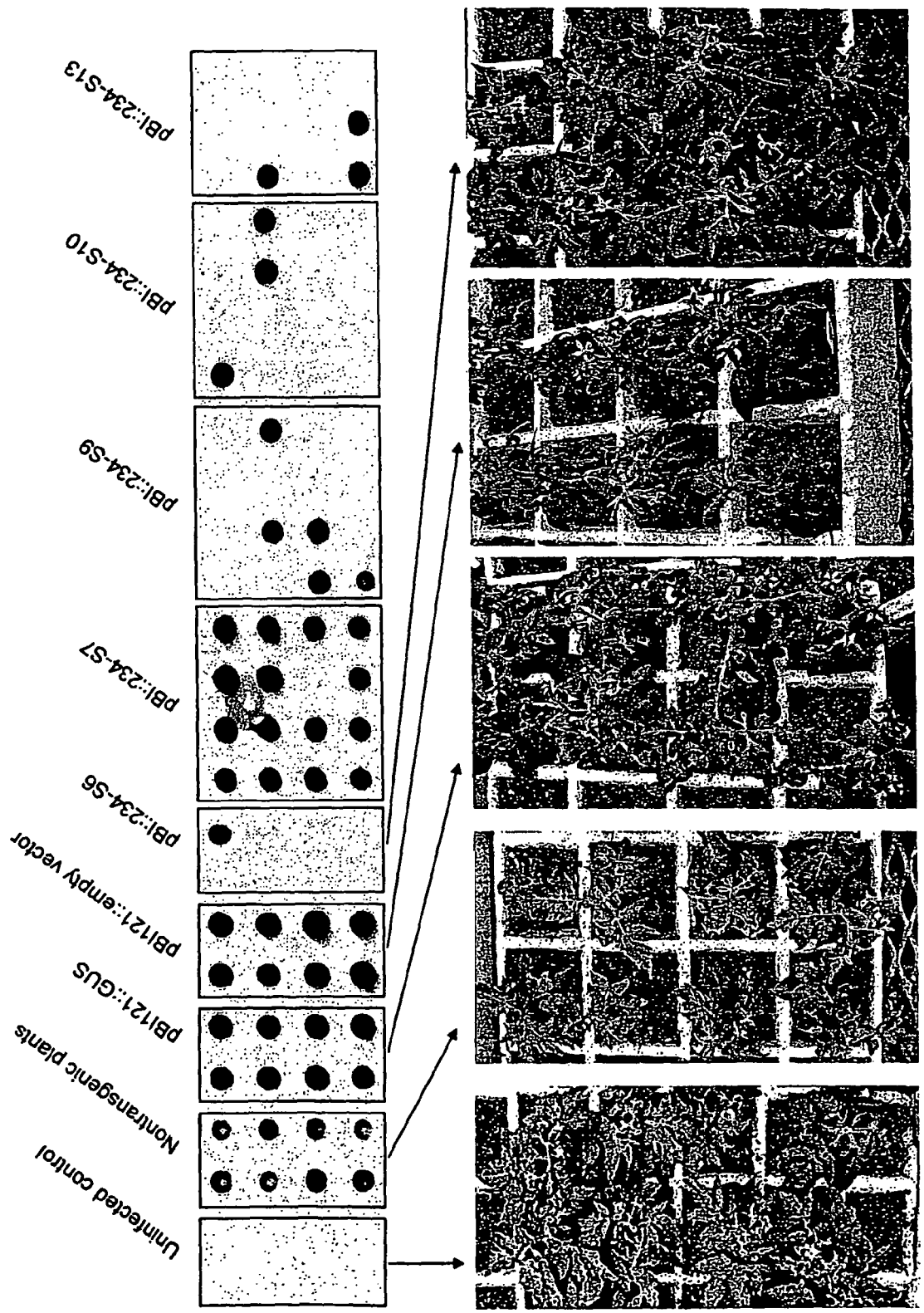

Transgenic Tomato Plants Containing Heterologous Sense eIF4E Genes: Results and Analysis Untransformed plants, pBI121 transgenic plants, and pBI121 empty vector transgenic plants showed TEV symptoms and TEV coat protein accumulation (FIG. 14). All the progenies of tomato transgenic plants of pBI::eIF4E-RNS and pBI::eIF4E-LeS, which contain functional eIF4E gene, showed susceptible phenotype to TEV virus regardless of eIF4E expression level. The progenies of tomato transgenic plants pBI::eIF4E-234-S6, S9, S10, and S13, which contain mutated eIF4E gene, showed resistant and susceptible phenotype segregation, where resistant phenotype was dominant. Resistant plants showed complete resistance, no TEV symptoms and no TEV coat protein accumulation (FIG. 14). However, resistant phenotype was observed only when the transgenic plants accumulate high level of eIF4E transcript (Table 3). These results indicate that TEV resistant plants can be engineered by overexpressing eIF4E-234 gene.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of imparting virus resistance to plants, said method comprising:
providing a nucleic acid molecule encoding a polypeptide at least 95 percent identical to translation initiation factor eIF4E of SEQ ID NO:2 and containing at least one substitution of at least one amino acid residue of SEQ ID NO:2 selected from the group consisting of T51A, P66T, V67E, K71R, L79R, G107P, and D109R, and
transforming a plant with the nucleic acid molecule under conditions effective to yield a transgenic plant that overexpresses said translation initiation factor eIF4E, wherein said method is effective in imparting virus resistance to the transgenic plant.

2. The method according to claim 1, wherein said transgenic plant is resistant against viruses of the Potyviridae family.

3. The method according to claim 2, wherein said transgenic plant is resistant against Potyviridae viruses selected from the group consisting of Lettuce Mosaic Virus, Pepper Mottle Virus, Potato Virus Y, Tobacco Etch Virus, and Turnip Mosaic Virus.

4. A transgenic plant produced according to the method of claim 1.

5. The transgenic plant according to claim 4, wherein said transgenic plant is selected from the group consisting of rice, wheat, barley, rye, cotton, sunflower, peanut, corn, potato, sweet potato, bean, pea, chicory, lettuce, endive, cabbage, cauliflower, broccoli, turnip, radish, spinach, onion, garlic, eggplant, pepper, celery carrot, squash, pumpkin, zucchini, cucumber, apple, pear, melon, strawberry, grape, raspberry, pineapple, soybean, tobacco, tomato, sorghum, sugarcane, banana, mung bean, alfalfa, rye, brussels sprout, beet, parsnip, citrus, *Arabidopsis, Saintpaulia*, petunia, pelargonium, poinsettia, chrysanthemum, carnation, and zinnia.

6. A component part of the transformed plant according to claim 4.

7. A fruit of the transformed plant according to claim 4.

8. A plant seed produced from the transformed plant according to claim 4.

9. The method according to claim 1, wherein the nucleic acid molecule is at least 95 percent identical to SEQ ID NO:1.

10. The method according to claim 1, wherein the amino acid residue substitution comprises T51A.

11. The method according to claim 1, wherein the amino acid residue substitution comprises P66T.

12. The method according to claim 1, wherein the amino acid residue substitution comprises V67E.

13. The method according to claim 1, wherein the amino acid residue substitution comprises K71R.

14. The method according to claim 1, wherein the amino acid residue substitution comprises L79R.

15. The method according to claim 1, wherein the amino acid residue substitution comprises G107P.

16. The method according to claim 1, wherein the amino acid residue substitution comprises D109R.

17. The method according to claim 1, wherein the polypeptide has the amino acid sequence of SEQ ID NO: 2 modified to contain at least one substitution of at least one amino acid residue of SEQ ID NO: 2 selected from the group consisting of T51A, P66T, V67E, K71R, L79R, G107P and D109R.

* * * * *

SEQUENCE LISTING

<160> NUMBER OF SEQ ID NOS: 39

<210> SEQ ID NO 1
<211> LENGTH: 875
<212> TYPE: DNA

-continued

<213> ORGANISM: Capsicum annuum

<400> SEQUENCE: 1

```
aaagtaaaaa aagcacacag caccaacaat ggcaacagct gaaatggaga aaacgacgac    60
gtttgatgaa gctgagaagg tgaaattgaa tgctaatgag gcagatgatg aagttgaaga   120
aggtgaaatt gttgaagaaa ctgatgatac gacgtcgtat ttgagcaaag aaatagcaac   180
aaagcatcca ttagagcatt catggacttt ctggtttgat aatccagtgg cgaaatcgaa   240
acaagctgct tggggtagct cgcttcgcaa cgtctacact ttctccactg ttgaagattt   300
ttggggtgct tacaataata tccaccaccc aagcaagtta gttgtgggag cagacttaca   360
ttgtttcaag cataaaattg agccaaagtg ggaagatcct gtatgtgcca atggagggac   420
atggaaaatg agttttttcaa agggtaaatc tgataccagc tggctatata cgctgcttgc   480
aatgattgga catcaattcg atcatgaaga tgaaatttgt ggagcagtag ttagtgtcag   540
aggtaaggga gaaaaaatat ctttgtggac caagaatgct gcaaatgaaa cggctcaggt   600
tagcattggt aagcaatgga agcagtttct ggattacagc gacagtgttg gcttcatatt   660
tcacgacgat gcaaagaggc tcgacagaaa tgcaagaat cgttacacag tataattctt   720
gatgcaatgt cggaatataa gaaacacaat tcgtactgaa aagttgtagg cactagttta   780
gtttctcata cgataaagct tctggtttga gtaccttgtg tattggtgtt tgcactttct   840
aatcgcgtaa aattgtccgg ttttggattc aaaaa                              875
```

<210> SEQ ID NO 2
<211> LENGTH: 228
<212> TYPE: PRT
<213> ORGANISM: Capsicum annuum

<400> SEQUENCE: 2

```
Met Ala Thr Ala Glu Met Glu Lys Thr Thr Thr Phe Asp Glu Ala Glu
  1               5                  10                  15

Lys Val Lys Leu Asn Ala Asn Glu Ala Asp Asp Glu Val Glu Glu Gly
             20                  25                  30

Glu Ile Val Glu Glu Thr Asp Asp Thr Thr Ser Tyr Leu Ser Lys Glu
         35                  40                  45

Ile Ala Thr Lys His Pro Leu Glu His Ser Trp Thr Phe Trp Phe Asp
     50                  55                  60

Asn Pro Val Ala Lys Ser Lys Gln Ala Ala Trp Gly Ser Ser Leu Arg
 65                  70                  75                  80

Asn Val Tyr Thr Phe Ser Thr Val Glu Asp Phe Trp Gly Ala Tyr Asn
                 85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
            180                 185                 190

Ile Gly Lys Gln Trp Lys Gln Phe Leu Asp Tyr Ser Asp Ser Val Gly
```

-continued

```
                195                 200                 205
Phe Ile Phe His Asp Asp Ala Lys Arg Leu Asp Arg Asn Ala Lys Asn
    210                 215                 220

Arg Tyr Thr Val
225

<210> SEQ ID NO 3
<211> LENGTH: 687
<212> TYPE: DNA
<213> ORGANISM: Capsicum chinense

<400> SEQUENCE: 3
atggcaacag ctgaaatgga gaaaacgacg acgtttgatg aagctgagaa ggtgaaattg      60
aatgctaatg aggcagatga tgaagttgaa gaaggtgaaa ttgttgaaga aactgatgat     120
acgacgtcgt atttgagcaa agaaatagca gcaaagcatc cattagagca ttcatggact     180
ttctggtttg ataatacagt ggcgaaatcg agacaagctg cttggggtag ctcgcttcgc     240
aacgtctaca ctttctccac tgttgaagat ttttggggtg cttacaataa tatccaccac     300
ccaagcaagt tagttgtgag agcagactta cattgtttca gcataaaaat tgagccaaag     360
tgggaagatc ctgtatgtgc caatggaggg acatggaaaa tgagttttttc aaagggtaaa     420 tctgatacca gctggctata tacgctgctt gcaatgattg gacatcaatt cgatcatgaa     480
gatgaaattt gtggagcagt agttagtgtc agaggtaagg gagaaaaaat atctttgtgg     540
accaagaatg ctgcaaatga aacggctcag gttagcattg gtaagcaatg gaagcagttt     600
ctggattaca gcgacagtgt tggcttcata tttcacgacg atgcaaagag gctcgacaga     660
aatgcaaaga atcgttacac cgtatag                                         687

<210> SEQ ID NO 4
<211> LENGTH: 228
<212> TYPE: PRT
<213> ORGANISM: Capsicum chinense

<400> SEQUENCE: 4

Met Ala Thr Ala Glu Met Glu Lys Thr Thr Thr Phe Asp Glu Ala Glu
  1               5                  10                  15

Lys Val Lys Leu Asn Ala Asn Glu Ala Asp Asp Glu Val Glu Glu Gly
             20                  25                  30

Glu Ile Val Glu Glu Thr Asp Asp Thr Thr Ser Tyr Leu Ser Lys Glu
         35                  40                  45

Ile Ala Ala Lys His Pro Leu Glu His Ser Trp Thr Phe Trp Phe Asp
     50                  55                  60

Asn Thr Val Ala Lys Ser Arg Gln Ala Ala Trp Gly Ser Ser Leu Arg
 65                  70                  75                  80

Asn Val Tyr Thr Phe Ser Thr Val Glu Asp Phe Trp Gly Ala Tyr Asn
                 85                  90                  95

Asn Ile His His Pro Ser Lys Leu Val Val Arg Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
    130                 135                 140

Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
```

```
                  165                 170                 175
Ile Ser Leu Trp Thr Lys Asn Ala Ala Asn Glu Thr Ala Gln Val Ser
            180                 185                 190
Ile Gly Lys Gln Trp Lys Gln Phe Leu Asp Tyr Ser Asp Ser Val Gly
        195                 200                 205
Phe Ile Phe His Asp Asp Ala Lys Arg Leu Asp Arg Asn Ala Lys Asn
    210                 215                 220
Arg Tyr Thr Val
225

<210> SEQ ID NO 5
<211> LENGTH: 687
<212> TYPE: DNA
<213> ORGANISM: Capsicum annuum

<400> SEQUENCE: 5
atggcaacag ctgaaatgga gaaaacgacg acgtttgatg aagctgagaa ggtgaaattg      60
aatgctaatg aggcagatga tgaagttgaa gaaggtgaaa ttgttgaaga aactgatgat     120
acgacgtcgt atttgagcaa agaaatagca acaaagcatc cattagagca ttcatggact     180
ttctggtttg ataatccaga ggcgaaatcg aaacaagctg cttggggtag ctcgcgtcgc     240
aacgtctaca ctttctccac tgttgaagat ttttggggtg cttacaataa tatccaccac     300
ccaagcaagt tagttgtggg agcagactta cattgtttca gcataaaat tgagccaaag     360 tgggaagatc ctgtatgtgc caatggaggg acatggaaaa tgagttttc aaagggtaaa     420 tctgatacca gctggctata tacgctgctt gcaatgattg acatcaatt cgatcatgaa     480 gatgaaattt gtggagcagt agttagtgtc agaggtaagg gagaaaaaat atctttgtgg     540
accaagaatg ctgcaaatga aacggctcag gttagcattg gtaagcaatg gaagcagttt     600
ctggattaca gcgacagtgt tggcttcata tttcacgacg atgcaaagag gctcgacaga     660
aatgcaaaga atcgttacac cgtatag                                        687

<210> SEQ ID NO 6
<211> LENGTH: 228
<212> TYPE: PRT
<213> ORGANISM: Capsicum annuum

<400> SEQUENCE: 6

Met Ala Thr Ala Glu Met Glu Lys Thr Thr Thr Phe Asp Glu Ala Glu
 1               5                  10                  15

Lys Val Lys Leu Asn Ala Asn Glu Ala Asp Asp Glu Val Glu Glu Gly
            20                  25                  30

Glu Ile Val Glu Glu Thr Asp Asp Thr Thr Ser Tyr Leu Ser Lys Glu
        35                  40                  45

Ile Ala Thr Lys His Pro Leu Glu His Ser Trp Thr Phe Trp Phe Asp
    50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asp Leu His Cys
            100                 105                 110

Phe Lys His Lys Ile Glu Pro Lys Trp Glu Asp Pro Val Cys Ala Asn
        115                 120                 125

Gly Gly Thr Trp Lys Met Ser Phe Ser Lys Gly Lys Ser Asp Thr Ser
```

-continued

```
                130                 135                 140
Trp Leu Tyr Thr Leu Leu Ala Met Ile Gly His Gln Phe Asp His Glu
145                 150                 155                 160

Asp Glu Ile Cys Gly Ala Val Val Ser Val Arg Gly Lys Gly Glu Lys
                165                 170                 175

Ile Ser Leu Trp Thr Lys Asn Ala Ala Asn Glu Thr Ala Gln Val Ser
                180                 185                 190

Ile Gly Lys Gln Trp Lys Gln Phe Leu Asp Tyr Ser Asp Ser Val Gly
                195                 200                 205

Phe Ile Phe His Asp Asp Ala Lys Arg Leu Asp Arg Asn Ala Lys Asn
                210                 215                 220

Arg Tyr Thr Val
225
```

<210> SEQ ID NO 7
<211> LENGTH: 687
<212> TYPE: DNA
<213> ORGANISM: Capsicum annuum

<400> SEQUENCE: 7

```
atggcaacag ctgaaatgga gaaaacgacg acgtttgatg aagctgagaa ggtgaaattg      60
aatgctaatg aggcagatga tgaagttgaa gaaggtgaaa ttgttgaaga aactgatgat     120
acgacgtcgt atttgagcaa agaaatagca acaaagcatc cattagagca ttcatggact     180
ttctggtttg ataatccaga ggcgaaatcg aaacaagctg cttggggtag ctcgcgtcgc     240
aacgtctaca ctttctccac tgttgaagat ttttggggtg cttacaataa tatccaccac     300
ccaagcaagt tagttgtggg agcaaactta cattgtttca gcataaaaat tgagccaaag     360
tgggaagatc ctgtatgtgc caatggaggg acatggaaaa tgagttttc aaagggtaaa     420
tctgatacca gctggctata tacgctgctt gcaatgattg gacatcaatt cgatcatgaa     480
gatgaaattt gtggagcagt agttagtgtc agaggtaagg gagaaaaaat atctttgtgg     540
accaagaatg ctgcaaatga aacggctcag gttagcattg gtaagcaatg gaagcagttt     600
ctggattaca gcgacagtgt tggcttcata tttcacgacg atgcaaagag gctcgacaga     660
aatgccaaga atcgttacac cgtatag                                          687
```

<210> SEQ ID NO 8
<211> LENGTH: 228
<212> TYPE: PRT
<213> ORGANISM: Capsicum annuum

<400> SEQUENCE: 8

```
Met Ala Thr Ala Glu Met Glu Lys Thr Thr Thr Phe Asp Glu Ala Glu
1               5                   10                  15

Lys Val Lys Leu Asn Ala Asn Glu Ala Asp Asp Glu Val Glu Glu Gly
                20                  25                  30

Glu Ile Val Glu Glu Thr Asp Asp Thr Thr Ser Tyr Leu Ser Lys Glu
            35                  40                  45

Ile Ala Thr Lys His Pro Leu Glu His Ser Trp Thr Phe Trp Phe Asp
        50                  55                  60

Asn Pro Glu Ala Lys Ser Lys Gln Ala Ala Trp Gly Ser Ser Arg Arg
65                  70                  75                  80

Asn Val Tyr Thr Phe Ser Thr Val Glu Asp Phe Trp Gly Ala Tyr Asn
                85                  90                  95

Asn Ile His His Pro Ser Lys Leu Val Val Gly Ala Asn Leu His Cys
```

-continued

```
                100                 105                 110
Phe Lys His Lys Ile Glu Pro Lys Trp Glu Asp Pro Val Cys Ala Asn
        115                 120                 125
Gly Gly Thr Trp Lys Met Ser Phe Ser Lys Gly Lys Ser Asp Thr Ser
    130                 135                 140
Trp Leu Tyr Thr Leu Leu Ala Met Ile Gly His Gln Phe Asp His Glu
145                 150                 155                 160
Asp Glu Ile Cys Gly Ala Val Val Ser Val Arg Gly Lys Gly Glu Lys
                165                 170                 175
Ile Ser Leu Trp Thr Lys Asn Ala Ala Asn Glu Thr Ala Gln Val Ser
        180                 185                 190
Ile Gly Lys Gln Trp Lys Gln Phe Leu Asp Tyr Ser Asp Ser Val Gly
    195                 200                 205
Phe Ile Phe His Asp Asp Ala Lys Arg Leu Asp Arg Asn Ala Lys Asn
210                 215                 220
Arg Tyr Thr Val
225
```

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence:   Primer

<400> SEQUENCE: 9
atggcaacag ctgaaatgg                                              19

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:   Primer

<400> SEQUENCE: 10
tatacggtgt aacgattctt ggca                                        24

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence:   Primer

<400> SEQUENCE: 11
aatatccatc acccaag                                                17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:   Primer

<400> SEQUENCE: 12
gctccacata tttcatc                                                17

<210> SEQ ID NO 13
<211> LENGTH: 21
<212> TYPE: DNA
<213> ORGANISM: Artificial Sequence

```
<220> FEATURE:
<223> OTHER INFORMATION: Description of Artificial Sequence:  Primer

<400> SEQUENCE: 13
ttacacgcgc cgatacactt g                                              21

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence:  Primer

<400> SEQUENCE: 14
catcatctgc cttcattagc attcaat                                        27

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:  Primer

<400> SEQUENCE: 15
aacaatggcc accgaagc                                                  18

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:  Primer

<400> SEQUENCE: 16
atttcacaca gtatatcggc tct                                            23

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:  Primer

<400> SEQUENCE: 17
atcgatggca acagctgaaa tgg                                            23

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:  Primer

<400> SEQUENCE: 18
ctatacggtc taacgattct                                                20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:  Primer

<400> SEQUENCE: 19
ttaggcaaac caatcacaat g                                              21
```

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 20
cctgttgtaa cgatagaact a                                         21

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 21
caccttcttc aacttcatca tctgcct                                   27

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 22
agctgaaatg gagaaaacga cga                                       23

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 23
tttgatgaag ctgagaaggt gaaattg                                   27

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 24
cggcttgaaa gttcagttag tcaac                                     25

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 25
gccaactaac ttagctacta agattttcag                                30

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 26
gccattcgac taatcctcag caac                                              24

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 27
cctccattgg cacatacagg atct                                              24

<210> SEQ ID NO 28
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 28
cactctagta atattatttt ctgt                                              24

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 29
tgaaatatga agccaacact g                                                 21

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 30
ggtaagcaat ggaagcagtt tctg                                              24

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 31
cagtttctgg attacagcga cagt                                              24

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 32
gccgaattca tggggaagaa gaatcaga                                          28

<210> SEQ ID NO 33

```
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 33
ccctcgagct attgcgtgta caccaattc                                    29

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 34
gaattcatgg caacagctga a                                            21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 35
ctcgagctat acggtgtaac g                                            21

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 36
ccgaattcat gggagagaag aggaaatg                                     28

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 37
ccctcgagct actgaaaata aagattctc                                    29

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 38
ccatatggca acagctga                                                18

<210> SEQ ID NO 39
<211> LENGTH: 24
<212> TYPE: DNA
<213> ORGANISM: Artificial Sequence
```

-continued

```
<220> FEATURE:
<223> OTHER INFORMATION: Description of Artificial Sequence:  Primer

<400> SEQUENCE: 39
ccctcgagct atacggtgta acga                                            24
```